(12) United States Patent
Yuan et al.

(10) Patent No.: US 10,508,102 B2
(45) Date of Patent: Dec. 17, 2019

(54) INHIBITORS OF CELLULAR NECROSIS AND RELATED METHODS

(71) Applicants: President and Fellows of Harvard College, Cambridge, MA (US); Shanghai Institute of Organic Chemistry, Chinese Academy of Sciences, Shanghai (CN)

(72) Inventors: Junying Yuan, Newton, MA (US); Yijun Zhou, Shanghai (CN); Shan Qian, Shanghai (CN); Dawei Ma, Shanghai (CN)

(73) Assignees: President and Fellows of Harvard College, Cambridge, MA (US); Shanghai Institute of Organic Chemistry, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 15/897,787

(22) Filed: Feb. 15, 2018

(65) Prior Publication Data

US 2019/0023690 A1    Jan. 24, 2019

Related U.S. Application Data

(62) Division of application No. 14/966,968, filed on Dec. 11, 2015, now Pat. No. 9,944,628.

(60) Provisional application No. 62/105,475, filed on Jan. 20, 2015, provisional application No. 62/105,462, filed on Jan. 20, 2015.

(30) Foreign Application Priority Data

Dec. 11, 2014    (CN) .......................... 2014 1 0764426
Dec. 11, 2014    (CN) .......................... 2014 1 0767595

(51) Int. Cl.
| C07D 403/06 | (2006.01) |
| C07D 233/78 | (2006.01) |
| A61P 29/00 | (2006.01) |
| A61P 9/10 | (2006.01) |

(52) U.S. Cl.
CPC ............. *C07D 403/06* (2013.01); *A61P 9/10* (2018.01); *A61P 29/00* (2018.01); *C07D 233/78* (2013.01)

(58) Field of Classification Search
CPC ..... C07D 403/06; C07D 233/78; A61P 29/00; A61P 9/10
See application file for complete search history.

(56) References Cited

U.S. PATENT DOCUMENTS

| 3,932,430 | A | 1/1976 | Habeck et al. |
| 4,016,037 | A | 4/1977 | Mitsugi et al. |
| 4,110,536 | A | 8/1978 | Havera et al. |
| 4,177,054 | A | 12/1979 | Arndt et al. |
| 4,332,952 | A | 6/1982 | Schnur |
| 4,618,609 | A | 10/1986 | Alker et al. |
| 4,684,735 | A | 8/1987 | Mirviss |
| 4,705,864 | A | 11/1987 | Cesa et al. |
| 4,837,165 | A | 6/1989 | Hawke |
| 4,868,061 | A | 9/1989 | Cesa et al. |
| 4,911,931 | A | 3/1990 | Baylink |
| 5,108,914 | A | 4/1992 | Wagner et al. |
| 5,300,412 | A | 4/1994 | Mihayashi et al. |
| 5,334,606 | A | 8/1994 | MacLeod |
| 5,338,859 | A | 8/1994 | Bhattacharya |
| 5,574,030 | A | 11/1996 | Masaki et al. |
| 5,593,697 | A | 1/1997 | Barr et al. |
| 5,693,643 | A | 12/1997 | Gilbert et al. |
| 5,714,355 | A | 2/1998 | Wagner et al. |
| 5,830,854 | A | 11/1998 | Hargreaves |
| 6,194,444 | B1 | 2/2001 | Tsubata et al. |
| 6,235,910 | B1 | 5/2001 | Beller et al. |
| 6,251,929 | B1 | 6/2001 | Naiki et al. |

(Continued)

FOREIGN PATENT DOCUMENTS

| CN | 102850252 A | 1/2013 |
| DE | 10342839 A1 | 4/2005 |

(Continued)

OTHER PUBLICATIONS

RN1044508-97-5, Aug. 2008, registry database compound.*

(Continued)

*Primary Examiner* — Sun Jae Yoo

(74) *Attorney, Agent, or Firm* — Choate, Hall & Stewart LLP; Brenda H. Jarrell; Nicholas J. Pace

(57) ABSTRACT

A compound having the following structure (I):

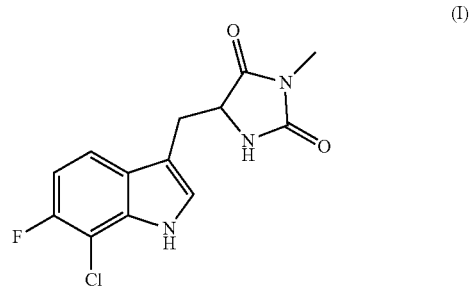

or a pharmaceutically acceptable salt, prodrug, stereoisomer or tautomer thereof, is provided. Related compounds, methods for preparation of the same and uses of the compounds for treatment of various indications, including treatment of necrotic cell diseases and/or inflammation, are also provided.

16 Claims, 1 Drawing Sheet

(56) References Cited

U.S. PATENT DOCUMENTS

| | | | |
|---|---|---|---|
| 6,300,349 B1 | 10/2001 | Margolin | |
| 6,521,649 B1 | 2/2003 | Kuroda et al. | |
| 6,734,174 B1 | 5/2004 | Wallach et al. | |
| 6,756,394 B1 | 6/2004 | Yuan et al. | |
| 6,797,708 B2 | 9/2004 | McKew et al. | |
| 6,846,839 B1 | 1/2005 | Tang et al. | |
| 6,887,993 B1 | 5/2005 | Tian et al. | |
| 7,019,004 B2 | 3/2006 | Berney et al. | |
| 7,189,856 B2 | 3/2007 | Shapiro et al. | |
| 7,253,201 B2 | 8/2007 | Yuan et al. | |
| 7,379,820 B2 | 5/2008 | Sukits et al. | |
| 7,491,743 B2 | 2/2009 | Cuny et al. | |
| 7,803,828 B2 | 9/2010 | McCormick et al. | |
| 8,143,300 B2 | 3/2012 | Cuny et al. | |
| 8,278,344 B2 | 10/2012 | Cuny et al. | |
| 8,324,262 B2 | 12/2012 | Yuan et al. | |
| 8,420,683 B2 | 4/2013 | Sarakinos et al. | |
| 8,658,689 B2 | 2/2014 | Cuny et al. | |
| 8,664,192 B2 | 3/2014 | Croce | |
| 8,741,942 B2 | 6/2014 | Cuny et al. | |
| 9,108,955 B2 | 8/2015 | Cuny et al. | |
| 9,163,256 B2 | 10/2015 | Palli et al. | |
| 9,499,521 B2 * | 11/2016 | Yuan | C07D 403/06 |
| 9,944,628 B2 | 4/2018 | Yuan et al. | |
| 10,022,419 B2 * | 7/2018 | Vavvas | A61K 45/06 |
| 2002/0013350 A1 | 1/2002 | Nishiguchi et al. | |
| 2002/0055308 A1 | 5/2002 | Ibata et al. | |
| 2002/0064736 A1 | 5/2002 | Uehira et al. | |
| 2002/0155172 A1 | 10/2002 | Yuan et al. | |
| 2003/0083386 A1 | 5/2003 | Yuan et al. | |
| 2004/0019092 A1 | 1/2004 | Berney et al. | |
| 2004/0259904 A1 | 12/2004 | Tong et al. | |
| 2005/0119260 A1 | 6/2005 | Cuny et al. | |
| 2005/0131044 A1 | 6/2005 | Yuan et al. | |
| 2006/0183190 A1 | 8/2006 | Suzuki et al. | |
| 2006/0198893 A1 | 9/2006 | Lindfors | |
| 2007/0099936 A1 | 5/2007 | Bian et al. | |
| 2008/0045541 A1 | 2/2008 | Gielen-Haertwig et al. | |
| 2008/0234270 A1 | 9/2008 | Canne Bannen et al. | |
| 2009/0099186 A1 | 4/2009 | Beigelman et al. | |
| 2009/0099242 A1 | 4/2009 | Cuny et al. | |
| 2009/0208991 A1 | 8/2009 | Ludwig Bitter et al. | |
| 2010/0081678 A1 | 4/2010 | Crooks et al. | |
| 2010/0087453 A1 | 4/2010 | Yuan et al. | |
| 2010/0190836 A1 | 7/2010 | Yuan et al. | |
| 2010/0317701 A1 | 12/2010 | Cuny et al. | |
| 2011/0144169 A1 | 6/2011 | Cuny et al. | |
| 2012/0122889 A1 | 5/2012 | Yuan et al. | |
| 2012/0149702 A1 | 6/2012 | Cuny et al. | |
| 2012/0309795 A1 | 12/2012 | Cuny et al. | |
| 2013/0040949 A1 | 2/2013 | Gray et al. | |
| 2013/0158024 A1 | 6/2013 | Yuan et al. | |
| 2014/0024657 A1 | 1/2014 | Yuan et al. | |
| 2014/0024662 A1 | 1/2014 | Yuan et al. | |
| 2014/0128437 A1 | 5/2014 | Cuny et al. | |
| 2014/0323489 A1 | 10/2014 | Yuan et al. | |
| 2015/0079118 A1 | 3/2015 | Howarth et al. | |
| 2015/0105434 A1 | 4/2015 | Porter et al. | |
| 2015/0202250 A1 | 7/2015 | Sekaran et al. | |
| 2015/0353533 A1 | 12/2015 | Bandyopadhyay et al. | |
| 2015/0361396 A1 | 12/2015 | Regev et al. | |
| 2016/0024098 A1 | 1/2016 | Yuan et al. | |
| 2016/0102053 A1 | 4/2016 | Cuny et al. | |
| 2016/0168128 A1 | 6/2016 | Yuan et al. | |

FOREIGN PATENT DOCUMENTS

| | | | |
|---|---|---|---|
| EP | 533243 A1 | 3/1993 | |
| EP | 579169 A1 | 1/1994 | |
| EP | 0343643 B1 | 3/1994 | |
| EP | 640594 A1 | 3/1995 | |
| EP | 1275646 A1 | 1/2003 | |
| EP | 1447401 A1 | 8/2004 | |
| EP | 3017825 A1 | 5/2016 | |
| GB | 2080803 A | 2/1982 | |
| GB | 2128184 A | 4/1984 | |
| JP | S49-66678 A | 6/1974 | |
| JP | S55-23994 A | 2/1980 | |
| JP | S55-136279 A | 10/1980 | |
| JP | S61-22081 A | 1/1986 | |
| JP | S62-56457 A | 3/1987 | |
| JP | H01-228489 A | 9/1989 | |
| JP | H0148758 B2 | 10/1989 | |
| JP | H02-19363 A | 1/1990 | |
| JP | H05-4910 A | 1/1993 | |
| JP | 06059227 B2 | 8/1994 | |
| JP | 3163361 B2 | 5/2001 | |
| JP | 2002145192 A | 5/2002 | |
| JP | 2002/330785 A | 11/2002 | |
| JP | 2003/198785 A | 7/2003 | |
| JP | 2010202575 A | 9/2010 | |
| JP | 2010275229 A | 12/2010 | |
| WO | WO-90/04183 A1 | 4/1990 | |
| WO | WO-92/04045 A1 | 3/1992 | |
| WO | WO-96/07405 A1 | 3/1996 | |
| WO | WO-96/30393 A1 | 10/1996 | |
| WO | WO-1996/036730 A1 | 11/1996 | |
| WO | WO-1997/015586 A1 | 5/1997 | |
| WO | WO-97/40023 A1 | 10/1997 | |
| WO | WO-98/33776 A1 | 8/1998 | |
| WO | WO-98/39303 A1 | 9/1998 | |
| WO | WO-00/018786 A1 | 4/2000 | |
| WO | WO-01/007044 A1 | 2/2001 | |
| WO | WO-01/007048 A1 | 2/2001 | |
| WO | WO-01/28493 A2 | 4/2001 | |
| WO | WO-01/85718 A1 | 11/2001 | |
| WO | WO-02/014865 | 2/2002 | |
| WO | WO-02/080855 A2 | 10/2002 | |
| WO | WO-03/027081 A2 | 4/2003 | |
| WO | WO-03/042234 A2 | 5/2003 | |
| WO | WO-03/057214 A1 | 7/2003 | |
| WO | WO-03/068914 A2 | 8/2003 | |
| WO | WO-2004/023146 A2 | 3/2004 | |
| WO | WO-2004/050894 A2 | 6/2004 | |
| WO | WO-2004/056347 A2 | 7/2004 | |
| WO | WO-2004/070050 A2 | 8/2004 | |
| WO | WO-2004/080480 A1 | 9/2004 | |
| WO | WO-2004/080481 A1 | 9/2004 | |
| WO | WO-2005/028664 A2 | 3/2005 | |
| WO | WO-2005/077344 A2 | 8/2005 | |
| WO | WO-2005/107782 A2 | 11/2005 | |
| WO | WO-2006/086358 A2 | 8/2006 | |
| WO | WO-2006/103995 A1 | 10/2006 | |
| WO | WO-2007/075772 A2 | 7/2007 | |
| WO | WO-2007/087906 A1 | 8/2007 | |
| WO | WO-2008/006883 A2 | 1/2008 | |
| WO | WO-2008/045406 A2 | 4/2008 | |
| WO | WO-2009/023272 A1 | 2/2009 | |
| WO | WO-2009/045397 A1 | 4/2009 | |
| WO | WO-2009/105140 A2 | 8/2009 | |
| WO | WO-2010/075290 A1 | 7/2010 | |
| WO | WO-2010/075561 A1 | 7/2010 | |
| WO | WO-2010/112365 A1 | 10/2010 | |
| WO | WO-2011/106491 A2 | 9/2011 | |
| WO | WO-2011/115725 A2 | 9/2011 | |
| WO | WO-2011/123609 A1 | 10/2011 | |
| WO | WO-2011/133964 A2 | 10/2011 | |
| WO | WO-2012/061045 A2 | 5/2012 | |
| WO | WO-2012/122239 A1 | 9/2012 | |
| WO | WO-2012/154858 A1 | 11/2012 | |
| WO | WO-2013/013826 A1 | 1/2013 | |
| WO | WO-2013/032693 A2 | 3/2013 | |
| WO | WO-2013/059791 A2 | 4/2013 | |
| WO | WO-2013/071203 A1 | 5/2013 | |
| WO | WO-2014/008167 A2 | 1/2014 | |
| WO | WO-2014/125444 A1 | 8/2014 | |
| WO | WO-2014/126127 A1 | 8/2014 | |
| WO | WO-2014/145022 A1 | 9/2014 | |
| WO | WO-2014/147124 A1 | 9/2014 | |
| WO | WO-2014/152182 A1 | 9/2014 | |
| WO | WO-2014152182 A1 * | 9/2014 | A61K 31/4178 |
| WO | WO-2014/170892 A1 | 10/2014 | |
| WO | WO-2015/039705 A1 | 3/2015 | |
| WO | WO-2015/049289 A2 | 4/2015 | |

(56) References Cited

FOREIGN PATENT DOCUMENTS

| | | |
|---|---|---|
| WO | WO-2015/077709 A2 | 5/2015 |
| WO | WO-2015/095449 A1 | 6/2015 |
| WO | WO-2015/105657 A1 | 7/2015 |
| WO | WO-2015/105658 A1 | 7/2015 |
| WO | WO-2015/154197 A1 | 10/2015 |
| WO | WO-2016/023918 A1 | 2/2016 |
| WO | WO-2016/025129 A1 | 2/2016 |
| WO | WO-2016/044777 A1 | 3/2016 |
| WO | WO-2016/094846 A1 | 6/2016 |
| WO | WO-2016/101885 A1 | 6/2016 |
| WO | WO-2016/101887 A1 | 6/2016 |

OTHER PUBLICATIONS

Argast et al., Inhibition of RIP2/RICK/CARDIAK activity by pyridinyl imidazole inhibitors of p38 MAPK, Mol Cell Biochem, 268(1-2):129-40 (2005).
Becker, K. and Dewitt, S., A method for the combinatorial synthesis of mixtures of compounds, Accession No. 694374, 2 pages (1996).
Berge et al., Pharmaceutical salts, J Pharm Sci., 66(1):1-19 (1977).
Berger, S. et al., Characterization of GSK'963: a structurally distinct, potent and selective inhibitor of RIP1 kinase, Cell Death Discovery, 1:15009, 7 pages (2015).
Berger, S. et al., Drilling into RIP1 biology: what compounds are in your toolkit?, Cell Death and Disease, 6:E1889, 2 pages (2015).
Boeijen, Combinatorial chemistry of hydantoins, Bioorganic & Medical Chem Lett., 8(17):2375-80 (1998).
Borner et al., Apoptosis without caspases: an inefficient molecular guillotine? Cell Death Differ, 6(6):497-507 (1999).
Braña et al., Reaction of L-tryptophan with alkyl isocyanates. Heterocycles, 26(1):95-100 (1987).
Burk et al., A convenient asymmetric synthesis of alpha-1-arylalkylamines through the enantioselective hydroaenation of enamides, J Am Chem Soc., 118:5142-3 (1996).
Buyukbingol et al., Studies on the synthesis and structure-activity relationships of 5-(3'-indolal)-2-thiohydantoin derivatives as aldose reductase enzyme inhibitors. Farmaco, 49(6):443-7 (1994).
Caplus Accession for Jakse et al., New synthetic routes to thiooxoaplysinopsines and their derivatives, Zbornik Referatov s Posvetovanja Slovenski Kemijski Dnevi, Maribor, Slovenia, Sep. 28-29, 2000 (2 pages).
Caplus Accession for Nowak, Allyl Isothiocyanate in the synthesis of 3-allyl-2-thiohydantoins from amino acids and in the degradation of proteins, Roczniki Chemii, 47(12):2377-8 (1973) (2 pages) (Abstract only).
Caplus Accession for U.S. Pat. No. 4,110,536, dated Aug. 29, 1978 (2 pages).
Caplus Accession for WO 96/30393, dated Oct. 3, 1996 (2 pages).
Chi et al., Oncogenic ras triggers cell suicide through the activation of a caspase-independent cell death program in human cancer cells, Oncogene, 18(13):2281-90 (1999).
Choi, S. et al., Optimization of tricyclic Nec-3 necroptosis inhibitors for in vitro liver microsomal stability, Bioorganic & Medicinal Chemistry Letters, 22:5685-5688 (2012).
Christofferson et al., A novel role for RIP1 kinase in mediating TNFalpha production, Cell Death Dis., 3:e320 (2012) (10 pages).
Compound Summary for CID 51532327, <https://pubchem.ncbi.nlm.nih.gov/compound/51532327#section= Top>, retrieved Feb. 1, 2016 (10 pages).
Cougnoux, A. et al., Necroptosis in Niemann-Pick disease, type C1: a potential therapeutic target, Cell Death and Disease, 7(1-9): 9 pages (2016).
Cryns et al., Proteases to die for, Genes Dev. 12(11):1551-70 (1998).
Degterev et al., Chemical inhibitor of nonapoptotic cell death with therapeutic potential for ischemic brain injury, Nat Chem Biol., 1(2):112-9, 234 (2005).
Degterev, A. et al., Activity and specificity of necrostatin-1, small-molecule inhibitor of RIP1 kinase, Cell Death and Differentiation, 20: 366 (2013).

Degterev, A. et al., Identification of RIP1 kinase as a specific cellular target of necrostatins, Nature Chemical Biology, 4(5):313-321 (2008).
Edman, Method for determination of the amino acid sequence in peptides, Acta Chem Scand., 4:283-93 (1950).
El-Rayyes et al., Heterocycles. Part VIII. Synthesis of new substituted benz[g]indazoles, J Heterocyclic Chem., 23:135-40 (1986).
Eldadah et al., Caspase pathways, neuronal apoptosis, and CNS injury, J Neurotrauma., 17(10):811-29 (2000).
Festjens, N. et al., RIP1, a kinase on the crossroads of a cell's decision to live or die, Cell Death and Differentiation, 14:400-410 (2007).
Fiers et al., More than one way to die: apoptosis, necrosis and reactive oxygen damage, Oncogene, 18(54):7719-30 (1999).
Fujiwara et al., C nuclear magnetic resonance studies on the conformation of substituted hydantoins, J Chem Soc Perkin Trans 2., 1573-7 (1980).
Gulati et al., A new synthesis of 5-bromoaplysinopsin, 6-bromoaplysinopsin and 3'-demethvlaolvsinoosin and their bioloaical activities, Indian J Chem., 33B(1):10-6 (1994).
Hara et al., Inhibition of interleukin 1beta converting enzyme family proteases reduces ischemic and excitotoxic neuronal damaae, Proc Natl Acad Sci U.S.A., 94(5):2007-12 (1997).
Harris, P. et al., Discovery of Small Molecule RIP1 Kinase Inhibitors for the Treatment of Pathologies Associated with Necroptosis, ACS Med. Chem. Lett., 6 pages. (2013).
Harwell et al., Conformationally constrained amino-acids: synthesis of novel beta, beta- , 2,3- , and 3,4-cyclised tryptophans, Tetrahedron Lett., 39(47):8729-32 (1998).
Havera, H. and Strycker, W., Derivatives of 5-(indol-3-yl) hydantoin, Accession No. 121596, 2 pages (1979).
Herceg et al., Failure of poly(ADP-ribose) polymerase cleavage by caspases leads to induction of necrosis and enhanced apoptosis, Mol Cell Biol., 19(7):5124-33 (1999).
Hirsch et al., The apoptosis-necrosis paradox. Apoptogenic proteases activated after mitochondrial permeability transition determine the mode of cell death, Oncogene, 15(13):1573-81 (1997).
Holler et al., Fas triggers an alternative, caspase-8-indepdendent cell death pathway using the kinase RIP as effector molecule, Nature Immunol., 1(6):489-95 (2000).
Horwell, D. et al., Cholecystokinin antagonists their preparation and therapeutic use, Accession No. 484251, 1 page (1992).
Horwell, D. et al., Conformationally Constrained Amino-Acids: Synthesis of Novel β, β- , 2,3- , and 3,4-Cyclised Tryptophans, Tetrahedron Lett., 39(47): 8729-8732 (1998).
Inglis et al., The identification of tryptophan residues in proteins as oxidised derivatives during amino acid sequence determinations, FEBS Letters, 104(1):115-8 (1979).
International Preliminary Report on Patentability for International Patent Application No. PCT/US2004/028270, dated Feb. 28, 2006 (8 pages).
International Preliminary Report on Patentability for International Patent Application No. PCT/US2006/048583, dated Jan. 13, 2009 (7 pages).
International Search Report and Written Opinion for International Application No. PCT/US15/65349, dated Feb. 23, 2016 (11 pages).
International Search Report and Written Opinion for International Application No. PCT/US2009/069483, dated May 5, 2010 (11 pages).
International Search Report and Written Opinion of the International Search Authority for International Application No. PCT/US2006/048583, dated Dec. 8, 2008 (9 pages).
International Search Report for International Patent Application No. PCT/US2000/28475, dated Apr. 5, 2001 (4 pages).
International Search Report for International Patent Application No. PCT/US2004/028270, dated Jan. 18, 2006 (7 pages).
Jagtap et al., Structure-activity relationship study of tricyclic necroptosis inhibitors, J Med Chem., 50(8):1886-95 (2007).
Jakse et al., New synthetic routes to thiooxoaplysinopsines and their derivatives. Zbornik Referatov s Posvetovanja Slovenski Kemijski Dnevi, Sep. 28-29, Maribor, Slovenia. Issue Pt. 1: 141-146 (2000) (English abstract included).

(56) References Cited

OTHER PUBLICATIONS

Janin et al., Methyl orthocarboxylates as methylating agents of heterocycles, Eur J Org Chem., 1763-9 (2002).
Juo et al., FADD is required for multiple signaling events downstream of the receptor Fas, Cell Growth Differ., 10(12):797-804 (1999).
Kaul et al., Pathways to neuronal injury and apoptosis in HIV-associated dementia, Nature, 410(6831):988-94 (2001).
Kawahara et al., Caspase-independent cell killing by fas-associated protein with death domain, J Cell Biol., 143(5):1353-60 (1998).
Kazlauskas et. al., Aplysinopsin, a new tryptophan derivative from a sponge, Tetrahedron Lett., 1:61-4 (1977).
Khodair, A convenient synthesis of glycosylated hydantoins as potential antiviral agents, Phosphorus Sulfur Silicon Relat Elem., 122:9-26 (1997).
Khwaja et al., Resistance to the cytotoxic effects of tumor necrosis factor alpha can be overcome by inhibition of a FADD/Caspase-dependent signaling pathway, J Biol Chem., 274(51):36817-23 (1999).
Kitanaka et al., Caspase-independent programmed cell death with necrotic morphology, Cell Death Differ., 6(6):508-15 (1999).
Ichihara et al., The acid diazo reaction and 5- or 7-hydroxyindole derivatives: oxidation of the benzene moiety of indolelactic acid, indolepropionic acid, and indolylethylamine, etc., by liver extract, J Biochem. (Tokyo) 44:649-59 (1957) (abstract only).
Leist et al., Inhibition of mitochondrial ATP generation by nitric oxide switches apoptosis to necrosis, Exp Cell Res., 249(2):396-403 (1999).
Lewis et al., Tryptophan-derived NK1 antagonists: conformationally constrained heterocyclic bioisosteres of the ester linkage, J Med Chem., 38:923-33 (1995).
Li et al., Induction of necrotic-like cell death by tumor necrosis factor alpha and caspase inhibitors: novel mechanism for killing virus-infected cells, J Viral., 74(16):7470-7 (2000).
Linkermann, A. et al., The RIP1-Kinase Inhibitor Necrostatin-1 Prevents Osmotic Nephrosis and Contrast-Induced AKI in Mice, J Am Soc Nephrol, 24:1545-1557 (2013).
Lu et al., SM-164: a novel, bivalent Smac mimetic that induces apoptosis and tumor regression by concurrent removal of the blockade of cIAP-1/2 and XIAP, Cancer Res., 68(22):9384-93 (2008).
Luschen et al., Sensitization to death receptor cytotoxicity by inhibition of fas-associated death domain protein (FADD)/caspase signaling. Requirement of cell cycle progression, J Biol Chem., 275(32):24670-8 (2000).
Maki, J. and Degterev, A., Activity Assays for Receptor-Interacting Protein Kinase 1: A Key Regulator of Necroptosis, Methods in Molecular Biology, 1004:31-42 (2013).
Maki, J. et al., Fluorescence polarization assay for inhibitors of the kinase domain of receptor interacting protein 1, Anal Biochem, 427(2):164-174 (2012).
Marchant et al., Synthesis of 5- and 7-methoxytryptophan and of some derivatives, J Chem Soc., 1808-11 (1951) (Abstract only).
Martin et al., Neurodegeneration in excitotoxicity, global cerebral ischemia, and target deprivation: A perspective on the contributions of apoptosis and necrosis, Brain Res Bull., 46(4):281-309 (1998).
Matsumura et al., Necrotic death pathway in fas receptor signaling, J Cell Biol., 151(6):1247-55 (2000).
McCarthy et al., Inhibition of ced-3/ICE-related proteases does not prevent cell death induced by oncogenes, DNA damage, or the Bcl-2 homologue bak, J Cell Biol., 136(1):215-27 (1997).
McMurray, Huntington's disease: new hope for therapeutics, Trends Neurosci., 24(11 Suppl):S32-8 (2001).
Molina et al., A simple and general entry to aplysinopsine-type alkaloids by tandem aza-wittig/heterocumulene-mediated annelation, Tet Lett., 33(31):4491-4 (1992).
Najjar, M. et al., Structure Guided Design of Potent and Selective Ponatinib-Based Hybrid Inhibitors for RIPK1, Cell Reports, 10:1850-1860 (2015).

Nicotera et al., Apoptosis and necrosis: different execution of the same death, Biochem Soc Symp., 66:69-73 (1999).
No Author Listed, Enbrel, Medication Guide, http://www.fda.gov/downloads/Drugs/DrugSafety/ucm088590.pdf, 7 pages (2016).
No Author Listed, FDA-approved treatments for Alzheimer's, Alzheimer's Association, http://www.alz.org/dementia/downloads/topicsheet_treatments.pdf, 3 pages (2017).
No Author Listed, Frontotemporal dementia, May Clinic, http://www.mayoclinic.org/diseases-conditions/frontotemporal-dementia/diagnosis-treatment/treatment/txc-20260754, 5 pages (2017).
No Author Listed, IBD, http://www.womenshealth.gov/publications/our-publications/fact-sheet/inflammatory-bowel-disease.html, 13 pages (2016).
No Author Listed, Infliximab, http://www.fda.gov/downloads/Drugs/DrugSafety/ucm088590.pdf, 5 pages (2016).
No Author Listed, Medication Guide, Glaucoma Research Foundation, http://www.glaucoma.org/treatment/medication-guide.php, 3 pages (2017).
No Author Listed, Parkinsons, http://www.mayoclinic.org/diseases-conditions/parkinsons-disease/basics/treatment/con-20028488, 5 pages (2016).
No Author Listed, Parkinsons-prevention, http://answers.webmd.com/answers/1192098/how-can-parkinsons-disease-be-prevented, 2 pages (2016).
No Author Listed, UC-prevention, http://www.healthcommunities.com/colitis/prevention.shtml, 3 pages (2016).
Nowak, Application of allylisothiocyanate in synthesis of 3-allyl-2-thiohydantoins from amino acids and in the degradation of proteins, Roczniki Chemii, 47(12):2377-8 (1973).
Ooms et al., Exploration of the pharmacophore of 3-alkyl-5-arylimidazolidinediones as new CB1 cannabinoid receptor ligands and potential antagonists: synthesis, lipophilicity, affinity and molecular modeling, J Med Chem., 45(9):1748-56 (2002).
Park et al., Diastereoselective synthesis of hydantoin- and isoxazoline-substituted dispirocvclobutanoids, J Org Chem., 65(11):3520-4 (2000).
Partial European Search Report for European Application No. 10011481.8, dated Jun. 7, 2011 (6 pages).
Patani, G. and Lavoie, E., Bioisosterism: A Rational Approach in Drug Design, Chem. Rev., 96:3147-3176 (1996).
Phillips, R. and Cohen, L., Intramolecular General Acid and General Base Catalyses in the Hydrolysis of 2 Halotryptophans and Their Analogues, Journal of the American Chemical Society, 108:2023-2030 (2011).
Polniaszek et al., Stereoselective nucleophilic additions to the carbon-nitrogen double bond. 3. chiral acyliminium ions, J Ora Chem., 55(1):215-23 (1990).
Polverino et al., Selective activation of caspases during apoptotic induction in HL-60 cells, J Biol Chem., 272(11):7013-21 (1997).
Raghupathi et al., Apoptosis after traumatic brain injury, J Neurotrauma., 17(10):927-38 (2000).
Rahman et al., Synthesis and biological studies of thiohydantoins, Bangladesh J Bio Sci., 5(1):28-30 (1976).
Sane et al., Caspase inhibition in camptothecin-treated U-937 cells is coupled with a shift from apoptosis to transient G1 arrest followed by necrotic cell death, Cancer Res., 59(15):3565-9 (1999).
Selic et al., A simple stereoselective synthesis of aplysinopsin analogs, Helv Chim Acta., 83(10):2802-11 (2000).
Selkoe, Translating cell biology into therapeutic advances in alzheimer's disease, Nature, 399(6738 Suppl):A23-A31 (1999).
Suzuki et al., Proton nuclear magnetic resonance studies on methylthiohydantoins, thiohydantoins, and hydantoins of amino acids, Can J Biochem., 55(5):521-7 (1977).
Swan, Thiohydantoins. I. Preparation of some 2-thiohydantoins from amino acids and acylamino acids, Australian J. Sci Res., A5:711-20 (1952) (Abstract only).
Syntichaki et al., Death by necrosis. Uncontrollable catastrophe, or is there order behind the chaos? EMBO Rep., 3(7):604-9 (2002).
Szöllösy et al., Fused heterocycles. Part 4. Synthesis and stereochemistry of hexahydrobenzol[6,7]Cycloheptal[1,2-c]Pyrazoles, J Chem Soc Perkin Trans., 2:489-93 (1991).
Takahashi et al., Antimutagenic properties of 3, 5-disubstituted 2-thiohydantoins, J Agric Food Chem., 46:5037-42 (1998).

(56) References Cited

OTHER PUBLICATIONS

Takahashi, N. et al., Necrostatin-1 analogues: critical issues on the specificity, activity and in vivo use in experimental disease models, Cell Death and Disease, 3:e437, 10 pages (2012).
Talanian et al., Caspases as targets for anti-inflammatory and anti-apoptotic drug discovery, J Med Chem., 43(18):3351-71 (2000).
Teng et al.,Structure-activity relationship study of novel necroptosis inhibitors, Bioorg Med Chem Lett., 15(22):5039-44 (2005).
Teng, X. et al., Structure-activity relationship and liver microsome stability studies of pyrrole necroptosis inhibitors, Bioorganic & Medicinal Chemistry Letters, 18:3219-3223 (2008).
Teng, X. et al., Structure-activity relationship study of [1,2,3]thiadiazole necroptosis inhibitors, Bioorganic & Medicinal Chemistry Letters, 17:6836-6840 (2007).
Toniolo, Optical rotatory properties of methylisothiocyanate-amino acid adducts, Tetrahedron, 26:5479-88 (1970).
Tuttolomondo, A. et al., Studies of selective TNF inhibitors in the treatment of brain injury from stroke and trauma: a review of the evidence to date, Drug Design, Development and Therapy, 8:2221-2239 (2014).
Vandenabeele, P. et al., Necrostatin-1 blocks both RIPK1 and IDO: consequences for the study of cell death in experimental disease models, Cell Death and Differentiation, pp. 1-3 (2012).
Vercammen et al., Dual signaling of the fas receptor: initiation of both apoptotic and necrotic cell death pathways, J Exp Med., 188(5):919-30 (1998).
Vercammen et al., Inhibition of caspases increases the sensitivity of L929 cells to necrosis mediated by tumor necrosis factor, J Exp Med., 187(9):1477-85 (1998).
Vila et al., Engineered modeling and the secrets of Parkinson's disease, Trends Neurosci., 24(11 Suppl):S49-55 (2001).
Waterfield et al., Amino acid sequence analysis with methyl isothiocyanate. Resolution of the methylthiohydantoins by gas-liquid partition chromatography, Biochemistry, 9(4):832-9 (1970).
Woo, Gas chromatographic determination of methylthiohydantoin amino acid as N(O)-Butyldimethylsilyl derivatives in amino acid sequencing with methylisothiocyanate, J Korean Agric Chem Soc., 35(2):132-8 (1992).
Wu, Z. et al., A novel necroptosis inhibitor-necrostatin-21 and its SAR study, Bioorganic & Medicinal Chemistry Letters, 23:4903-4906 (2013).
Wyllie et al., Cell death: the significance of apoptosis, Int Rev Cytol., 68:251-306 (1980).
Xie, T. et al., Structural Basis of RIP1 Inhibition by Necrostatins, Structure, 21:493-499 (2013).
Yuan et al., Apoptosis in the nervous system, Nature, 407(6805):802-9 (2000).
Zhang, D. et al., Receptor-interacting protein (RIP) kinase family, Cellular & Molecular Immunology, 7:243-249 (2010).
Zhou, Y. et al., Protective Effects of Necrostatin-1 against Concanavalin A-Induced Acute Hepatic Injury in Mice, Mediators of Inflammation, Article ID 706156, 15 pages (2013).

\* cited by examiner

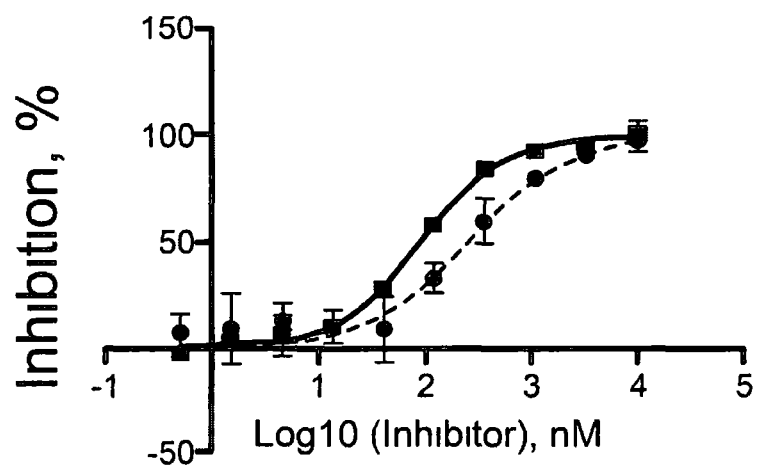

INHIBITORS OF CELLULAR NECROSIS AND RELATED METHODS

CROSS-REFERENCE TO RELATED APPLICATIONS

This application is a divisional of U.S. application Ser. No. 14/966,968, filed Dec. 11, 2015 (now U.S. Pat. No. 9,944,628), which claims the benefit of and priority to U.S. Provisional Application No. 62/105,475, filed Jan. 20, 2015, and U.S. Provisional Application No. 62/105,462, filed Jan. 20, 2015, the contents of each of which are hereby incorporated by reference in their entireties.

GOVERNMENT LICENSE RIGHTS

This invention was made with government support under R01AG047231, R01NS082257, and U01NS050560, awarded by the National Institutes of Health. The government has certain rights in the invention.

BACKGROUND

Technical Field

This invention generally relates to inhibitors of necrosis and methods for their use and preparation. The compounds, and compositions comprising the same, can be used in methods for preventing and/or treating diseases involving cell death and/or inflammation.

Description of the Related Art

Programmed necrotic cell death, also called necroptosis, is a form of cell death in which various stimuli such as TNFα, certain toll-like receptor (TLR) agonists, and ischemia can induce cellular necrosis. Necroptosis is a highly inflammatory form of cell death and is thought to be an important contributor to pathology in multiple degenerative and inflammatory diseases. These diseases include neurodegenerative diseases, stroke, coronary heart disease and myocardial infarction, retinal degenerative diseases, inflammatory bowel disease, kidney disease, liver disease, and others.

Necrosis is characterized by cell membrane and organelle disruption, cell swelling and mitochondrial impairment, followed by cell lysis (Syntichaki, P.; Tavernarakis, N. EMBO Rep. 2002, 3(7), 604-609; Martin, L. J., Al-Abdulla, N. A.; Brambrink, A. M.; Kirsch, J. R.; Sieber, F. E.; Portera-Cailliau, C. Brain Res. Bull. 1998, 46(4), 281-309). Also, cell lyses typically are accompanied by an inflammatory response. Some of the underlying biochemical events in this process are now understood, and the activity of receptor interacting protein kinase 1 (RIP1 kinase) has been shown to be important for cells to undergo necroptosis. Furthermore, RIP1 kinase activity is also known to promote the release of inflammatory mediators such as TNF alpha from cells which can induce inflammation and also promote further necroptosis (Christofferson, D. E., Li, Y., Hitomi, J., Zhou, W., Upperman, C., Zhu, H., Gerber, S. A., Gygi, S., Yuan, J. Cell Death Dis. 2012, 3, e320). Therefore, identifying and preparing low molecular weight molecules that prevent necrotic cell death and/or inflammation by inhibiting RIP1 kinase or by other mechanisms can provide useful compounds for therapeutic intervention in diseases characterized by necrotic cell death and/or inflammation.

Small molecules inhibitors of cellular necrosis have been investigated. For example, U.S. Pat. No. 7,491,743 ("the '743 patent") and U.S. Patent Publication No. 2012/012,889 describe indole-substituted hydantoin molecules as inhibitors of necrosis. The compounds disclosed in these publications include chiral hydantoin moieties linked to an indole moiety via a methylene bridge. Although various preparations for such compounds have been proposed, each of these preparations suffer from various disadvantages such as achiral products, linear synthetic strategies, long and/or low yielding synthetic routes and/or use of enzymes for resolution of racemic products or reagents. Accordingly, none of the currently available preparation methods are useful for large scale production of the indole-substituted hydantoin compounds.

While progress has been made, there remains a need in the art for improved methods for preparation of inhibitors of cellular necrosis as well as improved compounds for preventing and treating diseases involving cell death and/or inflammation. The present disclosure provides this and related benefits.

BRIEF SUMMARY

Embodiments of the present invention provide compounds which are inhibitors of cellular necrosis. Accordingly, the provided compounds find utility as therapeutics for treatment of various disorders associated with cellular necrosis, such as trauma, ischemia, stroke, myocardial infarction, infection, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, inflammatory bowel disease, kidney disease and others. The present inventors have surprisingly found that compounds of certain embodiments of the invention are more potent inhibitors of cellular necrosis relative to structurally related compounds, including those compounds disclosed in the '743 patent.

Accordingly, in one embodiment, there is provided a compound having the following structure (I):

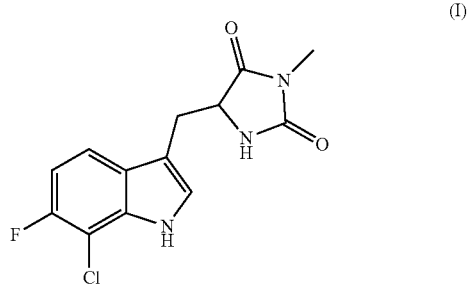 [SMILES: CN1C(=O)NC(Cc2c[nH]c3c(Cl)c(F)ccc23)C1=O]

or a pharmaceutically acceptable salt, prodrug, stereoisomer or tautomer thereof. Pharmaceutical compositions comprising a compound of structure (I), or a pharmaceutically acceptable salt, prodrug, stereoisomer or tautomer thereof, and a pharmaceutically acceptable carrier, diluent or excipient are also provided.

In yet other embodiments, the disclosure is directed to compounds having the following structure (II):

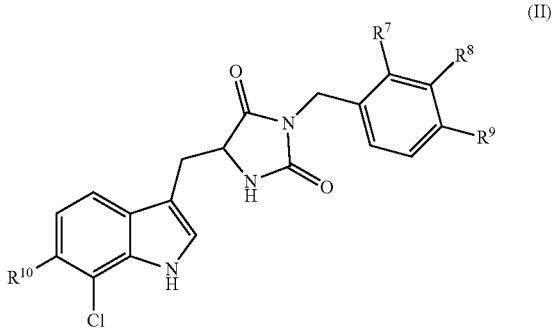

(II)

or a pharmaceutically acceptable salt, prodrug, stereoisomer or tautomer thereof, wherein $R^7$, $R^8$, $R^9$ and $R^{10}$ are as defined herein. Compositions comprising compounds of structure (II) or a pharmaceutically acceptable salt, prodrug or tautomer thereof, and a pharmaceutically acceptable carrier, diluent or excipient are also provided in various other embodiments.

In different embodiments, the present invention provides a compound of structure (I) or (II) for use as a medicament. For example, in some embodiments the invention is directed to a method for treating a necrotic cell disease, the method comprising administering an effective amount of a pharmaceutical composition comprising a compound of structure (I) or (II), or a pharmaceutically acceptable salt, prodrug, stereoisomer or tautomer thereof, to a subject in need thereof. Some different embodiments include use of a compound of structure (I) or (II) for treatment of a necrotic cell disease. Other embodiments include use of a compound of structure (I) or (II) for manufacture of a medicament for treating a necrotic cell disease.

Exemplary necrotic cell diseases which can be treated by the disclosed methods include, but are not limited to, trauma, ischemia, stroke, cardiac infarction, infection, Gaucher's disease, Krabbe disease, sepsis, Parkinson's disease, Alzheimer's disease, amyotrophic lateral sclerosis, Huntington's disease, HIV-associated dementia, retinal degenerative disease, glaucoma, age-related macular degeneration, rheumatoid arthritis, psoriasis, psoriatic arthritis and inflammatory bowel disease.

Still other embodiments are directed to a method for treating an inflammatory disorder, the method comprising administering an effective amount of a pharmaceutical composition comprising a compound of structure (I) or (II), or a pharmaceutically acceptable salt, prodrug, stereoisomer or tautomer thereof, to a subject in need thereof. Some different embodiments are directed to use of a compound of structure (I) or (II) for treatment of an inflammatory disorder. Other different embodiments include use of a compound of structure (I) or (II) for manufacture of a medicament for treating an inflammatory disorder. Exemplary inflammatory disorders include, but are not limited to inflammatory bowel disease.

Embodiments of the present invention provide methods for preparation of hydantoin substituted indole compounds, embodiments of which are inhibitors of cellular necrosis. The provided methods are efficient and amendable to large scale manufacturing of the compounds, as well as smaller scale production for research purposes. Embodiments of the compounds, which can be prepared according to the disclosed method, find utility as therapeutics for treatment of various disorders associated with cellular necrosis, such as trauma, ischemia, stroke, myocardial infarction, infection, sepsis, Parkinson's disease, Alzheimer's disease, amyotrophic lateral sclerosis, Huntington's disease, HIV-associated dementia, retinal degenerative disease, inflammatory bowel disease, kidney disease and others. Accordingly, in one embodiment, there is provided a method for preparing a compound having the following structure (III):

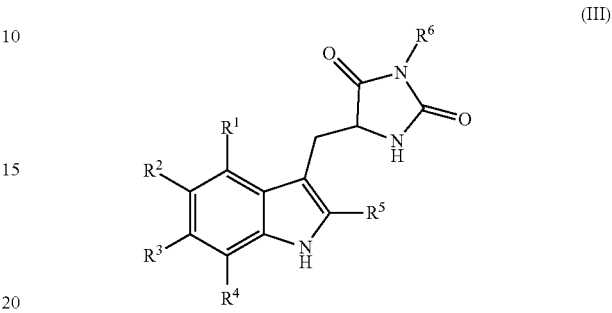

or a pharmaceutically acceptable salt, prodrug, stereoisomer or tautomer thereof, wherein $R^1$, $R^2$, $R^3$, $R^5$, $R^6$ are as defined herein, the method comprising reacting aldehyde (5), or a salt, stereoisomer or tautomer thereof, with phenyl hydrazine (6), or a salt thereof, to yield (7), or a salt, stereoisomer or tautomer thereof, as follows:

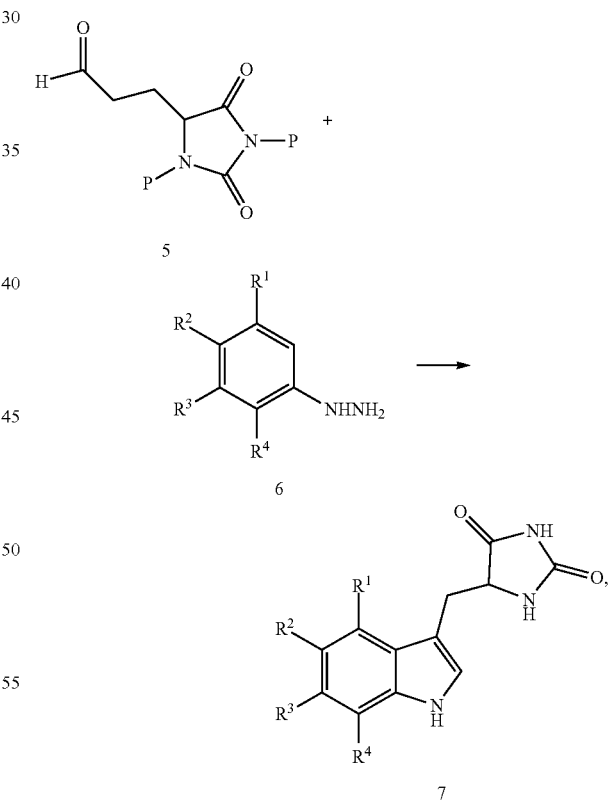

wherein each P is as defined herein.

In other embodiments, the disclosure provides a compound useful for preparation of the indole-substituted hydantoin compounds (e.g., compounds of structure (III)), the compound having one of the following structures (4') or (4"):

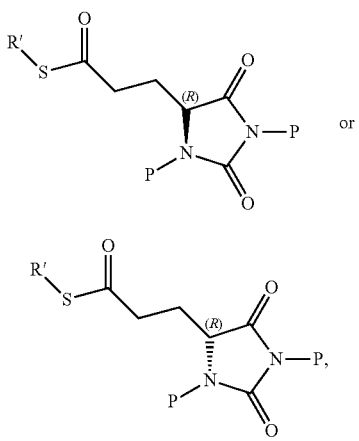

wherein R' and P is as defined herein.

These and other aspects of the invention will be apparent upon reference to the following detailed description. To this end, various references are set forth herein which describe in more detail certain background information, procedures, compounds and/or compositions, and are each hereby incorporated by reference in their entirety.

BRIEF DESCRIPTION OF THE DRAWINGS

In the figures, identical reference numbers identify similar elements. The sizes and relative positions of elements in the figures are not necessarily drawn to scale and some of these elements are arbitrarily enlarged and positioned to improve FIGURE legibility. Further, the particular shapes of the elements as drawn are not intended to convey any information regarding the actual shape of the particular elements, and have been solely selected for ease of recognition in the figures.

FIG. 1 provides RIP1 kinase inhibitory data for a representative compound and a comparative compound.

DETAILED DESCRIPTION

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

"Amino" refers to the —NH$_2$ radical.

"Cyano" refers to the —CN radical.

"Hydroxy" or "hydroxyl" refers to the —OH radical.

"Imino" refers to the =NH substituent.

"Nitro" refers to the —NO$_2$ radical.

"Oxo" refers to the =O substituent.

"Thioxo" refers to the =S substituent.

"Alkyl" refers to a straight or branched hydrocarbon chain radical consisting solely of carbon and hydrogen atoms, which is saturated or unsaturated (i.e., contains one or more double "alkenyl" and/or triple bonds "alkynyl"), having from one to twelve carbon atoms (C$_1$-C$_{12}$ alkyl), preferably one to eight carbon atoms (C$_1$-C$_8$ alkyl) or one to six carbon atoms (C$_1$-C$_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —$R_b$-$R_c$ where $R_b$ is an alkylene chain as defined above and $R_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —$R_bR_d$ where $R_b$ is an alkylene chain as defined above and $R_d$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered aromatic or non-aromatic ring radical which consists of two to twelve carbon atoms and from one to six heteroatoms selected from the group consisting of nitrogen, oxygen and sulfur. Heterocycles include aliphatic heterocycles and aromatic heterocycles (heteroaryls). Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —$R_bR_e$ where $R_b$ is an alkylene chain as defined above and $R_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$ where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a nonhydrogen atoms such as, but not limited to: an alkyl group, a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with $-NR_gR_h$, $-NR_gC(=O)R_h$, $-NR_gC(=O)NR_gR_h$, $-NR_gC(=O)OR_h$, $-NR_gSO_2R_h$, $-OC(=O)NR_gR_h$, $-OR_g$, $-SR_g$, $-SOR_g$, $-SO_2R_g$, $-OSO_2R_g$, $-SO_2OR_g$, $=NSO_2R_g$, and $-SO_2NR_gR_h$. "Substituted" also means any of the above groups in which one or more hydrogen atoms are replaced with $-C(=O)R_g$, $-C(=O)OR_g$, $-C(=O)NR_gR_h$, $-CH_2SO_2R_g$, $-CH_2SO_2NR_gR_h$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. In addition, each of the foregoing substituents may also be optionally substituted with one or more of the above substituents.

The term "leaving group" refers to a molecular fragment that departs with a pair of electrons in heterolytic bond cleavage. Leaving groups can be charged or neutral molecules. "Leaving groups" include, but are not limited to, halides such as $Cl^-$, $Br^-$, $I^-$, sulfonate esters (e.g., $TsO^-$), water and ammonia.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass all pharmaceutically acceptable compounds of structure (I) being isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine, chlorine, and iodine, such as $^2H$, $^3H$, $^{11}C$, $^{13}C$, $^{14}C$, $^{13}N$, $^{15}N$, $^{15}O$, $^{17}O$, $^{18}O$, $^{31}P$, $^{32}P$, $^{35}S$, $^{18}F$, $^{36}Cl$, $^{123}I$, and $^{125}I$, respectively. These radiolabeled compounds could be useful to help determine or measure the effectiveness of the compounds, by characterizing, for example, the site or mode of action, or binding affinity to pharmacologically important site of action.

Certain isotopically-labelled compounds of structure (I), for example, those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances.

Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labeled compounds of structure (I) can generally be prepared by conventional techniques known to those skilled in the art or by processes analogous to those described in the Preparations and Examples as set out below using an appropriate isotopically-labeled reagent in place of the non-labeled reagent previously employed.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabeled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

"Treating" or "treatment" as used herein covers the treatment of the disease or condition of interest in a mammal (e.g., conditions associated with cellular necrosis), preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts include an asymmetric center and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

The term "necrotic cell disease" refers to diseases associated with or caused by cellular necrosis. Exemplary necrotic cell diseases include, but are not limited to, acute diseases such as trauma, ischemia, stroke, cardiac infarction, anthrax lethal toxin induced septic shock, sepsis, cell death induced by LPS, and HIV induced T-cell death leading to immunodeficiency. The term "necrotic cell disease" also includes but is not limited to chronic neurodegenerative diseases, such as Parkinson's disease, Huntington's disease, amyotrophic lateral sclerosis, Alzheimer's disease, infectious encelopathies, dementia such as HIV associated dementia. The term "necrotic cell disease" also includes but is not limited to diseases such as inflammatory bowel disease and acute and chronic kidney disease which are characterized by inflammation and cell death.

The term "$ED_{50}$" means the dose of a drug that produces 50% of its maximum response or effect. Alternatively, "$ED_{50}$" means the dose that produces a pre-determined response in 50% of test subjects or preparations.

The term "$LD_{50}$" means the dose of a drug that is lethal in 50% of test subjects.

The term "$EC_{50}$" means the concentration of a drug that produces 50% of its maximum response or effect in a test assay. Alternatively, "$EC_{50}$" means the effective concentration that produces a pre-determined response in 50% of test assays.

The term "therapeutic index" refers to the therapeutic index of a drug defined as $LD_{50}/ED_{50}$.

The chemical names used herein are generated using the ChemDraw Ultra Version 11.0 software naming program (CambridgeSoft).

I. Compounds

Compounds of Structure (I)

As noted above, certain embodiments of the present disclosure are directed to a compound having the following structure (I):

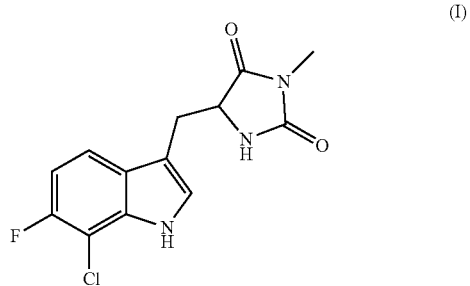 [SMILES: CN1C(=O)NC(Cc2c[nH]c3c(Cl)c(F)ccc23)C1=O]

or a pharmaceutically acceptable salt, prodrug, stereoisomer or tautomer thereof.

Compounds of structure (I) in enantiomerically enriched or enantiomerically pure form are also provided. Accordingly, in some embodiments the compound has the following structure (Ia):

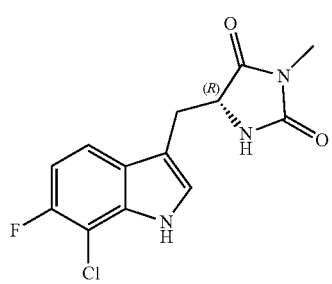
(Ia)

or a pharmaceutically acceptable salt, prodrug or tautomer thereof.

In other embodiments, the compound has the following structure (Ib):

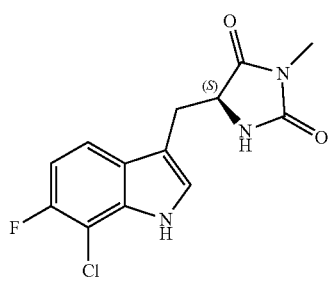
(Ib)

or a pharmaceutically acceptable salt, prodrug or tautomer thereof.

In some embodiments, compound (I), (Ia) or (Ib) is provided in the form of a pharmaceutically acceptable salt. Exemplary salts for this purpose are described herein.

In some other embodiments, the invention provides a prodrug which converts to compound (I), (Ia) or (Ib) in vivo. Exemplary prodrugs for this purpose are known in the art and described herein.

The following General Reaction Schemes I and II illustrate exemplary methods of making compounds of structure (I):

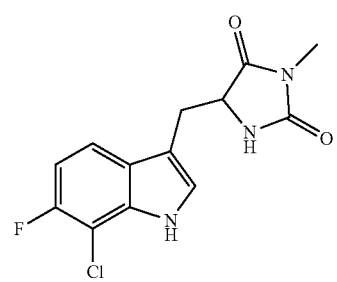
(I)

Other methods for preparing compounds of structure (I) are provided herein below and in the Examples (e.g., Example 1). It is understood that one skilled in the art may be able to make these compounds by similar methods or by combining other methods known to one skilled in the art. In general, starting components and reagents may be obtained from sources such as Sigma Aldrich, Lancaster Synthesis, Inc., Maybridge, Matrix Scientific, TCI, and Fluorochem USA, etc. or synthesized according to sources known to those skilled in the art (see, for example, Advanced Organic Chemistry: Reactions, Mechanisms, and Structure, 5th edition (Wiley, December 2000)) or prepared as described in this invention.

For example, compounds of structure (I) may be prepared with reference to the following General Reaction Scheme I:

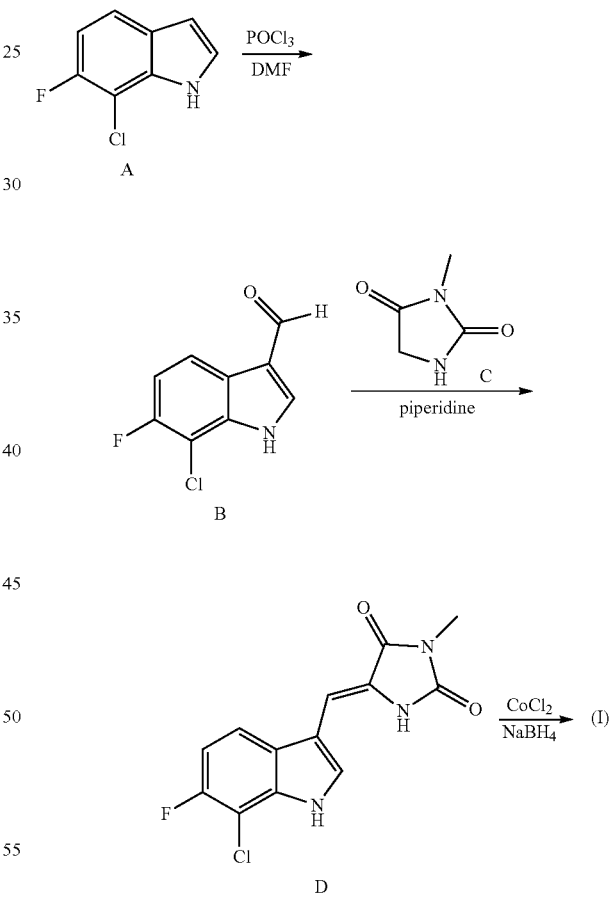

General Reaction Scheme I

Referring to General Reaction Scheme 1, indole A is treated with POCl₃ to obtain aldol B. Reductive alkylation of B and C results in compound D, which is then reduced to yield compounds of structure (I).

When enantiomerically pure or enriched compounds are desired, the compounds can be prepared according to General Reaction Scheme II.

General Reaction Scheme II

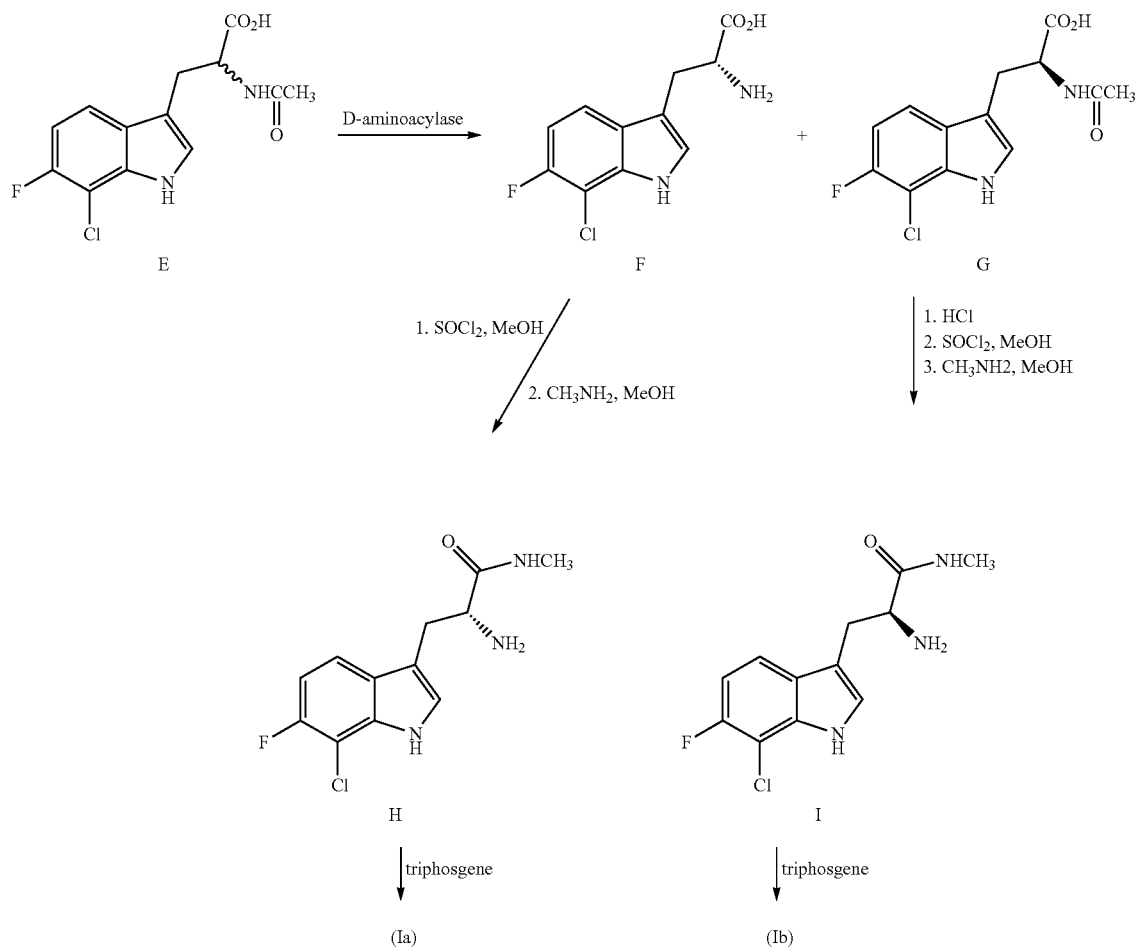

Referring to General Reaction Scheme II, appropriately substituted N-acetyl DL tryptophan E is treated with D-aminoacylase to remove the acetyl group from the D tryptophan moiety. Compounds F and G are then separated and treated in parallel reaction pathways. Compound F is methylated in the presence of thionyl chloride and the resulting compound is converted to the methyl amide H. Treatment of H with triphosgene results in compound (Ia).

In a separate reaction pathway, the N-acetyl group of compound G is first removed by treatment with HCl. Conditions similar to those described for conversion of F to (Ia) are then employed to prepare (Ib). It will be apparent to one of ordinary skill in the art that an analogous method, which employs L-aminoacylase may also be employed.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P.G.M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of structure (I) which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

Compounds of Structure (II)

In other embodiments, the invention is directed to compounds having the following structure (II):

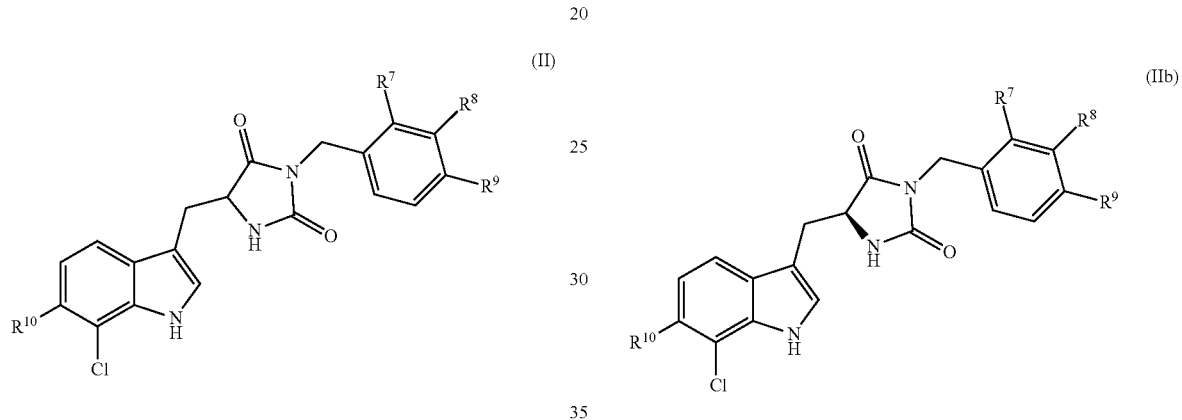

or a pharmaceutically acceptable salt, prodrug, stereoisomer or tautomer thereof, wherein one or two of $R^7$, $R^8$ or $R^9$ is F, and each remaining $R^7$, $R^8$ or $R^9$ is H; and $R^{10}$ is H or F.

In some embodiments, the compound has the following structure (IIa):

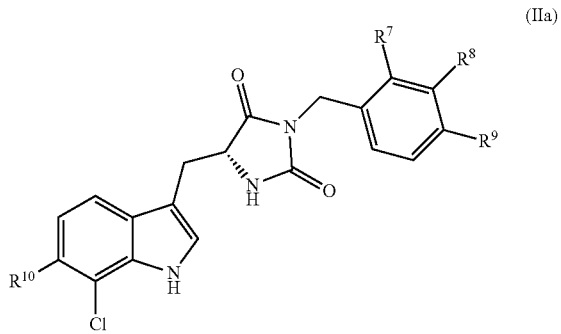

In some embodiments, the compound has the following structure (IIb):

In some embodiments of structure (II), $R^{10}$ H. In other embodiments, $R^{10}$ F.

In some other embodiments $R^7$ is F. In different embodiments $R^8$ is F. In yet other embodiments, $R^9$ is F.

In some more specific embodiments, $R^7$ and $R^8$ are F. In some other specific embodiments, $R^8$ and $R^9$ are F.

In various other embodiments, the compound of structure (II) has one of the structures provided in Table 1.

TABLE 1

| | Exemplary Compounds of structure (II) | |
|---|---|---|
| No. | Structure | Name |
| II-1 | | 5-((7-chloro-1H-indol-3-yl)methyl)-3-(2-fluorobenzyl)imidazolidine-2,4-dione |

TABLE 1-continued

Exemplary Compounds of structure (II)

| No. | Structure | Name |
|---|---|---|
| II-2 | 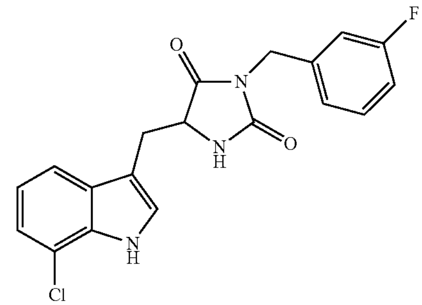 [SMILES: O=C1NC(Cc2c[nH]c3c(Cl)cccc23)C(=O)N1Cc1cccc(F)c1] | 5-((7-chloro-1H-indol-3-yl)methyl)-3-(3-fluorobenzyl)imidazolidine-2,4-dione |
| II-3 | 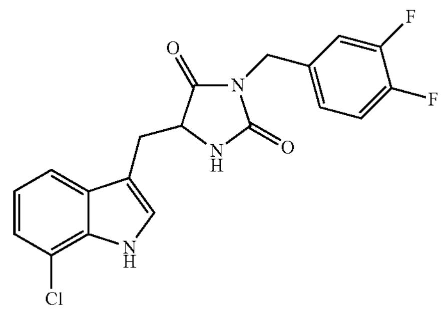 [SMILES: O=C1NC(Cc2c[nH]c3c(Cl)cccc23)C(=O)N1Cc1ccc(F)c(F)c1] | 5-((7-chloro-1H-indol-3-yl)methyl)-3-(3,4-difluorobenzyl)imidazolidine-2,4-dione |
| II-4 | 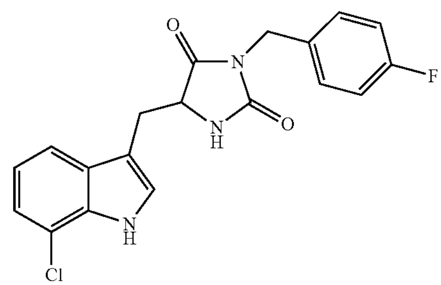 [SMILES: O=C1NC(Cc2c[nH]c3c(Cl)cccc23)C(=O)N1Cc1ccc(F)cc1] | 5-((7-chloro-1H-indol-3-yl)methyl)-3-(4-fluorobenzyl)imidazolidine-2,4-dione |
| II-5 | 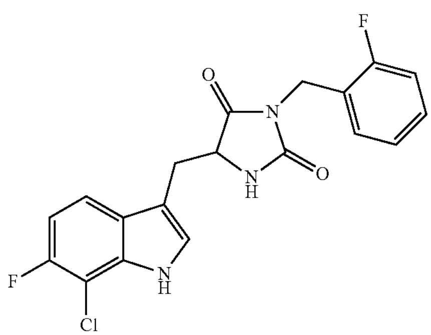 [SMILES: O=C1NC(Cc2c[nH]c3c(Cl)c(F)ccc23)C(=O)N1Cc1ccccc1F] | 5-((7-chloro-6-fluoro-1H-indol-3-yl)methyl)-3-(2-fluorobenzyl)imidazolidine-2,4-dione |
| II-6 | 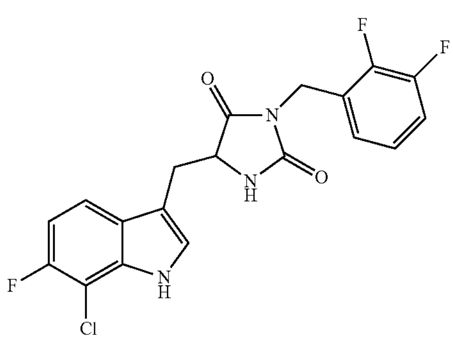 [SMILES: O=C1NC(Cc2c[nH]c3c(Cl)c(F)ccc23)C(=O)N1Cc1cccc(F)c1F] | 5-((7-chloro-6-fluoro-1H-indol-3-yl)methyl)-3-(2,3-difluorobenzyl)imidazolidine-2,4-dione |

TABLE 1-continued

Exemplary Compounds of structure (II)

| No. | Structure | Name |
|---|---|---|
| II-7 | 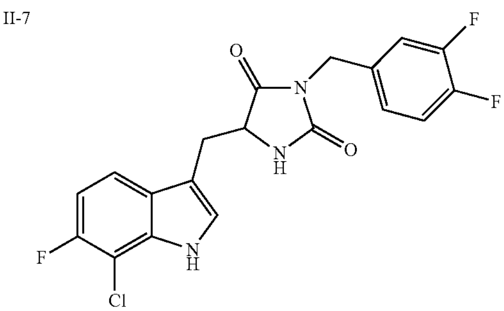 | 5-((7-chloro-6-fluoro-1H-indol-3-yl)methyl)-3-(3,4-difluorobenzyl)imidazolidine-2,4-dione |

Enantiomerically pure or enriched compounds of the compounds in Table 1, including those exemplified in the Examples which follow, are also provided As described in more detail in the Examples, the compounds of structure (II), such as those compounds illustrated in Table 1, were found to be surprisingly more potent inhibitors of necrosis relative to a structurally related compound disclosed in U.S. Patent Publication No. 2012/0122889, which is hereby incorporated by reference in its entirety with respect to small-molecule inhibitors of necrosis. Compounds of structure (II) may be prepared according to the procedures described herein below and in the Examples which follow.

II. Compositions

For the purposes of administration, the compounds of the present invention may be administered as a raw chemical or may be formulated as pharmaceutical compositions. Pharmaceutical compositions of the present invention comprise a compound of structure (I) or (II) and a pharmaceutically acceptable carrier, diluent or excipient. Accordingly, different embodiments are directed to pharmaceutical compositions comprising any one or more of the foregoing compounds (e.g., compounds of structure (I) or (II)) or a pharmaceutically acceptable salt, prodrug, stereoisomer or tautomer thereof, and a pharmaceutically acceptable carrier, diluent or excipient are also provided in various embodiments.

The pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; surfactants, such as polysorbate 80 (i.e. Tween 80); powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations. Examples of such formulations include, but are not limited to DMSO, 10 mM DMSO, 8% hydroxypropyl-beta-cyclodextrin in PBS, propylene glycol, etc. For example, in a certain embodiment the compounds of the invention can be used as 4 mM solution in 8% hydroxypropyl-beta-cyclodextrin in PBS for parenteral administration. In another certain embodiment, the compounds of the invention can be used as a suspension in 0.5% aqueous CMC containing 0.1% TWEEN 80.

As set out herein, certain embodiments of the present compounds may contain a basic functional group, such as amino or methylamino ($NCH_3$), and are, thus, capable of forming pharmaceutically-acceptable salts with pharmaceutically-acceptable acids. The term "pharmaceutically-acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenyl sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

III. Treatment Methods

In some embodiments, the present invention provides a compound of structure (I) or (II) for use as a medicament. For example, in one aspect the present invention relates to a method of treating a disease associated with cellular necrosis. In particular, one embodiment of the invention provides methods for preventing or treating a disorder associated with cellular necrosis (i.e., a necrotic cell disease) in a mammal, comprising the step of administering to said mammal a therapeutically effective amount of a compound (e.g., compound of structure (I) or (II)) or therapeutic preparation of the present invention. Some other embodiments include use of a compound of structure (I) or (II) for treatment of a necrotic cell disease. Other embodiments include use of a compound of structure (I) or (II) for manufacture of a medicament for treating a necrotic cell disease.

In certain embodiments, the disorder associated with cellular necrosis is a disorder such as trauma, ischemia, stroke, cardiac infarction, infection and/or sepsis. In certain embodiments, the disorder associated with cellular necrosis is a disorder such as trauma, ischemia, stroke, cardiac infarction, infection, Gaucher's disease, Krabbe disease and/or sepsis. In other embodiments, the disorder is a neurodegenerative disease, such as Parkinson's disease (PD), Alzheimer's disease (AD), amyotrophic lateral sclerosis (ALS), Huntington's disease (HD), and HIV-associated dementia (HAD). In other embodiments the disorder is an ischemic disease of organs including but not limited to brain, heart, kidney, and liver. In some different embodiments, the disorder is an ocular disorder such as retinal degenerative disease, glaucoma or age-related macular degeneration. In some different embodiments, the disorder is an autoimmune disorder such as rheumatoid arthritis, psoriasis or psoriatic arthritis. In some different embodiments, the disorder is a central nervous system (CNS) disorder.

In other embodiments the presently disclosed compounds (e.g., compounds of structure (I) or (II)) are used in methods for treatment of inflammatory disorders. Some other embodiments are directed to use of a compound of structure (I) or (II) for treatment of an inflammatory disorder. Other different embodiments include use of a compound of structure (I) or (II) for manufacture of a medicament for treating an inflammatory disorder. In some embodiments, the disorder is an inflammatory disease of the intestines such as Crohn's disease or ulcerative colitis (both generally known together as inflammatory bowel disease).

In certain embodiments, the mammal is a primate, canine or feline subject. In other embodiments, the mammal is a human subject. While not wishing to be bound by theory, it is believed that inhibition of RIP1 kinase by the presently disclosed compounds is responsible, at least in part, for their anti-inflammatory activity. Accordingly, embodiments of the invention also include methods for inhibiting RIP1 kinase, either in vitro or in a subject in need thereof, the method comprises contacting a RIP1 kinase with a compound disclosed herein (e.g. compounds of structure (I) or (II)). In some of these embodiments, inhibiting RIP1 kinase is effective to block (partially or fully) the release of inflammatory mediators such as TNF and/or IL6.

The compounds of structure (I) and/or (II) can be used to treat ocular indications, for example to reduce or prevent the loss of photoreceptor and/or retinal pigment epithelial cell viability. In one aspect, the invention provides a method of preserving the visual function of an eye of a subject with an ocular condition, wherein a symptom of the ocular condition is the loss of photoreceptor cell viability in the retina of the eye with the condition. The method comprises administering to the eye of the subject an effective amount of a compound of structure (I) and/or (II) thereby preserving the viability of the photoreceptor cells disposed within the retina of the eye. After administration of the compound of structure (I) and/or (II) the visual function (e.g., visual acuity) of the eye may be preserved or improved relative to the visual function of the eye prior to administration of the compound of structure (I) and/or (II).

The ocular condition may be a condition selected from the group consisting of age-related macular degeneration (AMD), retinosis pigmentosa (RP), macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. AMD may be the neovascular or the dry form of AMD. Retinal detachment may be a rhegmatogenous, a serous, or a tractional retinal detachment.

In another aspect, the invention provides a method of preserving the viability of retinal pigment epithelial (RPE) cells within the retina of a subject with an ocular condition, wherein a symptom of the ocular condition is the loss of retinal pigment epithelial cells in the retina of the eye with the condition. The method comprises administering to the eye of the subject an effective amount of a compound of structure (I) and/or (II) thereby preserving the viability of the retinal pigment epithelial cells. The ocular condition may be selected from the group consisting of AMD, BEST disease, myopic degeneration, Stargardt's disease, uveitis, adult foveomacular dystrophy, fundus falvimaculatus, multiple evanescent white dot syndrome, serpiginous choroidopathy, acute multifocal posterior placoid epitheliopathy (AMPPE), and other uveitis disorders.

In another aspect, the invention provides a method of preserving the viability of photoreceptor cells disposed within a retina of a subject with an ocular condition selected from the group consisting of AMD, RP, macular edema, diabetic retinopathy, central areolar choroidal dystrophy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity. The method comprises administering to the eye an effective amount of a compound of structure (I) and/or (II) thereby to preserve the viability of the photoreceptor cells disposed within the retina of the subject with a condition.

In another aspect, the invention provides a method of preserving the viability of photoreceptor cells disposed within a retina of a mammalian eye following retinal detachment. The method comprises administering a compound of structure (I) and/or (II) to the eye in which a region of the retina has been detached in amounts sufficient to preserve the viability of photoreceptor cells disposed within the region of the detached retina.

In certain embodiments, the retinal detachment may be a rhegmatogenous retinal detachment, tractional retinal detachment, or serous retinal detachment. In other embodiments, the retinal detachment may occur as a result of a retinal tear, retinoblastoma, melanoma or other cancers, diabetic retinopathy, uveitis, choroidal neovascularization, retinal ischemia, pathologic myopia, or trauma.

In another aspect, the invention provides a method of preserving visual function of an eye of a subject with an ocular condition selected from the group consisting of AMD, RP, macular edema, central areolar choroidal dystrophy, retinal detachment, diabetic retinopathy, BEST disease, adult vitelliform disease, pattern dystrophy, myopic degeneration, central serous retinopathy, Stargardt's disease, Cone-Rod dystrophy, North Carolina dystrophy, infectious retinitis, inflammatory retinitis, uveitis, toxic retinitis and light-induced toxicity, wherein a symptom of the ocular condition is the loss of photoreceptor cells viability in the retina of the eye. The method comprises administering an effective amount of a compound of structure (I) and/or (II) to the patient.

In another aspect, the invention provides a method of preserving the visual function of an eye of a subject with an ocular condition, wherein a symptom of the ocular condition is the loss of photoreceptor cell viability and/or RPE viability in the retina of the eye. The method comprises treating the subject with a compound of structure (I) and/or (II); and (b), after treatment, measuring visual function (e.g., visual acuity) of the eye.

In other embodiments is provided a method of preserving the visual function of an eye of a subject with ocular conditions, wherein a symptom of the ocular condition is the loss of retinal ganglion cell viability in the retina of the eye with the conditions. The method comprises administering to the eye of the subject an effective amount of a compound of structure (I) and/or (II) thereby preserving the viability of the retinal ganglion cells disposed within the retina of the eye. After administration of the compound of structure (I) and/or (II) the visual function of the eye may be preserved or improved relative to the visual function of the eye prior to administration of the compound of structure (I) and/or (II). Further, after the administration of the compound of structure (I) and/or (II), the preserved retinal ganglion cell is capable of supporting axonal regeneration.

In each of the foregoing methods, the ocular condition, wherein a symptom of the condition is the loss of retinal ganglion cell viability in the retina of the eye, includes but is not limited to glaucoma, optic nerve injury, optic neuritis, optic neuropathies, diabetic retinopathy, central retinal artery occlusion, and central retinal vein occlusion. It is contemplated that the forgoing methods may be used for the treatment of optic neuropathies such as ischemic optic neuropathy (e.g., arteritic or non-arteritic anterior ischemic neuropathy and posterior ischemic optic neuropathy), compressive optic neuropathy, infiltrative optic neuropathy, traumatic optic neuropathy, mitochondrial optic neuropathy (e.g., Leber's optic neuropathy), nutritional optic neuropathy, toxic optic neuropathy, and hereditary optic neuropathy (e.g., Leber's optic neuropathy, Dominant Optic Atrophy, Behr's syndrome).

Also disclosed is a method of preserving the visual function of an eye of a subject with an ocular condition selected from the group consisting of glaucoma, optic nerve injury, optic neuropathies, diabetic retinopathy, central retinal artery occlusion, and central retinal vein occlusion. The method comprises administering to the eye of the subject an effective amount of a compound of structure (I) and/or (II) thereby preserving the viability of the retinal ganglion cells disposed within the retina of the eye and the visual function of the eye.

In another aspect, disclosed herein is a method of preserving the viability of retinal ganglion cells disposed within a retina of a mammalian eye affected by, for example, glaucoma, optic nerve injury, optic neuritis, optic neuropathies, diabetic retinopathy, central retinal artery occlusion, and central retinal vein occlusion. The method comprises administering a compound of structure (I) and/or (II) to the eye in which a region of the retina has been affected in amounts sufficient to preserve the viability of retinal ganglion cells disposed within the region of the affected retina. The preserved retinal ganglion cell is capable of supporting axonal regeneration.

Also disclosed is a method for promoting axon regeneration in an eye of a subject with an ocular condition, wherein a symptom of the ocular condition is the loss of retinal ganglion cell viability in the retina of the eye with the condition. The method comprises administering to the eye of the subject an effective amount of a compound of structure (I) and/or (II) thereby promoting axon regeneration of the retinal ganglion cell within the retina of the eye.

In each of the foregoing embodiments, it is understood that the methods and compositions described herein can be used to preserve the viability and/or promote axon regeneration of retinal ganglion cells during treatment of the underlying conditions including, but not limited to, glaucoma, optic nerve injury, optic neuritis, optic neuropathies, diabetic retinopathy, central retinal artery occlusion, and central retinal vein occlusion.

In another embodiment, the compound of structure (I) and/or (II) can be used to preserve neuron viability and promote axon growth and nerve functions. Accordingly, the compound of structure (I) and/or (II) may be used to reduce or even reverse the loss of cognitive, motor, and sensory functions associated with a CNS disorder, by preserving neuron viability and/or promoting axon regeneration and/or nerve functions.

In one aspect, the invention provides a method for promoting axon regeneration in a CNS neuron by exposing the CNS neuron to an effective amount of a compound of structure (I) and/or (II). The CNS neuron may be ex vivo or in vivo. The CNS neuron may include, but is not limited to, a CNS sensory neuron, a motor neuron, a cortical neuron, a cerebellar neuron, a hippocampal neuron, and a midbrain neuron.

In another aspect, the invention provides a method for promoting nerve function following injury to a CNS neuron. The method comprises administering to a subject an effective amount of a compound of structure (I) and/or (II) thereby to promote CNS neuron function. In a further aspect, the invention provides a method for preserving the viability of a CNS neuron, wherein the method comprises administering to a subject an effective amount of a compound of structure (I) and/or (II) thereby to preserve the viability of the CNS neuron. After administration of the compound of structure (I) and/or (II), the CNS neuron may be capable of supporting axonal regeneration.

In another aspect, the invention provides a method of treating a CNS disorder in a subject in need thereof, wherein a symptom of the CNS disorder is axon degeneration or injury within a CNS neuron. The method comprises administering to the subject an effective amount of a compound of structure (I) and/or (II) thereby to promote regeneration of an axon in a CNS neuron affected by the CNS disorder. Following administration of the compound of structure (I) and/or (II), neural functions may be measured, for example, as an indication of axon regeneration. It is also contemplated that, following administration of the compound of structure (I) and/or (II), the neuron function of the CNS neuron is preserved or improved relative to the neuron function prior to administration of the compound of structure (I) and/or (II). The CNS disorder includes, but is not limited to, brain injury, spinal cord injury, dementia, stroke, Alzheimer's disease, amyotrophic lateral sclerosis (ALS/Lou Gehrig's Disease), Parkinson's disease, Huntington's disease, multiple sclerosis, diabetic neuropathy, polyglutamine (polyQ) diseases, stroke, Fahr disease, Menke's disease, Wilson's disease, cerebral ischemia, and a prion disorder. In exemplary embodiments, the CNS disorder is brain injury or spinal cord injury.

Also provided herein are methods for promoting neuron survival and axon regeneration in the CNS. CNS disorders characterized by impaired or failing axon growth or axon degeneration may arise from CNS neuron injury (e.g., trauma, surgery, nerve compression, nerve contusion, nerve transection, neurotoxicity, or other physical injury to the brain or spinal cord) or neurodegenerative CNS disease, wherein a symptom of the disorder is axon degeneration (e.g., Alzheimer's disease, amyotrophic lateral sclerosis (ALS/Lou Gehrig's Disease), Parkinson's disease, multiple sclerosis, diabetic neuropathy, polyglutamine (polyQ) diseases, and stroke, Fahr disease, Menke's disease, Wilson's disease, cerebral ischemia, prion disorder (e.g., Creutzfeldt-Jakob disease). In an exemplary embodiment, the CNS disorder is brain injury (e.g., traumatic brain injury) or spinal cord injury (e.g., chronic, acute, or traumatic spinal cord injury). In another embodiment, the CNS disorder affects a subject's basic vital life functions such as breathing, heart beat and blood pressure, e.g., an injury to or aneurysm in the brain stem.

In certain embodiments, the CNS disorder affects a subject's cognitive ability, such as, brain injury to the cerebral cortex or a neurodegenerative CNS disorder, such as, Alzheimer's disease, frontotemporal dementia, dementia with Lewy bodies, corticobasal degeneration, progressive supranuclear palsy, and prion disorders.

In other embodiments, the CNS disorder affects a subject's movement and/or strength, such as injury to the brain or spinal cord, or a neurodegenerative CNS disorder such as Parkinson's disease, frontotemporal dementia, dementia with Lewy bodies, corticobasal degeneration, progress supranuclear palsy, Huntington's disease, multiple system atrophy, amyotrophic lateral sclerosis, and hereditary spastic paresis.

In yet another embodiment, the CNS disorder affects a subject's coordination, such as brain injury to the cerebellum or a neurodegenerative CNS disorder such as spinocerebellar atrophies, Friedreich's ataxia, and prion disorders.

In each of the foregoing methods, the CNS disorder includes, but is not limited to, brain injury, spinal cord injury, Alzheimer's disease, amyotrophic lateral sclerosis (ALS/Lou Gehrig's Disease), Parkinson's disease, multiple sclerosis, diabetic neuropathy, polyglutamine (polyQ) diseases, stroke, Fahr disease, Menke's disease, Wilson's disease, cerebral ischemia, a prion disorder (e.g., Creutzfeldt-Jakob disease), dementia (e.g., frontotemporal dementia, dementia with Lewy bodies), corticobasal degeneration, progressive supranuclear palsy, multiple system atrophy, hereditary spastic paraparesis, and spinocerebellar atrophies.

It is understood that embodiments of the present invention include use of a compound of structure (I) or (II) for treatment of any of the foregoing indications. Other embodiments include use of a compound of structure (I) or (II) for manufacture of medicament for treatment of any of the foregoing indications.

The term "trauma" as used herein refers to any physical damage to the body caused by violence, accident, fracture etc. The term "ischemia" refers to a cardiovascular disorder characterized by a low oxygen state usually due to the obstruction of the arterial blood supply or inadequate blood flow leading to hypoxia in the tissue. The term "stroke" refers to cardiovascular disorders caused by a blood clot or bleeding in the brain, most commonly caused by an interruption in the flow of blood in the brain as from clot blocking a blood vessel, and in certain embodiments of the invention the term stroke refers to ischemic stroke or hemorrhagic stroke. The term "myocardial infarction" refers to a cardiovascular disorder characterized by localized necrosis resulting from obstruction of the blood supply.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. A therapeutically effective amount for treating a neurological disorder is an amount sufficient to inhibit necrosis in at least a subset of cells that were exposed to a cell-death initiating event. Accordingly, a therapeutically effective amount prevents or minimizes disease progression associated with cellular necrosis. Disease progression can be monitored relative to an expected disease progression that is based on population studies, controlled observations in individuals, or a combination of both.

In certain embodiments, a compound or pharmaceutical preparation is administered orally. In other embodiments, the compound or pharmaceutical preparation is administered intravenously. Alternative routes of administration include sublingual, intramuscular, and transdermal administrations.

In certain embodiments, the present invention relates to compounds for inhibiting cell death, wherein the compounds are represented by structures (I) or (II). In certain embodiments, the compounds of the present invention are inhibitors of cell death. In any event, the compounds of the present invention preferably exert their effect on inhibiting cell death at a concentration less than about 50 micromolar, more preferably at a concentration less than about 10 micromolar, and most preferably at a concentration less than 1 micromolar.

The compounds of the invention can be tested in standard animal models of stroke and standard protocols such as described by Hara, H., et al. Proc Natl Acad Sci USA, 1997. 94(5): 2007-12.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc.

administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts. A daily, weekly, or monthly dosage (or other time interval) can be used.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In general, a suitable daily dose of a compound of the invention will be that amount of the compound that is the lowest dose effective to produce a therapeutic effect (e.g., inhibit necrosis). Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight.

If desired, the effective daily dose of the active compound may be administered as two, three, four, five, six or more sub-doses administered separately at appropriate intervals throughout the day, optionally, in unit dosage forms.

In another aspect of the invention the compounds can be administered in combination with other agents, including (but not limited to) compounds that are apoptosis inhibitors; PARP poly(ADP-ribose) polymerase inhibitors; Src inhibitors; agents for the treatment of cardiovascular disorders; anti-inflammatory agents, anti-thrombotic agents; fibrinolytic agents; anti-platelet agents, lipid reducing agents, direct thrombin inhibitors; glycoprotein IIb/IIIa receptor inhibitors; calcium channel blockers; beta-adrenergic receptor blocking agents; cyclooxygenase (e.g., COX-1 and COX-2) inhibitors; angiotensin system inhibitor (e.g., angiotensin-converting enzyme (ACE) inhibitors); renin inhibitors; and/or agents that bind to cellular adhesion molecules and inhibit the ability of white blood cells to attach to such molecules (e.g., polypeptides, polyclonal and monoclonal antibodies). Suitable combination agents in this regard are also disclosed in U.S. Pat. No. 7,491,743, and which is hereby incorporated by reference in its entirety for all that it discloses.

Embodiments of the invention also provide combinations of two or more compounds that inhibit cellular necrosis (e.g., a compound as disclosed herein and an additional agent for inhibiting necrosis). The invention also provides combinations of one or more compounds that inhibit cellular necrosis combined with one or more additional agents or compounds (e.g., other therapeutic compounds for treating a disease, condition, or infection such as an apoptosis inhibitor).

The invention also provides kits including one or more compounds or combinations of the invention. A kit can also include one or more additional agents or compounds described herein. The different components of the kit can be provided in different containers. The kit can be compartmentalized to receive the containers in close confinement. The kit can also contain instructions for using the compounds according to the invention.

As used herein, a kit such as a compartmentalized kit includes any kit in which compounds or agents are contained in separate containers. Illustrative examples of such containers include, but are not limited to, small glass containers, plastic containers or strips of plastic or paper. Particularly preferred types of containers allow the skilled worker to efficiently transfer reagents from one compartment to another compartment such that the samples and reagents are not cross-contaminated and the agents or solutions of each container can be added in a quantitative fashion from one compartment to another. Such containers include, but are not limited to, a container that will accept a compound or combination of compounds and/or other agents of the invention. One or more compounds or agents can be provided as a powder (e.g. lyophilized powder) or precipitate. Such compound(s) can be resuspended prior to administration in a solution that may be provided as part of the kit or separately available. A kit can contain compounds or agents in other forms such as liquids, gels, solids, as described herein. Different compounds and/or agents may be provided in different forms in a single kit.

The examples and preparations provided below further illustrate and exemplify the compounds of the present invention and methods for testing such compounds. It is to be understood that the scope of the present invention is not limited in any way by the scope of the following examples. In the following examples, and throughout the specification and claims, molecules with a chiral center, unless otherwise noted, exist as a racemic mixture. Single enantiomers may be obtained by methods known to those skilled in the art.

IV. Synthetic Methods

In other embodiments, the present disclosure provides improved methods for preparation of indole-hydantoin compounds, which in some embodiments are potent inhibitors of necrosis. Although other syntheses of related compounds have been proposed, none of these earlier methods is sufficiently robust for large-scale manufacturing or for preparation and screening of numerous diverse analogs. Specifically, U.S. Pat. No. 7,491,743, which is hereby incorporated by reference in its entirety, provides three synthetic routes for these compounds. In the first of these routes, which is illustrated in Comparative Reaction Scheme 1a, an indole-3-carboxaldehyde fragment is connected to a hydantoin fragments by aldol reaction (Scheme 1a, step c). The target product is then obtained by hydrogenation/reduction (Scheme 1a, step d). Among the disadvantages of this method are that the obtained target product is achiral, and the substituted indole must be prepared via various different routes depending on the desired substitution.

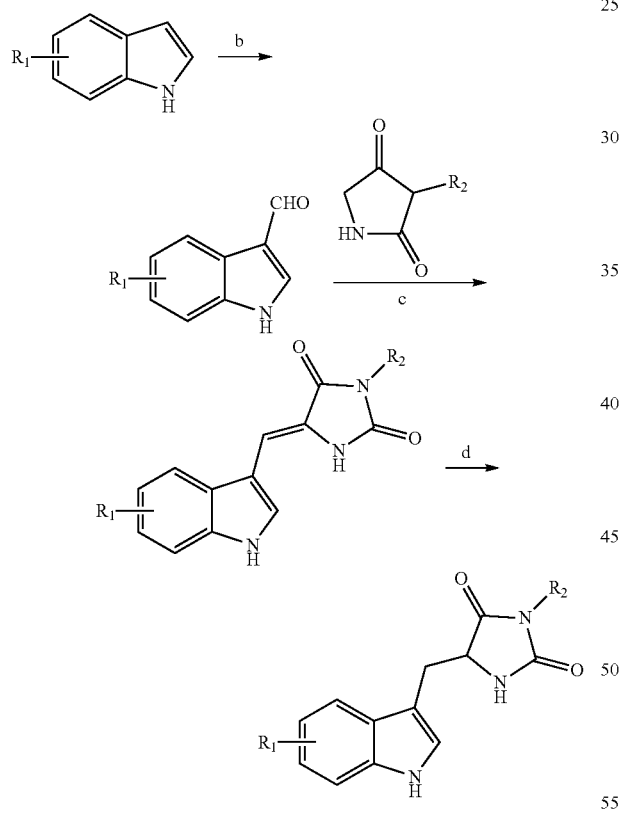

A second approach to preparation of the indole-hydantoin compounds described in U.S. Pat. No. 7,491,743 is illustrated in Comparative Reaction Scheme 2. In this scheme, the aldehyde was obtain by reduction, iodination, cyano-substitution and cyano-reduction. The target product was then obtained by cyclization in the presence of ammonium carbonate and potassium cyanide, followed by alkylation. Because of the achiral products, linear synthetic strategy and toxicities of the potassium cyanide, this route is also not conductive to divergent synthesis methods and large-scale production.

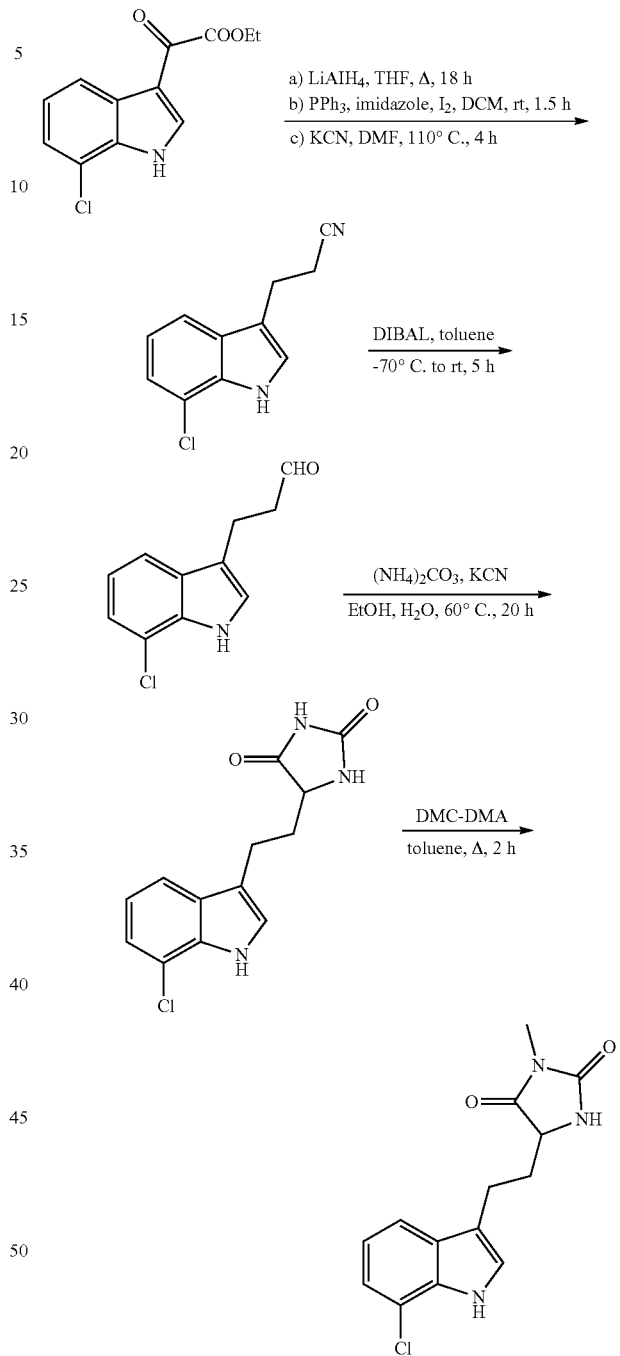

Comparative Reaction Scheme 3 illustrates the third method described in U.S. Pat. No. 7,491,743. In this approach, the N-acetyl tryptophan derivatives were obtained by mixing indoles with serine in acetic acid and acetic anhydride. The target product was then obtained by kinetic resolution, methylation, amination and finally reaction with triphosgene. Although this method does provide chiral products, it is inefficient due to the long synthetic route and low reaction yields (the reaction with serine only yield 40% product and cyclization by triphosgene yield 34%), and also requires use of enzymes to obtain the desired chiral purity.

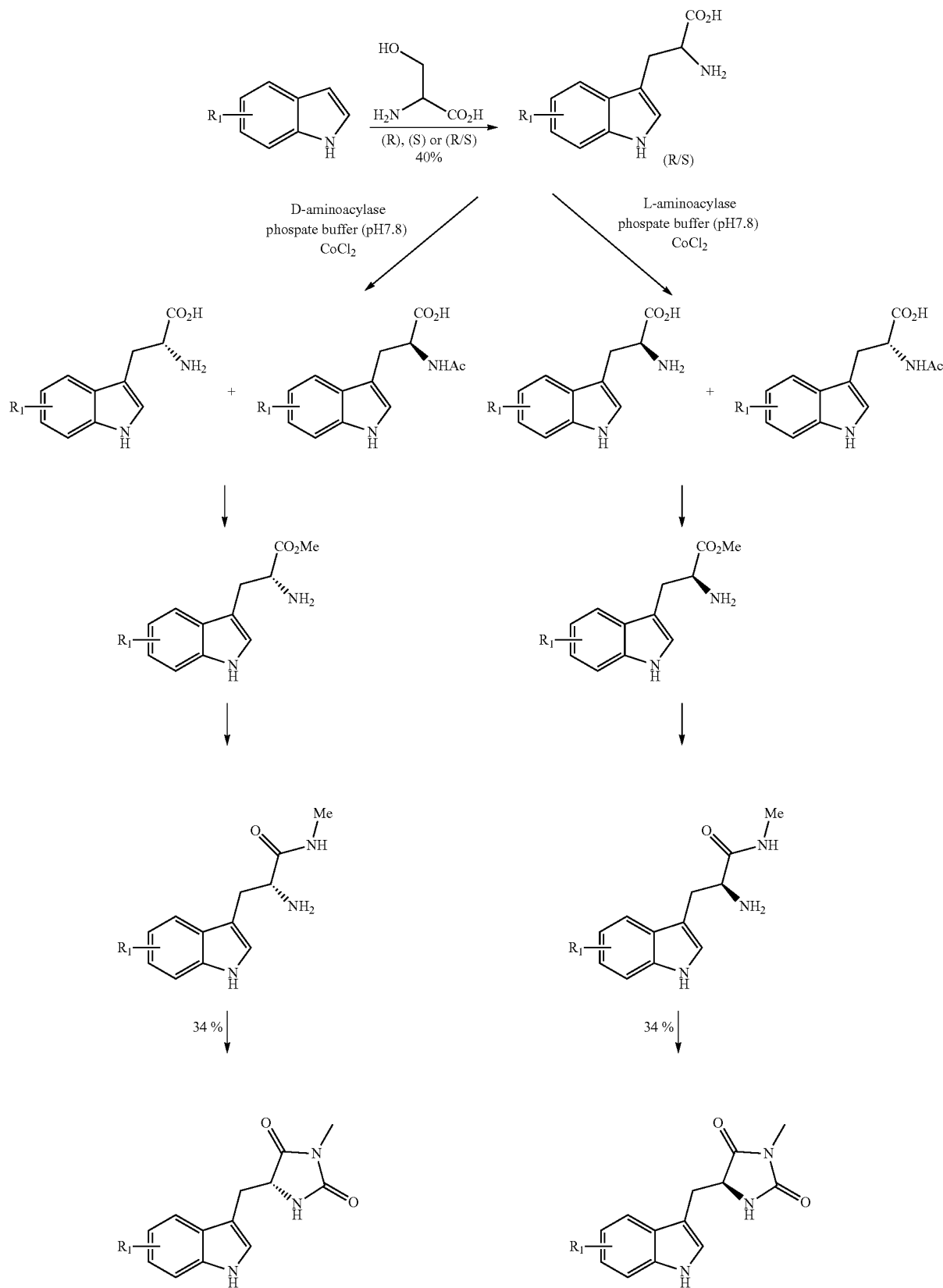
Comparative Reaction Scheme 3

In contrast to the above methods, the presently described methods are amendable to high-yielding, large scale production without requiring kinetic resolution. Accordingly, in some embodiments the invention provides a method for preparing a compound having the following structure (III):

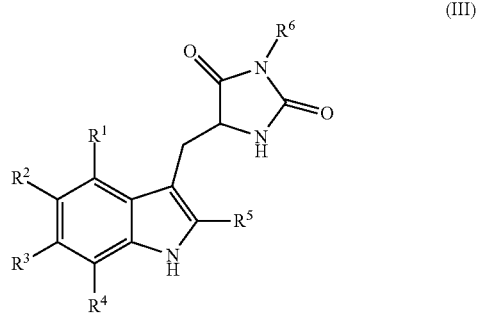

or a pharmaceutically acceptable salt, prodrug, stereoisomer or tautomer thereof, wherein:

$R^1$, $R^2$, $R^3$ and $R^4$ are each independently H, halo or $C_1$-$C_6$ alkyl;

$R^5$ is H or halo; and $R^6$ is H, $C_1$-$C_6$ alkyl, $C_1$-$C_6$ alkenyl, aralkyl, cycloalkylalkyl or heterocyclylalkyl, the method comprising reacting aldehyde (5), or a salt, stereoisomer or tautomer thereof, with phenylhydrazine (6), or a salt thereof, to yield (7), or a salt, stereoisomer or tautomer thereof, according to Reaction Scheme 1:

Reaction Scheme 1

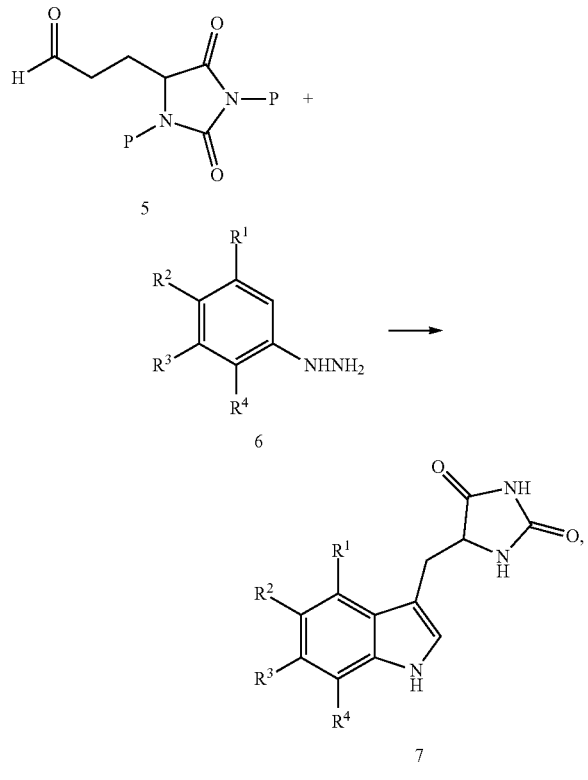

wherein each P is independently H or a protecting group. In some embodiments, each P is H. In other embodiments, each P is a protecting group such as butyloxycarbonyl (Boc).

In exemplary embodiments of Reaction Scheme 1, compound 5 is solvated in an alcohol solvent (e.g., methanol or ethanol) and compound 6 is then brought into contact with solvated compound 5. After contacting (e.g., stirring) for an amount of time sufficient for the reaction, an acid, such as sulfuric or phosphoric acid is added to the mixture to yield compound 7. In various embodiments, the mixture of 5 and 6 is stirred at temperatures of about 10-50° C., or about 10-30° C., before addition of the acid. In some other embodiments, the reaction temperature is increased to about 95-100° C. for a sufficient period of time after addition of the acid.

Compounds 5 and 6 can be present in various concentrations within the mixture of compounds 5 and 6 according to Reaction Scheme 1. For example, in some embodiments, the molar ratio of compound 5 to 6 ranges from about 1:0.9 to about 1:1.1, for example about 1:1. Compound 5 is typically present in about 1 gram for every 10-20 mL of solvent.

Different enantiomers of compound (5) can be used depending on the desired stereochemistry of the final product. Accordingly, in some embodiments aldehyde (5) has one of the following structures (5') or (5"):

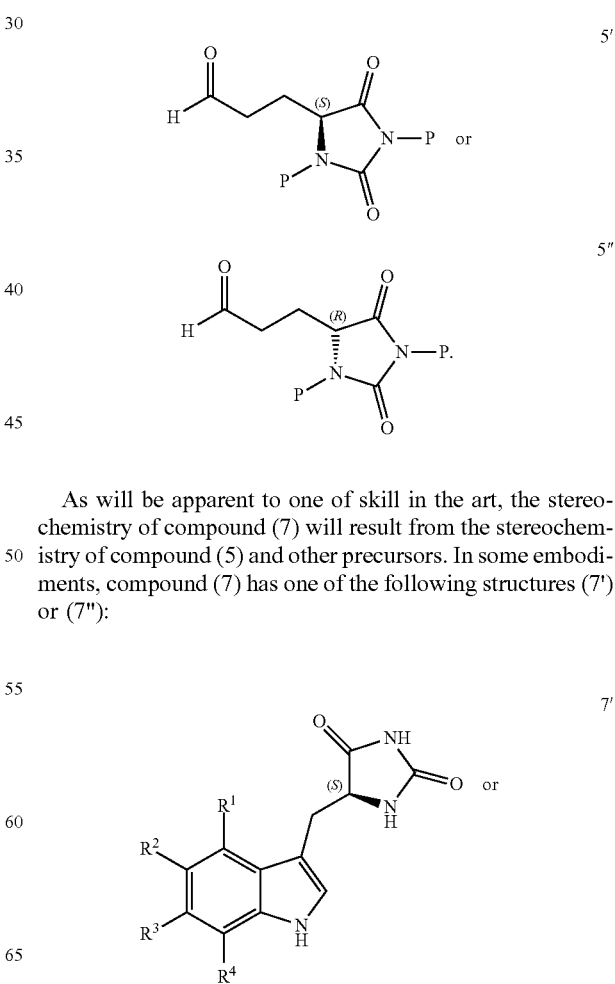

As will be apparent to one of skill in the art, the stereochemistry of compound (7) will result from the stereochemistry of compound (5) and other precursors. In some embodiments, compound (7) has one of the following structures (7') or (7"):

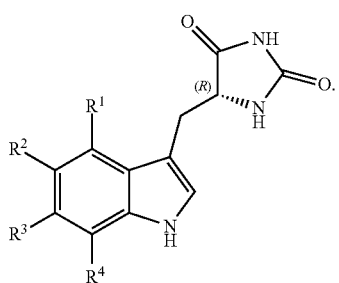

7″

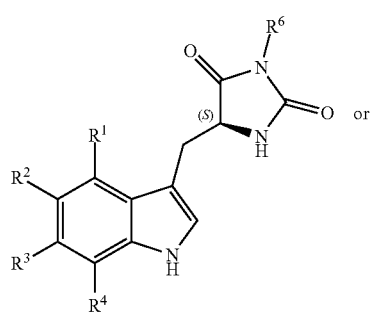

1′

The disclosed methods are useful for preparation of compounds of structure (III) having various different $R^6$ groups. For example, in some embodiments $R^6$ is $C_1$-$C_6$ alkyl, $C_1$-$C_6$ alkenyl, aralkyl, cycloalkylalkyl or heterocyclylalkyl, and the method further comprises reacting compound (7), or a salt, stereoisomer or tautomer thereof, with an alkylating agent (8) to yield (1), or a salt, stereoisomer or tautomer thereof, according to Reaction Scheme 2:

Reaction Scheme 2

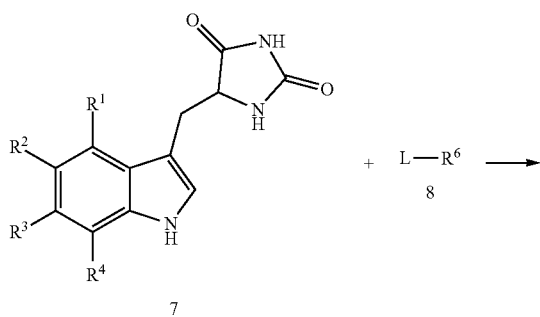

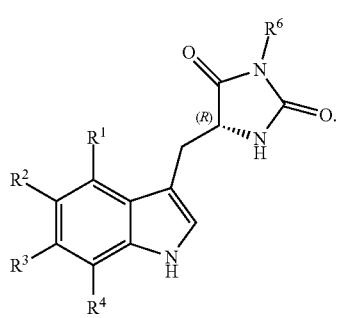

1″

An alkylating agent known in the art can be employed in the methods. In various embodiments the leaving group is halogen, for example bromine or iodine. In some different embodiments, the leaving group is sulfonate, such as p-toluenesulfonate or triflate.

Conditions for alkylation of compound 7 according to Reaction Scheme 2 are readily determined by one of ordinary skill in the art. In some embodiments, compound 7 is dissolved in a solvent, the alkylation reagent (L-$R^6$) and a base are added to the mixture, then the reaction mixture is stirred. Exemplary solvents for this purpose include polar and non-protic solvents, for example DMSO or DMF. The amount of the solvent can be varied, and in certain embodiments the solvent is present in about 10-40 mL/g based on compound 7.

Some embodiments include use of a base to effect the reaction illustrated in Reaction Scheme 2. In some embodiments, the base is an alkali metallic carbonate or tert-alkylamine having from 1-4 carbon atoms. In certain embodiments, the alkali metallic carbonate is potassium carbonate, cesium carbonate or sodium carbonate. In other embodiments, the tert-alkylamine is triethylamine. The amount of base employed can be varied, and typically ranges from about 1.2-1.5 moles per mole of compound 7, for example about 1.5 mole per mole of compound 7.

In various embodiments, the alkylation reagent is present at about 1.2-1.5 moles per mole of compound 7, for example about 1.5 moles per mole of compound 7. In other various embodiments, the alkylation of compound (7) is performed at temperatures from about 0-80° C., for example about 10-30° C. In other embodiments, the alkylation reagent (L-$R^6$) is methyl p-toluensulfonate or L-methyl, wherein L is a halogen.

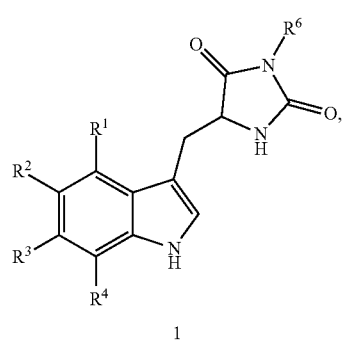

1 wherein L is a leaving group.

Again, the stereochemistry of the final product is typically controlled by the stereochemistry of the precursors, and in various embodiments compound (1) has one of the following structures (1′) or (1″):

Compounds with different $R^6$ moieties can be prepared by selection of the appropriate alkylating agent. In some embodiments, $R^6$ is $C_1$-$C_6$ alkyl, for example in some embodiments $R^6$ is methyl. In other embodiments, $R^6$ is ethyl, propyl, isopropyl or butyl. Embodiments wherein $R^6$ is methyl typically employ methyl iodide as the alkylating reagent. In some embodiments, the $C_1$-$C_6$ alkyl is substituted. In other embodiments, the $C_1$-$C_6$ alkyl is unsubstituted.

In various different embodiments, $R^6$ is aralkyl. In some embodiments, the aralkyl is substituted. In other embodiments, the aralkyl is unsubstituted. The aryl moiety of the aralkyl can be any of a number of aryl moieties, including phenyl, biphenyl and phenol moieties.

In some specific embodiments, $R^6$ is benzyl. For example, in some embodiments $R^6$ has the following structure:

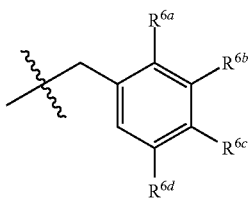

wherein $R^{6a}$, $R^{6b}$, $R^{6c}$ and $R^{6d}$ are each independently H, halo, $C_1$-$C_6$ alkyl or $C_1$-$C_6$ haloalkyl. In some embodiments, $R^{6a}$ is H, F or Cl; $R^{6b}$ is H, F, Cl, $CH_3$ or $CF_3$; $R^{6c}$ is H, F, Cl, I or $CH_3$; and $R^{6d}$ is H, F or $CF_3$.

In some other specific embodiments, $R^6$ has one of the following structures:

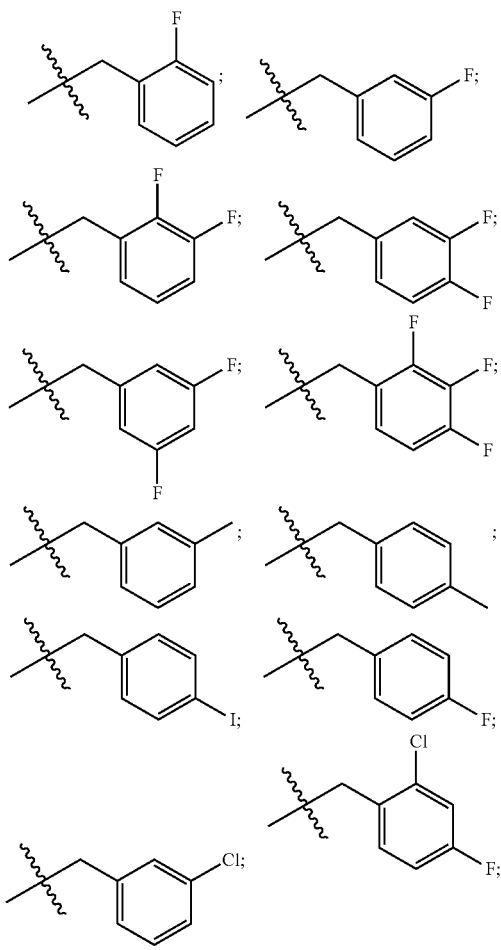

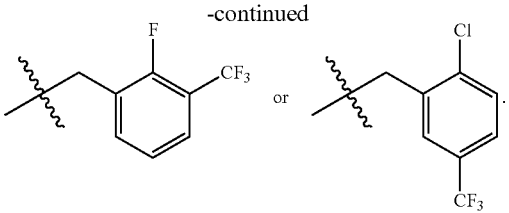

In other different embodiments, $R^6$ is heterocyclyalkyl. In some of these embodiments, the hetereocyclylalkyl is substituted. In some other of these embodiments, the hetereocyclylalkyl is unsubstituted. In some exemplary embodiments, the heterocyclylalkyl is heteroarylalkyl. For example, in various embodiments $R^6$ is pyridinylalkyl, for example the following structure:

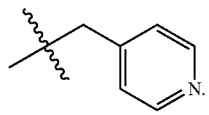 [SMILES: *Cc1ccncc1]

In other embodiments, the heterocyclylalkyl is aliphatic, for example in some embodiments the heterocycle of the heterocyclylalkyl comprises oxygen or nitrogen, for example tetrahydrofuranyl, pyranyl, piperidinyl or ethylene oxide. In some embodiments, the heterocyclylalkyl has one of the following structures:

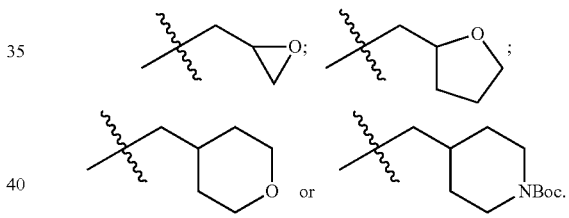

In some different embodiments, $R^6$ is cycloyalkylalkyl, such as cyclopropyl or cyclopentyl. For example, one of the following structures:

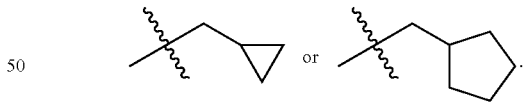

In some different embodiments, $R^6$ is $C_1$-$C_6$ alkenyl. For example, in some embodiments $R^6$ has the following structure:

Compounds of structure (III), wherein $R^5$ is halogen (i.e., $R^{5'}$) can be prepared in various embodiments by methods which further comprise treating compound (1) with a halogenating reagent to form a compound of structure (III), wherein $R^5$ is halogen. Exemplary halogenating reagent in some embodiments are N-bromosuccinimide or N-chlorosuccinimide, which can be employed at molar ratios derivable by one of ordinary skill in the art.

In some embodiments, the method for preparing compounds of structure (III), wherein $R^5$ is halogen, comprise dissolving compound (III) (prepared according to Reaction Scheme 2) in a solvent under inert atmosphere (e.g., $N_2$), adding the halogenation reagent heating the mixture to reflux for a sufficient period of time to effect halogenation (e.g., from about 3-6 hours).

Typical solvents for the halogenation of compound (III) include non-polar solvents, such as $CCl_4$. The amount of the solvent used can be varied according to the knowledge of one of ordinary skill in the art.

The halogenated product can be purified according to common procedures. In some embodiments, the reaction mixture is cooled to room temperature and filtered. The filtrate is then concentrated and purified by flash chromatography. The procedure and mobile phase of flash chromatography is selected according to the general practice in the art.

In some embodiments of the foregoing method, aldehyde (5) is provided in a protected form. The protecting group may be removed prior to reaction with compound (6) according to Reaction Scheme 1. Exemplary deprotection conditions include reduction, such as hydrogenation. Accordingly, in some embodiments aldehyde compound (5) has been prepared by reducing compound (4):

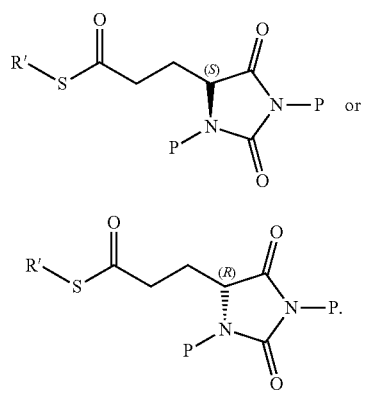

(4)

wherein R' is $C_1$-$C_6$ alkyl. In some embodiments, R' is ethyl (Et).

Again, stereochemistry of the final product may depend on the stereochemistry of the intermediate compounds, and thus in some embodiments compound (4) has one of the following structures (4') or (4"):

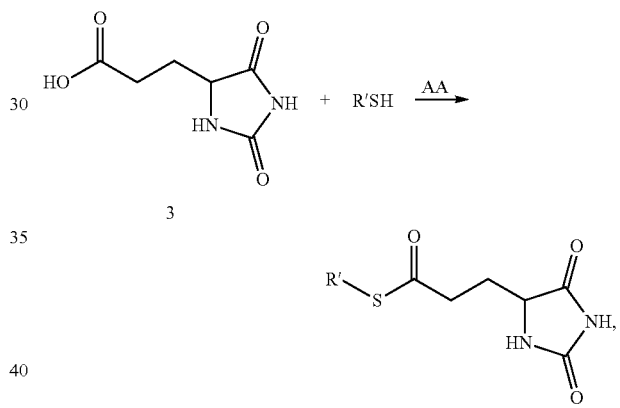

In certain embodiments, compound (5) is prepared from compound (4) under conditions for hydrogenation, for example by treating compound (4) with palladium and triethylsilane. Typically the Pd is Pd/C (e.g., 10% of Pd/C). In some embodiments, the ratio of the volume of triethylsilane to the mass of Pd/C ranges from about 10:1 to about 30:1, for example about 20:1. In certain embodiments, the ratio of triethylsilane to compound 4 ranges from about 1:1 to about 5:1, for example about 3:1.

Various different conditions familiar to those of skill in the art can be used for reduction of compound 4. For example, in some embodiments compound (4) is dissolved in a solvent and cooled in an ice bath, followed by addition of the reducing agent. In some exemplary embodiments, the reaction mixture thus obtained is stirred in the ice bath for 3~5 min. and warmed to room temperature for 0.5~1 hours to provide compound 5. Typical reaction temperatures for the reduction of compound (4) range from about −10-40° C., for example about 0-30° C.

Typical solvents for reduction of compound (4) include tetrahydrofuran and dichloromethane. The amount of the solvent can be varied and is some embodiments ranges from about 10-40 mL/g based on compound 4.

In still other embodiments, compound (4) has been prepared from the corresponding acid (3) according to Reaction Scheme 3:

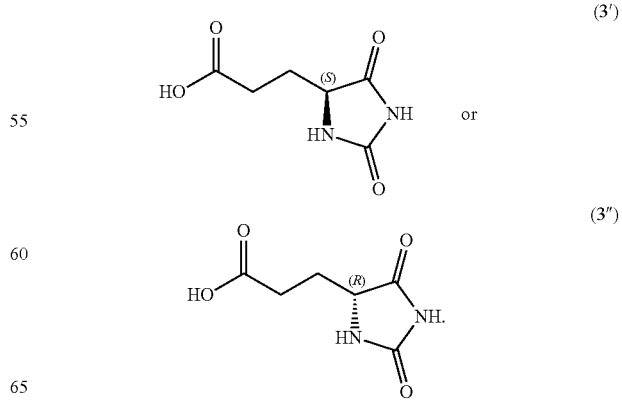

wherein AA is an acid activating reagent, such as DCC, EDCl, or other activating agents known in the art.

In some more specific embodiments, compound (3) has one of the following structures (3') or (3"):

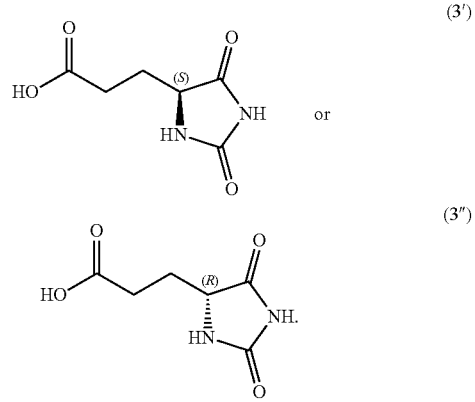

For the synthesis of compound 4, typical procedures comprise dissolving compound (3) in a solvent and cooling in an ice bath. The activating (condensation) reagent, alkylthiol (e.g., ethanethiol) and an optional catalyst are then added. The reaction mixture is then stirred in the ice bath for 5-15 min (e.g., 10 min) and then warmed to room temperature for 2-3 hours to provide compound 4.

In still further embodiments of the foregoing method compound (3) has been prepared from an amino acid having the following structure (2):

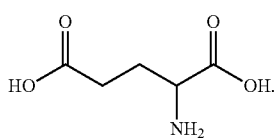
(2)

In various embodiments, compound (2) has one of the following structures (2') or

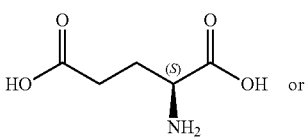
(2')

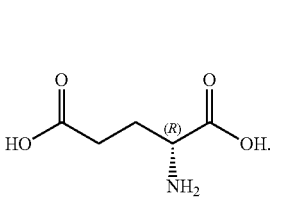
(2")

In still more embodiments, the method comprises one or more of the following transformations (A), (B), (C), (D), (E) or (F):

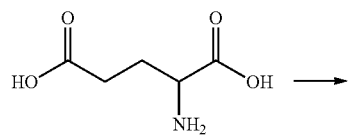
(A)

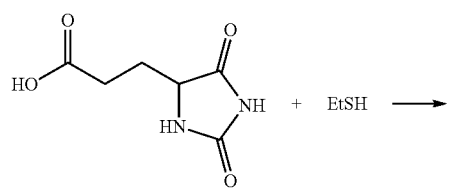
(B)

-continued

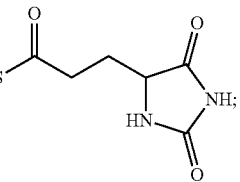

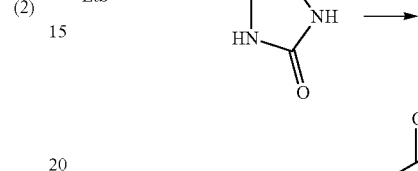
(C)

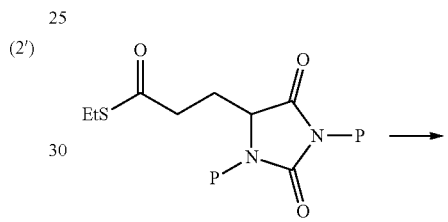
(D)

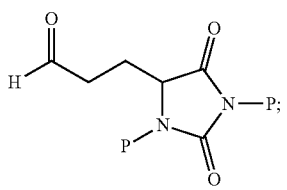
(E)

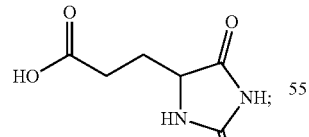

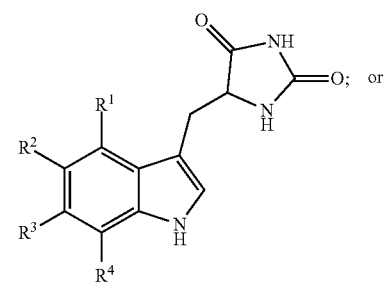

-continued

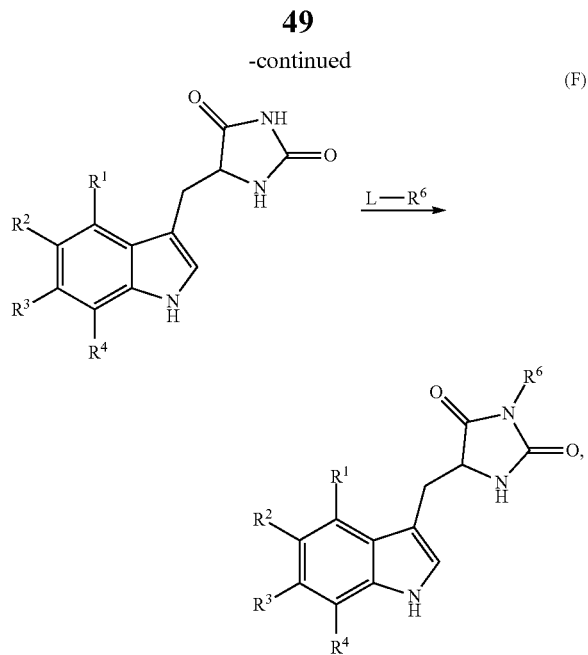

wherein:
each P is independently H or a protecting group;
each $P^1$ is independently a protecting group; and
and L is a leaving group.

In some embodiments of the foregoing, the method comprises transformation (E) and least one of transformations (A), (B), (C), (D) and/or (F). In various embodiments, the method comprises transformation (D) and (E). In other embodiments, the method comprises each of transformations (A), (B), (C), (D), (E) and (F).

In still other embodiments, the method further comprises the following transformation:

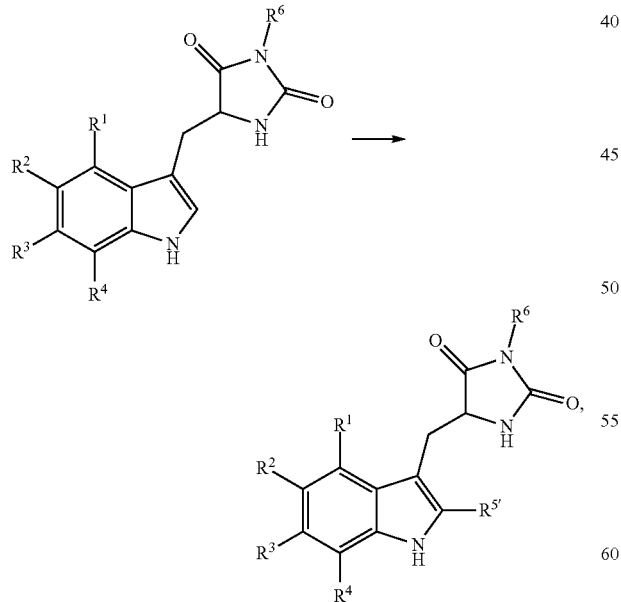

wherein $R^{5'}$ is halo.

The synthetic methods described herein may be used to prepare various indole-hydantoin compounds of structure (III). In some embodiments, the compounds are compounds wherein $R^1$ is H, Cl or F. In other embodiments, $R^2$ is H, Cl or F. In still more embodiments, $R^3$ is H, Cl or F. In other embodiments, $R^4$ is H, Cl or I. In some more specific embodiments, $R^1$ is H, $R^2$ is H, $R^3$ is F and $R^4$ is Cl. In still other embodiments, Each of $R^1$, $R^2$, and $R^3$ are H and $R^4$ is Cl. In various embodiments of any of the foregoing, $R^6$ is methyl, and in other embodiments, $R^6$ is benzyl, which is unsubstituted or substituted with one or more halo.

In still other embodiments $R^5$ is H. In different embodiments, $R^5$ is Br or Cl.

Exemplary compounds which can be prepared according to various embodiments of the methods include the following compounds:

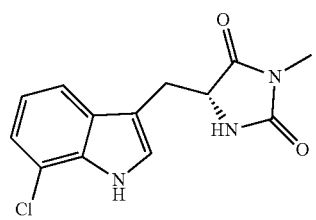

1aa

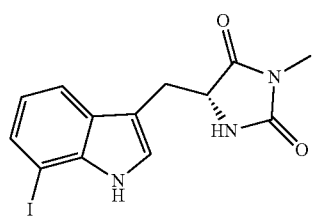

1ba

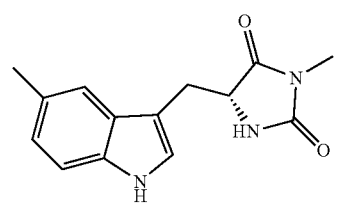

1ca

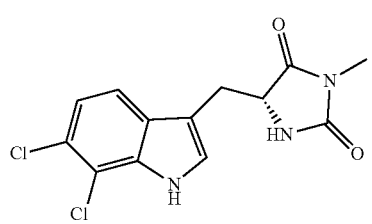

1da

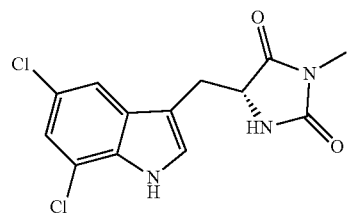

1ea

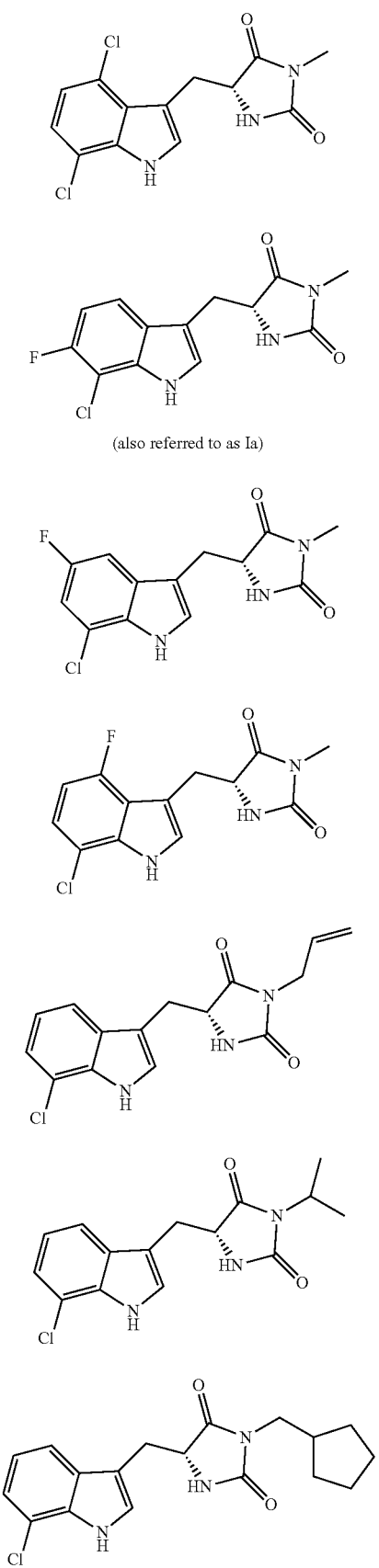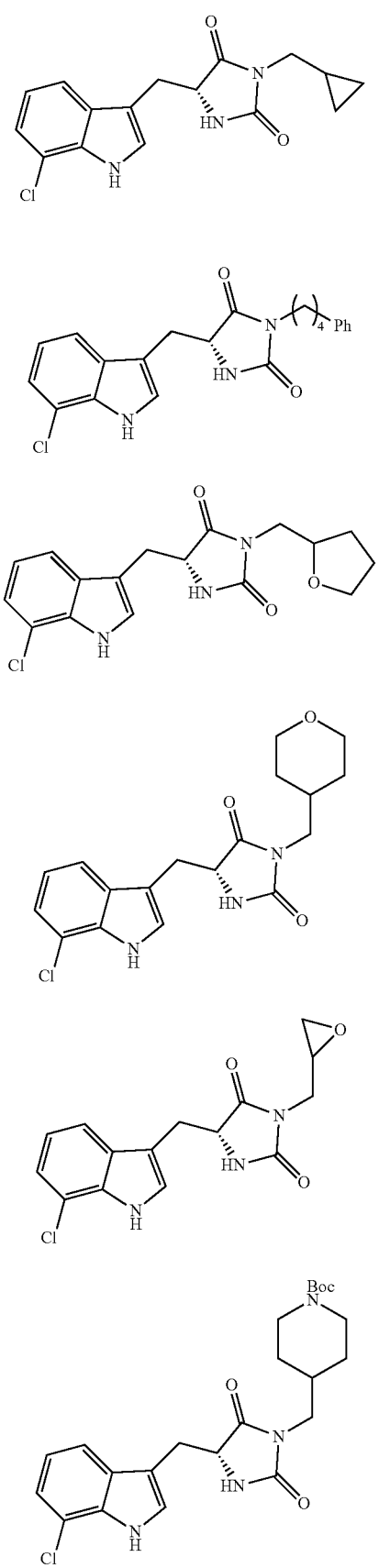

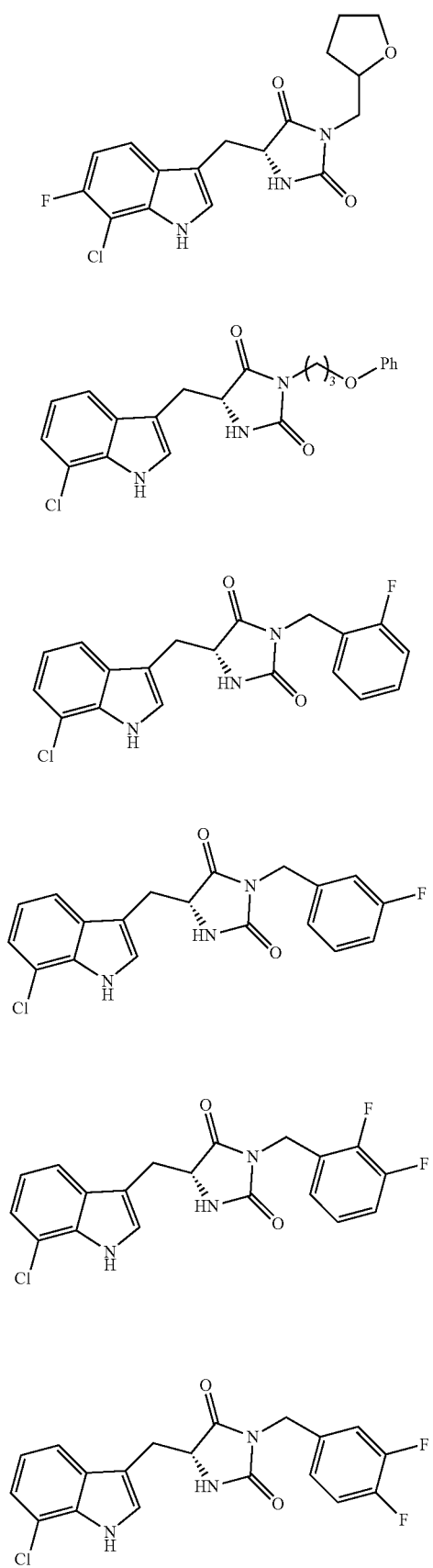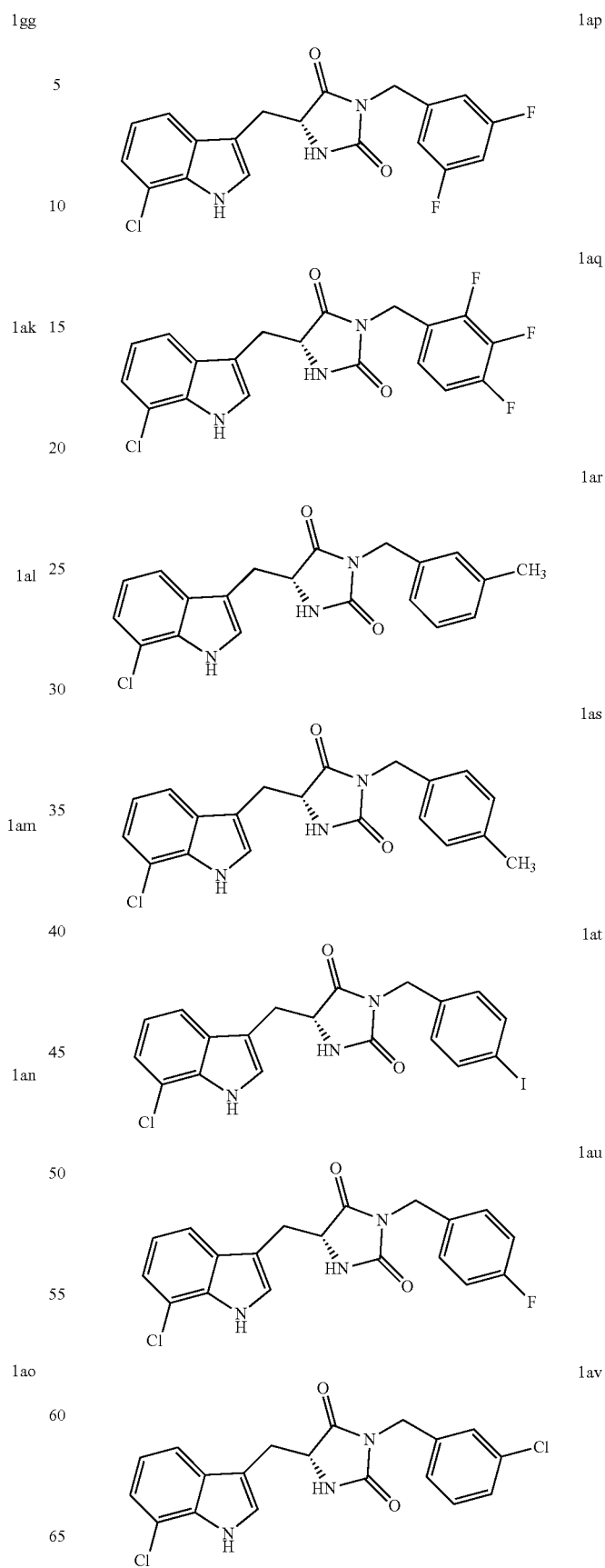

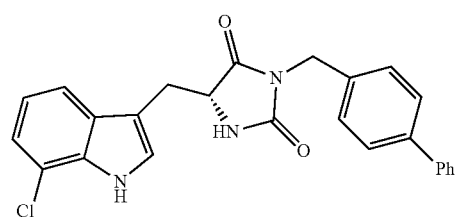 1aw
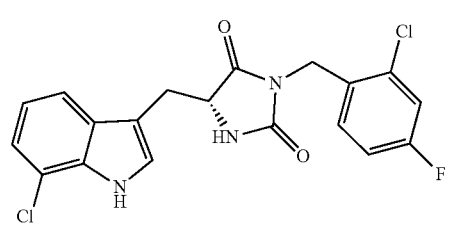 1ax
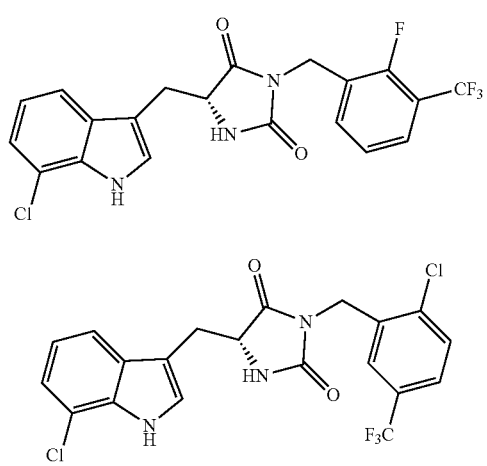 1ay
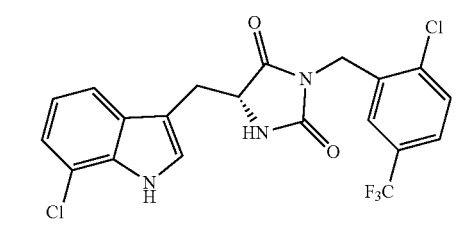 1az
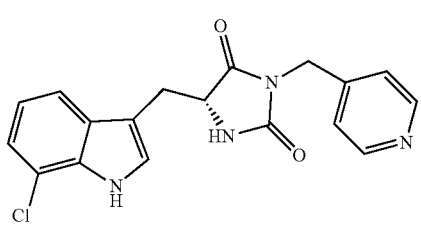 1aaa
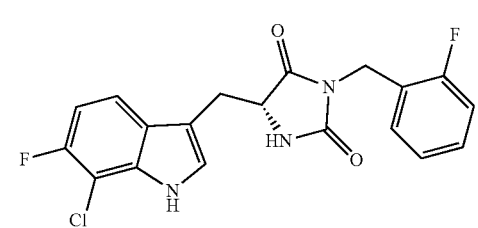 1gl
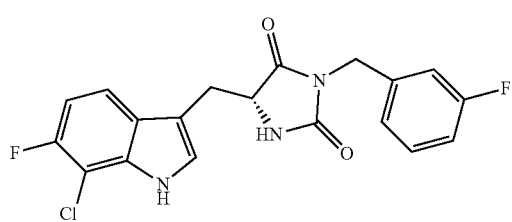 1gm
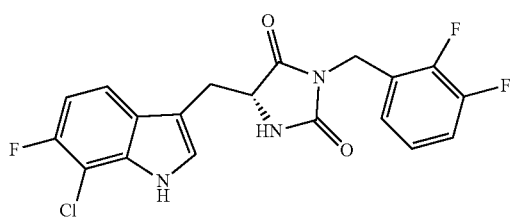 1gn
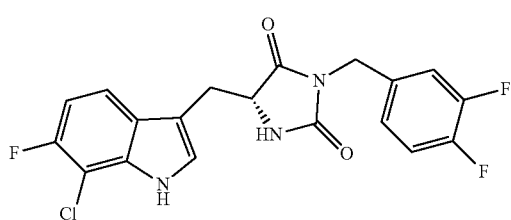 1go
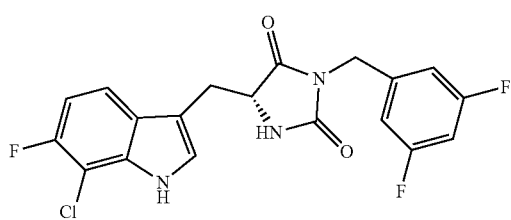 1gp
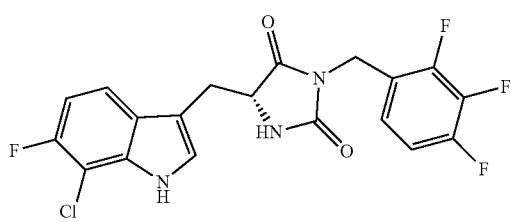 1gp
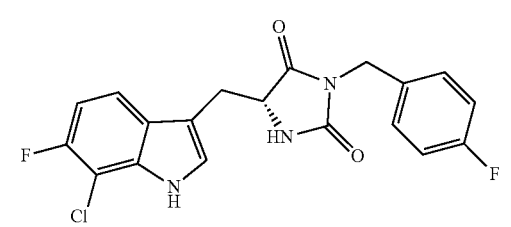 1gu
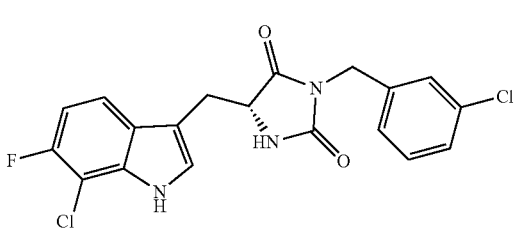 1gv
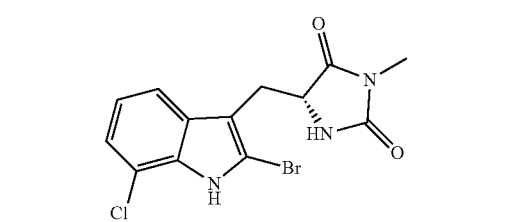 1aab -continued

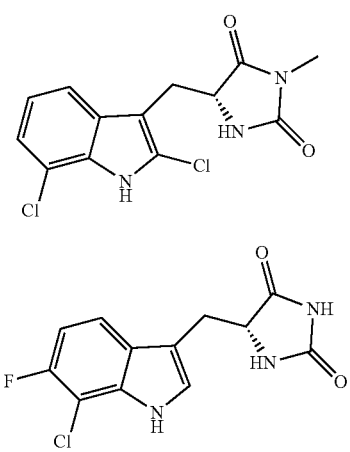

Compounds useful in the above synthetic methods are also provided. Accordingly, in some embodiments, the invention provides a compound having one of the following structures (4') or (4"):

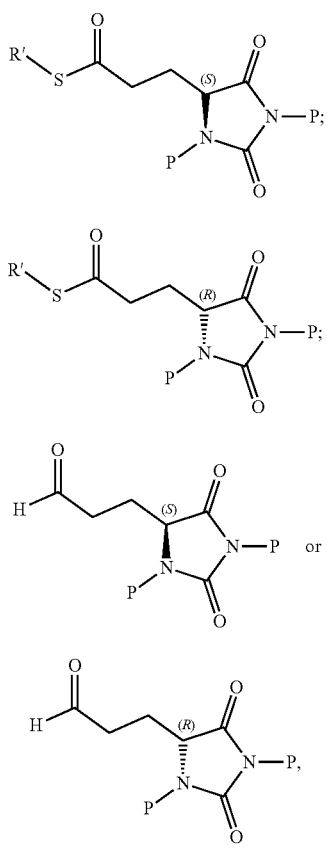

or a salt or tautomer thereof, wherein:
  each P is independently H or a protecting group; and
  R' is $C_1$-$C_6$ alkyl, such as ethyl.
Mixtures (e.g., racemic mixtures) of (4') and (4") or (5') and (5") are also provided.
It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diaryl alkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P.G.M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

EXAMPLES

All non-aqueous reactions were carried out in oven- or flame-dried glassware under nitrogen atmosphere. All chemicals were purchased from commercial vendors and used as is, unless otherwise specified. Reactions were magnetically stirred and monitored by thin layer chromatography (TLC) with 250 µm pre-coated silica gel plates, visualized either with UV, or in an iodine chamber. Flash column chromatography was performed using silica gel (100-200 mesh). Chemical shifts are reported relative to chloroform (δ 7.26), methanol (δ 3.31), or DMSO (δ 2.50) for $^1$H NMR.

Example 1

Preparation of (R)-5-((7-chloro-6-fluoro-1H-indol-3-yl)methyl)-3-methylimidazolidine-2,4-dione (Ia)

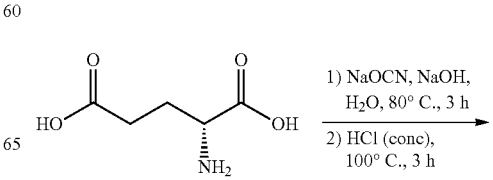

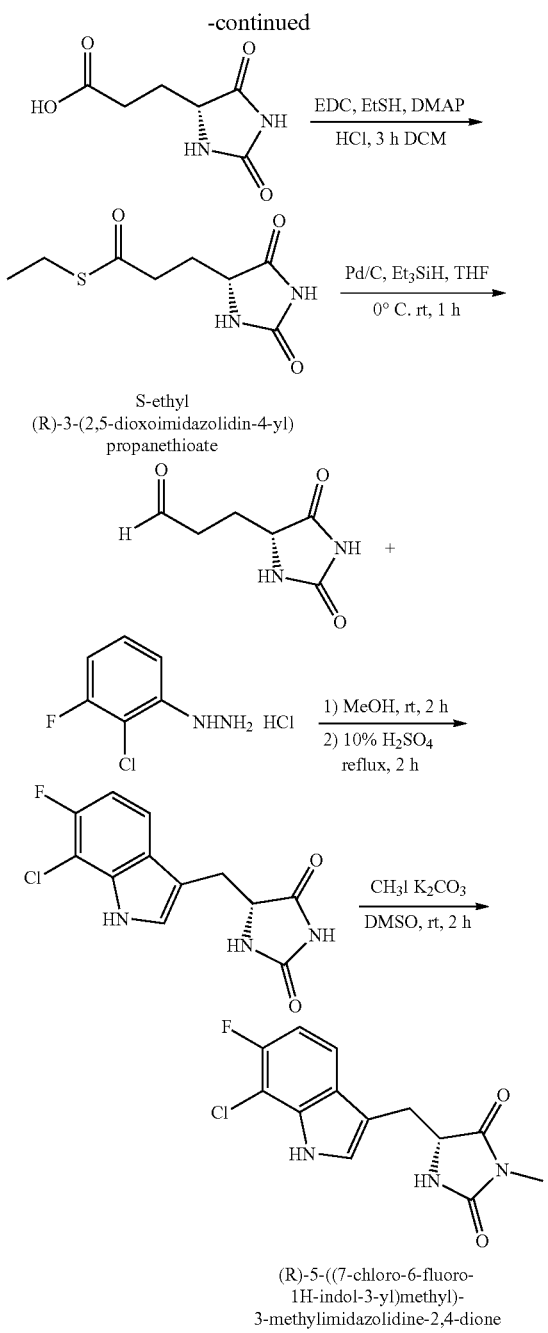

S-ethyl (R)-3-(2,5-dioxoimidazolidin-4-yl)propanethioate (R)-5-((7-chloro-6-fluoro-1H-indol-3-yl)methyl)-3-methylimidazolidine-2,4-dione (R)-3-(2,5-dioxoimidazolidin-4-yl)propanoic acid: NaOH (12.5 M, 80 mL, 1.0 mol) was added dropwise to a suspension of D-glutamic acid (147 g, 1.0 mol) in water (120 mL) at 10° C. The mixture was stirred at room temperature for 10 minutes, and then NaOCN (71.6 g, 1.1 mol) was added. The reaction was heated to 80° C. for 3 hours. Concentrated HCl (183 mL, 2.2 mol) was added while maintaining a temperature below 20° C. by ice bath. The resulting mixture was refluxed for 3 hours, then cooled to room temperature without stirring for 12 hours until a white solid was deposited. The mixture was filtered and washed with water (100 mL×2) and dried in vacuo to afford the desired product as a white solid (122 g, 71%, 99% ee).

S-ethyl (R)-3-(2,5-dioxoimidazolidin-4-yl)propanethioate: To a solution of (R)-3-(2,5-dioxoimidazolidin-4-yl)propanoic acid (0.1 mol, 17.2 g) in 200 mL DCM, EDC (0.11 mole, 21 g), EtSH (0.1 mol, 6.2 g), and DMAP (0.008 mol, 0.97 g) were added sequentially while cooling the reaction mixture to 0° C. with an ice bath. The reaction temperature was maintained for 10 minutes, followed by removal of the ice bath to allow the reaction temperature to warm to room temperature for 3 hours. The reaction was monitored by TLC (SiO$_2$, 100% methanol). Upon completion, the reaction was quenched by adding 0.5 M HCl (100 mL). The crude reaction mixture was then filtered and the aqueous phase was extracted with DCM (100 mL×2). The organic phase was concentrated in vacuo to yield a white solid. The filter cake was slurried in water (200 mL) to remove ethanethiol. The slurry was filtered and dried over the filter cake to afford the desired product as a white solid (17.5 g, 81%). $^1$H NMR (500 MHz, DMSO-d$_6$) δ 10.63 (s, 1H), 7.94 (s, 1H), 4.09-3.91 (m, 1H), 2.82 (q, J=7.4 Hz, 2H), 2.74-2.60 (m, 2H), 2.03-1.90 (m, 1H), 1.82-1.70 (m, 1H), 1.16 (t, J=7.4 Hz, 3H).

(R)-3-(2,5-dioxoimidazolidin-4-yl)propanal: To a solution of S-ethyl (R)-3-(2,5-dioxoimidazolidin-4-yl)propanethioate (10 mmol) in THF (20 mL) cooled with an ice bath to 0° C., 10% Pd/C (0.2 g) and Et$_3$SiH (4.1 mL, 30 mmol) were added. The ice bath was removed after 5 minutes, and the reaction was allowed to stir at room temperature for 1 h while being monitored by TLC (SiO$_2$, DCM/methanol=10:1). Solid Pd/C was removed by filtration and the crude reaction mixture was concentrated in vacuo to afford the desired product. The crude product was used in the next synthetic step without further purification.

(R)-5-((7-chloro-6-fluoro-1H-indol-3-yl)methyl)imidazolidine-2,4-dione: To a solution of (R)-3-(2,5-dioxoimidazolidin-4-yl)propanal (10 mmol) in methanol (20 mL) (2-chloro-3-fluorophenyl)hydrazine hydrochloride (10 mmol) was added. The reaction was allowed to stir at room temperature for 2 hours while being monitored by TLC (SiO$_2$, DCM/methanol=10:1). When the reaction was complete, methanol was removed in vacuo, affording the crude product as a dark brown solid. The mixture was then refluxed for 2 hours in 10% H$_2$SO$_4$ (20 mL) while monitoring the reaction by TLC (SiO$_2$, DCM/methanol=10:1). After the reaction was complete, the mixture was allowed to cool to room temperature. The mixture was extracted with ethyl acetate (4×10 mL) and the combined organic phases were pooled and dried over anhydrous Na$_2$SO$_4$. The product was filtered and concentrated in vacuo and purified by column chromatography (SiO$_2$) and recrystallized to afford the desired product (0.85 g, 33% 99.3% ee). $^1$H NMR (400 MHz, DMSO-d$_6$) δ 11.45 (s, 1H), 10.37 (s, 1H), 7.90 (s, 1H), 7.52 (dd, J=8.7, 4.7 Hz, 1H), 7.21 (d, J=2.4 Hz, 1H), 7.03 (dd, J=10.2, 8.8 Hz, 1H), 4.33 (t, J=4.5 Hz, 1H), 3.06 (dd, J=4.4, 3.1 Hz, 2H); $^{13}$C NMR (126 MHz, DMSO-d$_6$) 176.08, 157.82, 155.12, 153.23, 133.46, 126.06, 118.75, 110.09, 108.18, 102.27, 58.58, 26.67; ESI-MS m/z 282.4 (M+H)$^+$; MALDI-HRMS m/z calcd for C$_{12}$H$_9$ClFN$_3$O$_2$ (M)$^+$281.0367, found 281.0361.

(R)-5-((7-chloro-6-fluoro-1H-indol-3-yl)methyl)-3-methylimidazolidine-2,4-dione: To a solution of (R)-5-((7-chloro-6-fluoro-1H-indol-3-yl)methyl)imidazolidine-2,4-dione (1 mmol) in 2 mL DMSO, methyl iodide (1.5 mmol) and K$_2$PO$_4$ (1.5 mmol) were added. The reaction mixture was stirred at room temperature for 2.5 hours while monitoring by TLC (SiO$_2$, DCM/methanol=10:1). When the reaction was complete, it was quenched with 5 mL of water and extracted with ethyl acetate (3×5 mL). The organic phases were pooled and dried over anhydrous Na$_2$SO$_4$. The product was filtered, concentrated in vacuo, and purified using column chromatography (SiO$_2$) to afford the desired product (75%, 98.9% ee). $^1$H NMR (500 MHz, DMSO-d$_6$) δ 11.48 (s, 1H), 8.22 (d, J=10.6 Hz, 1H), 7.50 (dd, J=8.7, 4.7 Hz, 1H), 7.20 (d, J=2.4 Hz, 1H), 7.02 (dd, J=10.1, 8.7 Hz, 1H), 4.35 (t, J=5.6 Hz, 1H), 3.11 (dd, J=15.0, 4.6 Hz, 1H), 3.05 (dd, J=14.9, 5.6 Hz, 1H), 2.62 (s, 3H); $^{13}$C NMR (126 MHz, DMSO-d$_6$) δ 174.52, 157.33, 155.10, 153.22, 133.52, 126.45, 118.66, 110.08, 108.33, 102.45, 57.44, 26.89, 24.27; ESI-MS m/z 318.1 (M+Na)$^+$; ESI-HRMS m/z calcd for C$_{13}$H$_{11}$ClFN$_3$NaO$_2$ (M+Na)$^+$ 318.0416, found 318.0428.

Example 2

Exemplary Preparations of Compound 4

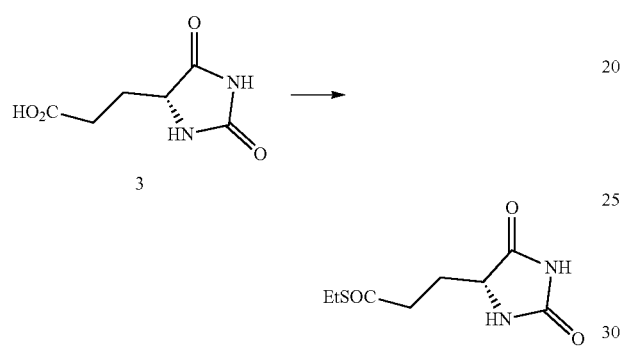

To a solution of compound 3 (0.1 mol, 17.2 g) in 200 mL DCM, EDCl (0.11 mol, 21 g) in the ice bath (0-5° C.), EtSH (0.1 mol, 6.2 g) and the catalyst DMAP (0.008 mol, 0.97 g) were added sequentially. After keeping the temperature for 10 min, the bath was removed and kept stirring at room temperature for 2.5-3 h until TLC detected the reaction was complete (eluting with MeOH). The reaction was then quenched by adding 100 mL 0.5 mol/L HCl solution. The reaction mixture was then filtrated after stirring for 2 min and the filtrate was separated, and the aqueous phase was then extracted twice with 100 mL DCM. A white solid was obtained from the combined organic phases and concentrated in vacuum. The solid and the filter cake was slurried in 200 mL water to remove ethanethiol. The final product was obtained by filtering and drying over the filter cake. (17.5 g, 81%), $^1$H NMR (500 MHz, dmso-d$_6$) δ 10.63 (s, 1H), 7.94 (s, 1H), 4.09-3.91 (m, 1H), 2.82 (q, J=7.4 Hz, 2H), 2.74-2.60 (m, 2H), 2.03-1.90 (m, 1H), 1.82-1.70 (m, 1H), 1.16 (t, J=7.4 Hz, 3H).

Compound 4 was obtained according to the methods and conditions described above, with different condensation reagent and solvent. The results are summarized in Table 2 below:

TABLE 2

Exemplary Conditions for Preparation of Compound (4)

| Entry | solvent | Condensation reagent | yield % |
|---|---|---|---|
| 1 | DCM | DCC | 65 |
| 2 | DCM | EDCI | 81 |
| 3 | THF | EDCI | 72 |
| 4 | THF | DCC | 70 |

Example 3

Preparation of Compound 5

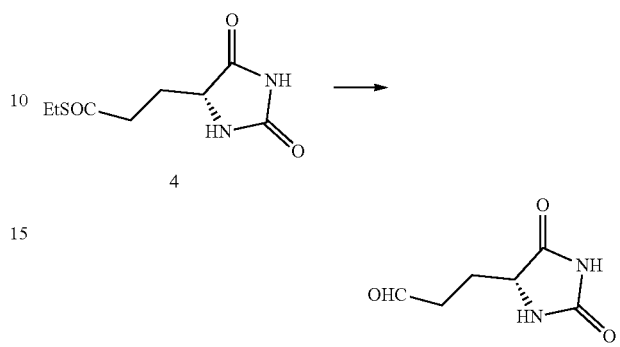

To a solution of thioester compound 4 (10 mmol) in 20 mL THF in ice bath, 10% Pd/C (0.2 g) and Et$_3$SiH (4.1 mL, 30 mmol) was added. The ice bath was removed after 5 min and the reaction was allowed to stir at room temperature for 0.5-1 h until TLC detected the reaction was complete (eluting with DCM:MeOH=10:1). The catalyst was removed by filtration and the filtrate concentrated to provide compound 5.

Example 4

Exemplary Preparations of Compound 7

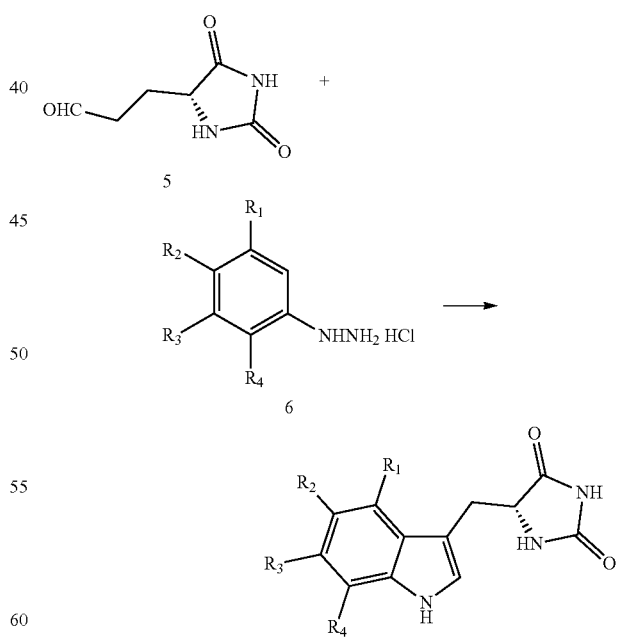

To a solution of compound 5 (10 mmol) in 20 mL MeOH in 100 mL round flask, substituted phenylhydrazine hydrochloride 6 (1 equiv) was added. The reaction mixture was allowed to stir at room temperature for 1.5-2 h until TLC detected the reaction was complete (eluting with DCM:MeOH=10:1). MeOH was removed to afford a dark brown solid and the mixture was then refluxed for 2 h with 20 mL 10% $H_2SO_4$ until TLC detected the reaction complete (eluting with DCM:MeOH=10:1). After cooling to room temperature, the reaction mixture was extracted with ethylacetate (10 mL×4). The organic phases were combined and dried over anhydrous $Na_2SO_4$. After concentrating in vacuum, compound 7a was obtained by column chromatography, which after recrystallization (0.85 g, 33%) had an ee value: 99.3%. Analogous conditions produced 7b with an ee value of 99.3%

Synthetic conditions and results for various compounds of structure (7) are provided in Table 3 below (the yield in this table is the yield from compound 4 to 7):

TABLE 3

Exemplary Preparations of Compound (7)

| entry | 6 | Product 7 | yield % |
|---|---|---|---|
| 1 | 6a | 7a | 35 |
| 2 | 6b | 7b | 40 |
| 3 | 6c | 7c | 36 |
| 4 | 6d | 7d | 33 |
| 5 | 6e | 7e | 35 |

TABLE 3-continued

Exemplary Preparations of Compound (7)

| entry | 6 | Product 7 | yield % |
|---|---|---|---|
| 6 | 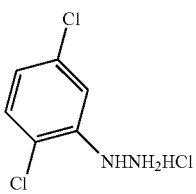 6f | 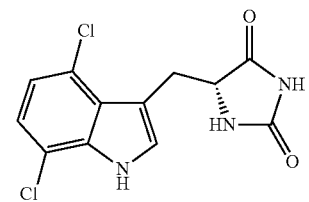 7f | 30 |
| 7 | 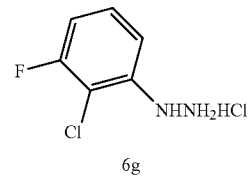 6g | 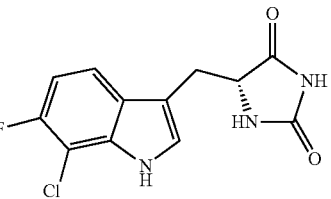 7g | 33 |
| 8 | 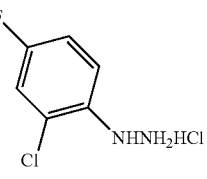 6h | 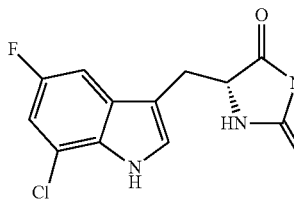 7h | 35 |
| 9 | 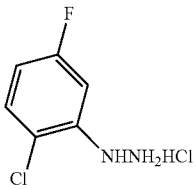 6i | 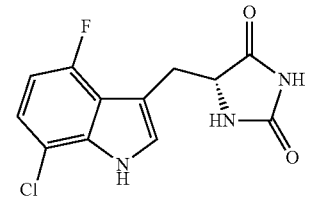 7i | 32 |

Compounds 7a-i were analyzed by NMR and mass spectrometry. Data is provided below:

7a: $^1$H NMR (500 MHz, DMSO-d$_6$) δ 11.27 (s, 1H), 10.37 (s, 1H), 7.90 (s, 1H), 7.53 (d, J=7.9 Hz, 1H), 7.21 (d, J=2.3 Hz, 1H), 7.14 (d, J=7.5 Hz, 1H), 6.98 (t, J=7.8 Hz, 1H), 4.33 (t, J=4.8 Hz, 1H), 3.10 (dd, J=14.0, 4.0 Hz, 1H), 3.06 (dd, J=14.0, 3.6 Hz, 1H); $^{13}$C NMR (126 MHz, DMSO-d$_6$) δ 176.10, 157.83, 133.11, 129.97, 126.01, 120.85, 119.85, 118.26, 116.15, 109.88, 58.63, 26.90; ESI-MS m/z 286.1 (M+Na)$^+$; ESI-HRMS m/z calcd for C$_{12}$H$_{10}$ClN$_3$NaO$_2$ (M+Na)$^+$ 286.0354, found 283.0863.

7b: $^1$H NMR (500 MHz, DMSO-d$_6$) δ 10.85 (s, 1H), 10.36 (s, 1H), 7.89 (s, 1H), 7.58 (d, J=7.9 Hz, 1H), 7.46 (d, J=7.4 Hz, 1H), 7.19 (d, J=2.5 Hz, 1H), 6.80 (t, J=7.7 Hz, 1H), 4.33 (t, J=4.8 Hz, 1H), 3.07 (dd, J=15.1, 5.1 Hz, 1H), 3.03 (dd, J=15.1, 4.8 Hz, 1H); $^{13}$C NMR (126 MHz, DMSO-d$_6$) δ 176.12, 157.83, 138.02, 130.27, 128.56, 125.75, 120.84, 119.30, 109.99, 77.27, 58.62, 26.99; ESI-MS m/z 356.2 (M+H)+; MALDI-HRMS m/z calcd for C$_{12}$H$_{10}$IN$_3$O$_2$ 354.9818 ($^{79}$I, M+H)$^+$, found 354.9809.

7c: $^1$H NMR (500 MHz, DMSO-d$_6$) δ 10.74 (s, 1H), 10.37 (s, 1H), 7.87 (s, 1H), 7.32 (s, 1H), 7.20 (d, J=8.2 Hz, 1H), 7.07 (d, J=2.3 Hz, 1H), 6.88 (dd, J=8.2, 1.4 Hz, 1H), 4.29 (t, J=4.4 Hz, 1H), 3.05 (dd, J=14.0, 3.7 Hz, 1H), 3.01 (dd, J=14.1, 4.5 Hz, 1H), 2.37 (s, 3H); $^{13}$C NMR (126 MHz, DMSO-d$_6$) δ 176.24, 157.87, 134.73, 128.17, 127.10, 124.60, 122.91, 118.61, 111.41, 107.94, 58.81, 27.04, 21.83; ESI-MS m/z 244.2 (M+H)$^+$; MALDI-HRMS m/z calcd for C$_{13}$H$_{14}$N$_3$O$_2$ (M)$^+$243.1016, found 244.1080.

7d: $^1$H NMR (500 MHz, DMSO-d$_6$) δ 11.48 (s, 1H), 10.36 (s, 1H), 7.90 (s, 1H), 7.53 (d, J=8.5 Hz, 1H), 7.24 (d, J=1.4 Hz, 1H), 7.17 (d, J=8.5 Hz, 1H), 4.33 (t, J=4.4 Hz, 1H), 3.09 (dd, J=15.4, 5.3 Hz, 1H), 3.05 (dd, J=15.5, 4.9 Hz, 1H); $^{13}$C NMR (126 MHz, DMSO-d$_6$) δ 176.05, 157.80, 134.01, 128.41, 126.94, 123.91, 120.62, 119.20, 114.34, 110.32, 58.58, 26.67; ESI-MS m/z 296.0 (M-H)$^-$; ESI-HRMS m/z calcd for C$_{12}$H$_8$Cl$_2$N$_3$O$_2$ (M-H)$^-$ 295.9999, found 295.9999.

7e: $^1$H NMR (500 MHz, DMSO-d$_6$) δ 11.52 (s, 1H), 10.39 (s, 1H), 7.92 (s, 1H), 7.61 (d, J=1.7 Hz, 1H), 7.28 (d, J=2.5 Hz, 1H), 7.20 (d, J=1.8 Hz, 1H), 4.34 (t, J=4.7 Hz, 1H), 3.11 (dd, J=14.9, 4.8 Hz, 1H), 3.05 (dd, J=15.0, 4.5 Hz, 1H); $^{13}$C NMR (126 MHz, DMSO-d$_6$) δ 176.12, 157.81, 131.89, 130.40, 127.86, 123.66, 120.47, 117.91, 116.89, 109.86, 58.65, 26.58; ESI-MS m/z 298.1 (M+H)$^+$; MALDI-HRMS m/z calcd for $C_{12}H_9Cl_2N_3O_2$ (M)$^+$297.0072, found 297.0065.

7f: $^1$H NMR (500 MHz, DMSO-d$_6$) δ 11.65 (s, 1H), 10.61 (s, 1H), 7.89 (s, 1H), 7.34 (d, J=2.1 Hz, 1H), 7.12 (d, J=8.1 Hz, 1H), 7.01 (d, J=8.1 Hz, 1H), 4.33 (ddd, J=8.3, 4.4, 1.0 Hz, 1H), 3.49 (dd, J=14.8, 4.3 Hz, 1H), 3.11 (dd, J=14.9, 8.4 Hz, 1H); $^{13}$C NMR (126 MHz, DMSO-d$_6$) δ 175.89, 157.93, 134.66, 127.86, 125.35, 124.11, 121.50, 120.66, 115.60, 111.02, 59.34, 28.85; ESI-MS m/z 298.1 (M+H)$^+$; MALDI-HRMS m/z calcd for $C_{12}H_9Cl_2N_3O_2$ (M)$^+$297.0072, found 297.0066.

7g: $^1$H NMR (400 MHz, DMSO-d$_6$) δ 11.45 (s, 1H), 10.37 (s, 1H), 7.90 (s, 1H), 7.52 (dd, J=8.7, 4.7 Hz, 1H), 7.21 (d, J=2.4 Hz, 1H), 7.03 (dd, J=10.2, 8.8 Hz, 1H), 4.33 (t, J=4.5 Hz, 1H), 3.06 (dd, J=4.4, 3.1 Hz, 2H); $^{13}$C NMR (126 MHz, DMSO-d$_6$) δ 176.08, 157.82, 155.12, 153.23, 133.46, 126.06, 118.75, 110.09, 108.18, 102.27, 58.58, 26.67; ESI-MS m/z 282.4 (M+H)$^+$; MALDI-HRMS m/z calcd for $C_{12}H_9ClFN_3O_2$(M)$^+$ 281.0367, found 281.0361.

7h: $^1$H NMR (500 MHz, DMSO-d$_6$) δ 11.41 (s, 1H), 10.38 (s, 1H), 7.91 (s, 1H), 7.35 (dd, J=9.7, 2.2 Hz, 1H), 7.27 (d, J=2.5 Hz, 1H), 7.11 (dd, J=9.2, 2.3 Hz, 1H), 4.33 (t, J=4.5 Hz, 1H), 3.09 (dd, J=14.9, 4.8 Hz, 1H), 3.03 (dd, J=15.0, 4.5 Hz, 1H); $^{13}$C NMR (126 MHz, DMSO-d$_6$) δ 176.16, 157.80, 155.52, 130.17, 129.38, 128.12, 116.21, 110.19, 109.67, 103.59, 58.65, 26.67; ESI-MS m/z 282.4 (M+H)$^+$; MALDI-HRMS m/z calcd for $C_{12}H_9ClFN_3O_2$(M)$^+$ 281.0367, found 281.0361.

7i: $^1$H NMR (500 MHz, DMSO-d$_6$) δ 11.57 (s, 1H), 10.53 (s, 1H), 7.89 (s, 1H), 7.24 (d, J=2.3 Hz, 1H), 7.10 (dd, J=8.3, 4.1 Hz, 1H), 6.77 (dd, J=10.8, 8.3 Hz, 1H), 4.29 (ddd, J=7.2, 4.4, 1.0 Hz, 1H), 3.22 (dd, J=14.8, 4.3 Hz, 1H), 3.05 (dd, J=14.8, 7.4 Hz, 1H); $^{13}$C NMR (126 MHz, DMSO-d$_6$) δ 175.81, 157.93, 154.78, 135.62, 126.22, 121.10, 117.67, 111.87, 109.07, 105.32, 58.97, 28.54; ESI-MS m/z 282.3 (M+H)$^+$; MALDI-HRMS m/z calcd for $C_{12}H_9ClFN_3O_2$ (M)$^+$ 281.0367, found 281.0850.

Example 5

Exemplary Preparations of Compound 1

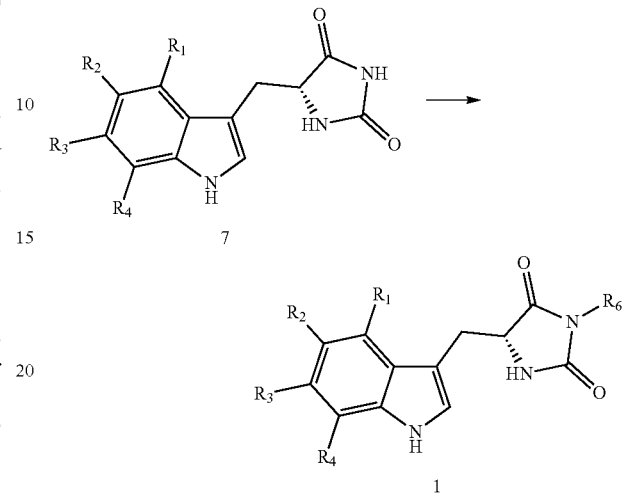

To a solution of compound 7 (1 mmol) in 2 mL DMSO, the alkylation reagent (L-R$^6$, 1.5 equiv) and potassium carbonate (1.5 equiv) was added. The reaction mixture was allowed to stir at room temperature for 2-2.5 h until TLC detected the reaction was complete (eluting with DCM: MeOH=10:1). After quenching the reaction with 5 mL water, the reaction mixture was extracted with ethylacetate (5 mL×3). The combined organic phases were dried over anhydrous Na$_2$SO$_4$. After filtrating and concentrating in vacuum, compound 1 was obtained by column chromatography.

Table 4 provides exemplary compounds and conditions for preparation of compounds of structure (1) according to the above general procedure.

TABLE 4

Exemplary Preparations of Compound (1)

| entry | 7 | 8 (L—R$^6$) | 1 | yield % |
|---|---|---|---|---|
| 1 | 7a | CH$_3$I | 1aa | 80 |
| 2 | 7b | CH$_3$I | 1ba | 82 |

TABLE 4-continued
Exemplary Preparations of Compound (1)
| entry | 7 | 8 (L—R⁶) | 1 | yield % |
|---|---|---|---|---|
| 3 | 7c | CH₃I | 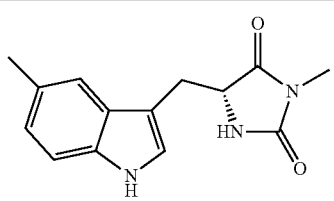 1ca | 81 |
| 4 | 7d | CH₃I | 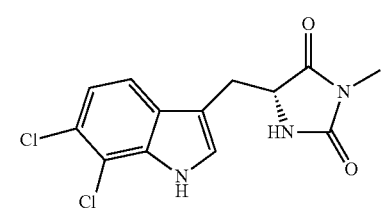 1da | 74 |
| 5 | 7e | CH₃I | 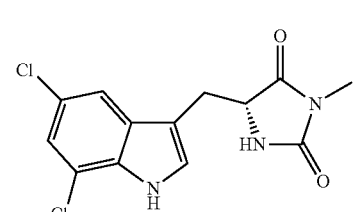 1ea | 78 |
| 6 | 7f | CH₃I | 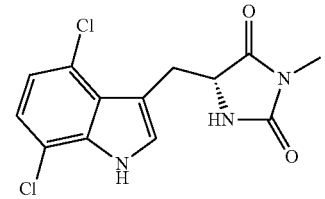 1fa | 75 |
| 7 | 7g | CH₃I | 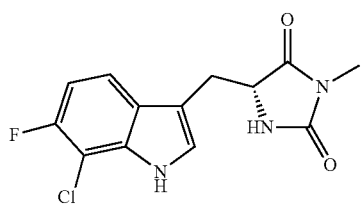 1ga | 75 |
| 8 | 7h | CH₃I | 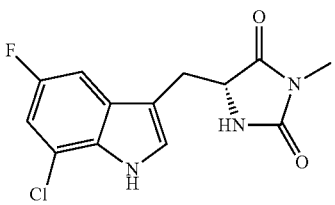 1ha | 78 |

TABLE 4-continued

Exemplary Preparations of Compound (1)

| entry | 7 | 8 (L—R⁶) | 1 | yield % |
|---|---|---|---|---|
| 9 | 7i | CH₃I | 1ia | 74 |
| 10 | 7a | allyl bromide | 1ab | 82 |
| 11 | 7a | isopropyl bromide | 1ac | 80 |
| 12 | 7a | (bromomethyl)cyclopentane | 1ad | 61 |
| 13 | 7a | (bromomethyl)cyclopropane | 1ae | 45 |
| 14 | 7a | Br-(CH₂)₃-Ph | 1af | 65 |

TABLE 4-continued
Exemplary Preparations of Compound (1)
| entry | 7 | 8 (L—R⁶) | 1 | yield % |
|---|---|---|---|---|
| 15 | 7a | 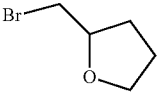 | 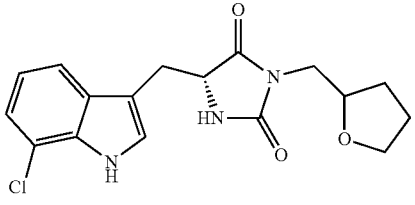 1ag | 48 |
| 16 | 7a | 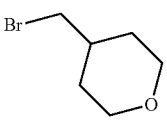 | 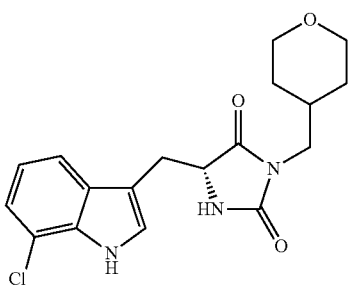 1ah | 62 |
| 17 | 7a | 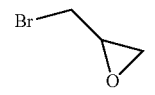 | 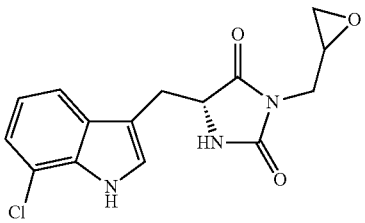 1ai | 55 |
| 18 | 7a | 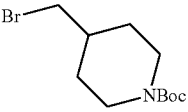 | 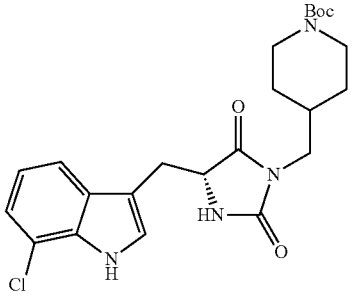 1aj | 50 |
| 19 | 7a | 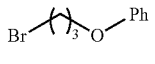 | 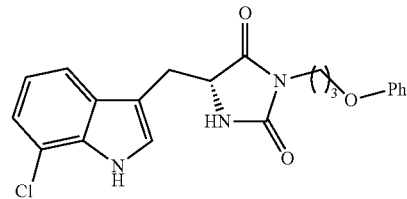 1ak | 65 |

TABLE 4-continued
Exemplary Preparations of Compound (1)
| entry | 7 | 8 (L—R⁶) | 1 | yield % |
|---|---|---|---|---|
| 20 | 7g | 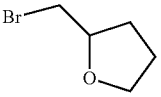 | 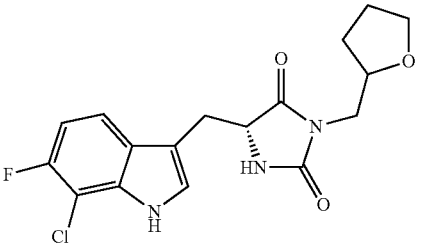<br>1gg | 45 |
| 21 | 7a | 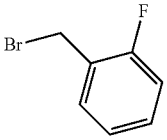 | 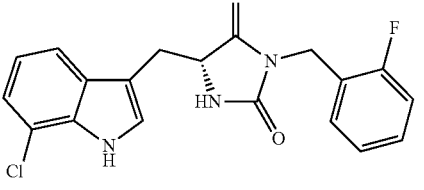<br>1al | 77 |
| 22 | 7a | 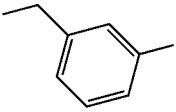 | 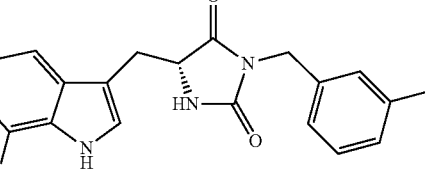<br>1am | 70 |
| 23 | 7a | 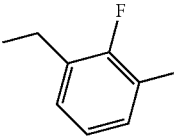 | 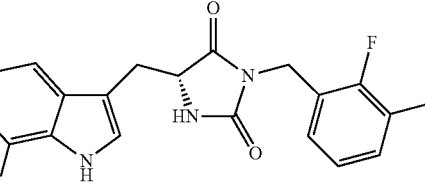<br>1an | 74 |
| 24 | 7a | 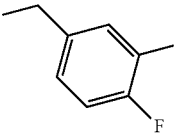 | 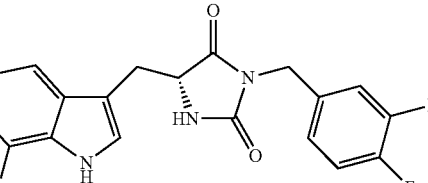<br>1ao | 80 |
| 25 | 7a | 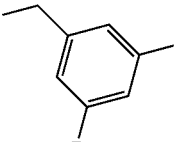 | 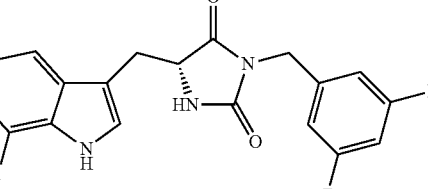<br>1ap | 76 |

TABLE 4-continued
Exemplary Preparations of Compound (1)
| entry | 7 | 8 (L—R⁶) | 1 | yield % |
|---|---|---|---|---|
| 26 | 7a | 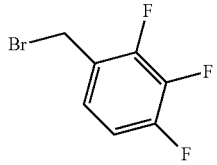 [SMILES: Fc1ccc(CBr)c(F)c1F] | 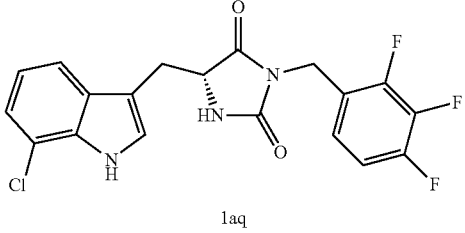 [SMILES: O=C1N[C@H](Cc2c[nH]c3c(Cl)cccc23)C(=O)N1Cc1ccc(F)c(F)c1F ; "1aq"] 1aq | 69 |
| 27 | 7a | 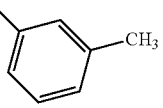 | 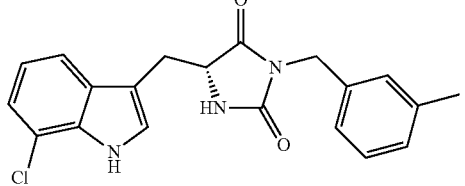 1ar | 70 |
| 28 | 7a | 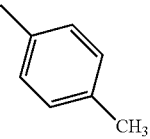 | 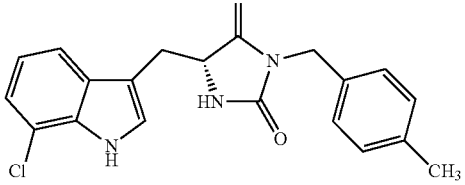 1as | 63 |
| 29 | 7a | 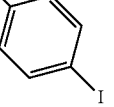 | 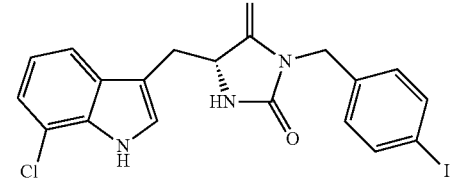 1at | 60 |
| 30 | 7a | 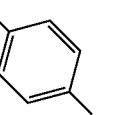 | 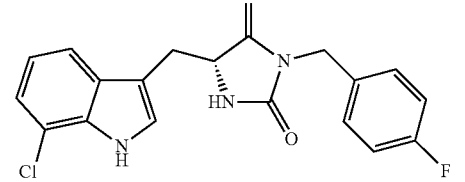 1au | 63 |
| 31 | 7a | 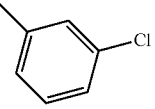 | 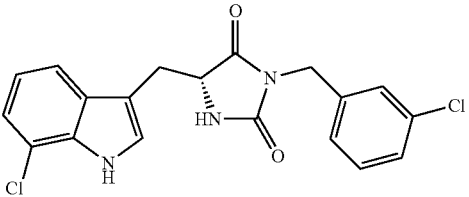 1av | 71 |

TABLE 4-continued

Exemplary Preparations of Compound (1)

| entry | 7 | 8 (L—R⁶) | 1 | yield % |
|---|---|---|---|---|
| 32 | 7a | 4-phenylbenzyl bromide | 1aw | 65 |
| 33 | 7a | 2-chloro-4-fluorobenzyl bromide | 1ax | 75 |
| 34 | 7a | 2-fluoro-3-(trifluoromethyl)benzyl bromide | 1ay | 78 |
| 35 | 7a | 2-chloro-5-(trifluoromethyl)benzyl bromide | 1az | 78 |
| 36 | 7a | 4-(bromomethyl)pyridine | 1aaa | 35 |
| 37 | 7g | 2-fluorobenzyl bromide | 1gl | 75 |

TABLE 4-continued
Exemplary Preparations of Compound (1)
| entry | 7 | 8 (L—R⁶) | 1 | yield % |
|---|---|---|---|---|
| 38 | 7g | 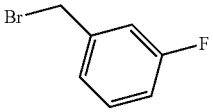 | 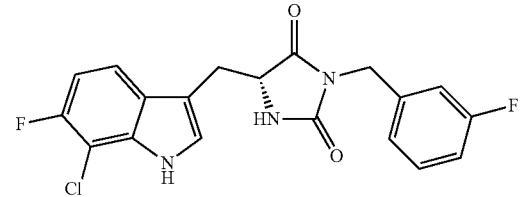 1gm | 71 |
| 39 | 7g | 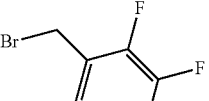 | 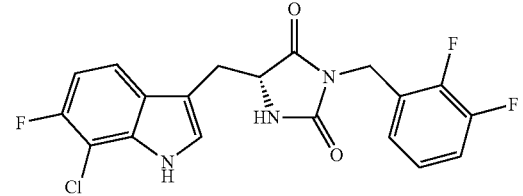 1gn | 74 |
| 40 | 7g | 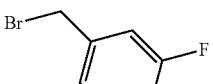 | 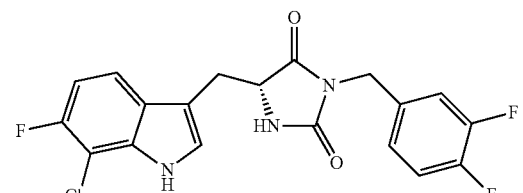 1go | 78 |
| 41 | 7g | 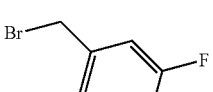 | 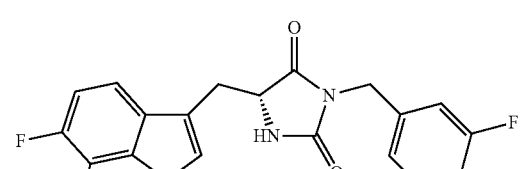 1gp | 74 |
| 42 | 7g | 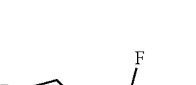 | 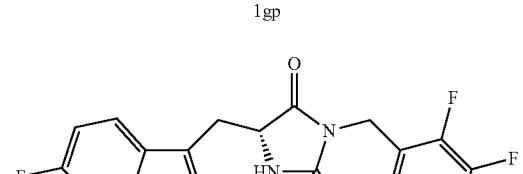 1gp | 75 |
| 43 | 7g |  | 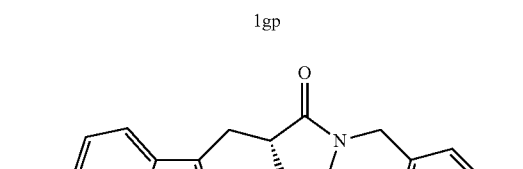 1gu | 68 |

TABLE 4-continued

Exemplary Preparations of Compound (1)

| entry | 7 | 8 (L—R⁶) | 1 | yield % |
|---|---|---|---|---|
| 44 | 7g | 3-chlorobenzyl bromide | 1gv | 72 |

Compounds of structure 1 from Table 4 were analyzed by NMR and mass spectrometry. Data is provided below:

1aa: $^1$H NMR (500 MHz, DMSO-d$_6$) δ 11.29 (s, 1H), 8.20 (s, 1H), 7.54 (d, J=7.9 Hz, 1H), 7.24 (s, 1H), 7.15 (d, J=7.5 Hz, 1H), 6.99 (t, J=7.7 Hz, 1H), 4.38 (t, J=4.8 Hz, 1H), 3.17 (dd, J=14.9, 4.3 Hz, 1H), 3.10 (dd, J=14.9, 5.8 Hz, 1H), 2.67 (s, 3H); $^{13}$C NMR (126 MHz, DMSO-d$_6$) δ 174.56, 157.43, 133.20, 129.85, 125.96, 120.93, 119.86, 118.12, 116.22, 109.99, 57.56, 27.20, 24.30; ESI-MS m/z 300.1 (M+Na)$^+$; ESI-HRMS m/z calcd for C$_{13}$H$_{12}$ClN$_3$NaO$_2$$^+$(M+Na)$^+$ 300.0510, found 300.0520.

1ba: $^1$H NMR (500 MHz, DMSO-d$_6$) δ 10.86 (s, 1H), 8.22 (s, 1H), 7.54 (dd, J=17.0, 7.5 Hz, 1H), 7.45 (d, J=7.4 Hz, 1H), 7.17 (d, J=2.5 Hz, 1H), 6.79 (t, J=7.7 Hz, 1H), 4.36 (t, J=5.1 Hz, 1H), 3.10 (dd, J=14.9, 4.6 Hz, 1H), 3.04 (dd, J=14.9, 5.6 Hz, 1H), 2.63 (s, 3H); $^{13}$C NMR (126 MHz, DMSO-d$_6$) δ 174.56, 157.34, 138.05, 130.29, 128.43, 125.69, 120.80, 119.18, 109.99, 77.36, 57.48, 27.21, 24.31; ESI-MS m/z 392.2 (M+Na)$^+$; ESI-HRMS m/z calcd for C1$_3$H1$_2$IN$_3$NaO$_2$ (M+Na)$^+$ 391.9866, found 391.9861.

1ca: $^1$H NMR (400 MHz, DMSO-d$_6$) δ 10.85 (s, 1H), 8.20 (s, 1H), 7.30 (s, 1H), 7.21 (d, J=8.2 Hz, 1H), 7.06 (d, J=2.1 Hz, 1H), 6.87 (d, J=8.2 Hz, 1H), 4.32 (t, J=4.8 Hz, 1H), 3.11 (dd, J=14.9, 4.4 Hz, 1H), 3.00 (dd, J=14.9, 5.9 Hz, 1H), 2.67 (s, 3H), 2.37 (s, 3H); $^{13}$C NMR (126 MHz, DMSO-d$_6$) δ 174.68, 157.40, 134.76, 128.06, 127.06, 124.50, 122.90, 118.43, 111.47, 107.92, 57.68, 27.26, 24.30, 21.79; ESI-MS m/z 280.3 (M+Na)$^+$; ESI-HRMS m/z calcd for C$_{14}$H$_{15}$N$_3$NaO$_2$ (M+Na)$^+$ 280.1056, found 280.1060.

1da: $^1$H NMR (400 MHz, DMSO-d$_6$) δ 11.48 (s, 1H), 8.18 (s, 1H), 7.52 (d, J=8.5 Hz, 1H), 7.23 (d, J=2.5 Hz, 1H), 7.18 (d, J=8.5 Hz, 1H), 4.37 (t, J=5.7 Hz, 1H), 3.11 (dd, J=15.2, 4.8 Hz, 1H), 3.05 (dd, J=15.0, 5.7 Hz, 1H), 2.63 (s, 3H); $^{13}$C NMR (126 MHz, DMSO-d$_6$) δ 174.46, 157.34, 134.06, 128.28, 126.89, 123.94, 120.62, 119.04, 114.35, 110.39, 57.45, 26.92, 24.29; ESI-MS m/z 334.2 (M+Na)$^+$; ESI-HRMS m/z calcd for C$_{13}$H$_{11}$C$_{12}$N$_3$NaO$_2$ (M+Na)$^+$ 334.0121, found 334.0108.

1ea: $^1$H NMR (500 MHz, DMSO-d$_6$) δ 11.52 (s, 1H), 8.17 (s, 1H), 7.59 (d, J=1.8 Hz, 1H), 7.25 (s, 1H), 7.22 (d, J=1.8 Hz, 1H), 4.36 (t, J=5.1 Hz, 1H), 3.09 (dd, J=15.2, 4.9 Hz, 1H), 3.05 (dd, J=15.1, 5.6 Hz, 1H), 2.64 (s, 3H); $^{13}$C NMR (126 MHz, DMSO-d$_6$) δ 174.48, 157.32, 131.91, 130.31, 127.70, 123.60, 120.50, 117.78, 116.87, 110.02, 57.49, 26.83, 24.28; ESI-MS m/z 334.2 (M+Na)$^+$; ESI-HRMS m/z calcd for C$_{13}$H$_{11}$C$_{12}$N$_3$NaO$_2$ (M+Na)$^+$ 334.0121, found 334.0130.

1fa: $^1$H NMR (400 MHz, DMSO-d$_6$) δ 11.69 (s, 1H), 8.18 (s, 1H), 7.34 (d, J=2.5 Hz, 1H), 7.16 (d, J=8.1 Hz, 1H), 7.04 (d, J=8.1 Hz, 1H), 4.35 (t, J=4.9 Hz, 1H), 3.50 (dd, J=14.8, 4.0 Hz, 1H), 3.04 (dd, J=14.8, 8.9 Hz, 1H), 2.81 (s, 3H); $^{13}$C NMR (126 MHz, DMSO-d$_6$) δ 174.26, 157.50, 134.70, 127.93, 125.32, 124.04, 121.54, 120.65, 115.61, 110.99, 58.23, 28.97, 24.44; ESI-MS m/z 334.2 (M+Na)$^+$; ESI-HRMS m/z calcd for C$_{13}$H$_{11}$C$_{12}$N$_3$NaO$_2$ (M+Na)$^+$ 334.0121, found 334.0109.

1ga: $^1$H NMR (500 MHz, DMSO-d$_6$) δ 11.48 (s, 1H), 8.22 (d, J=10.6 Hz, 1H), 7.50 (dd, J=8.7, 4.7 Hz, 1H), 7.20 (d, J=2.4 Hz, 1H), 7.02 (dd, J=10.1, 8.7 Hz, 1H), 4.35 (t, J=5.6 Hz, 1H), 3.11 (dd, J=15.0, 4.6 Hz, 1H), 3.05 (dd, J=14.9, 5.6 Hz, 1H), 2.62 (s, 3H); $^{13}$C NMR (126 MHz, DMSO-d$_6$) δ 174.52, 157.33, 155.10, 153.22, 133.52, 126.45, 118.66, 110.08, 108.33, 102.45, 57.44, 26.89, 24.27; ESI-MS m/z 318.1 (M+Na)$^+$; ESI-HRMS m/z calcd for C$_{13}$H$_{11}$ClFN$_3$NaO$_2$ (M+Na)$^+$ 318.0416, found 318.0428. Chiral HPLC: 98.9 enantiomeric excess.

1ha: $^1$H NMR (400 MHz, DMSO-d$_6$) δ 11.41 (s, 1H), 8.18 (s, 1H), 7.34 (dd, J=9.8, 2.1 Hz, 1H), 7.26 (d, J=2.2 Hz, 1H), 7.14 (dd, J=9.2, 2.1 Hz, 1H), 4.38 (t, J=4.7 Hz, 1H), 3.09 (dd, J=14.6, 4.2 Hz, 1H), 3.05 (dd, J=14.7, 5.1 Hz, 1H), 2.64 (s, 3H); $^{13}$C NMR (126 MHz, DMSO-d$_6$) δ 174.50, 157.35, 155.49, 130.18, 129.27, 127.95, 116.18, 110.35, 109.73, 103.44, 57.48, 26.93, 24.27; ESI-MS m/z 318.2 (M+Na)$^+$; ESI-HRMS m/z calcd for C$_{13}$H$_{11}$ClFN$_3$NaO$_2$ (M+Na)$^+$ 318.0416, found 318.0418.

1ia: $^1$H NMR (400 MHz, DMSO-d$_6$) δ 11.63 (s, 1H), 8.21 (s, 1H), 7.24 (d, J=2.2 Hz, 1H), 7.12 (dd, J=8.3, 4.1 Hz, 1H), 6.78 (dd, J=10.9, 8.3 Hz, 1H), 4.35-4.27 (m, 1H), 3.26 (dd, J=14.7, 4.2 Hz, 1H), 3.00 (dd, J=14.8, 8.0 Hz, 1H), 2.76 (s, 3H); $^{13}$C NMR (126 MHz, DMSO-d$_6$) δ 174.21, 157.47, 154.74, 135.66, 126.28, 121.12, 111.85, 109.05, 105.30, 105.13, 57.85, 28.71, 24.40; ESI-MS m/z 318.2 (M+Na)$^+$; ESI-HRMS m/z calcd for C$_{13}$H$_{11}$ClFN$_3$NaO$_2$ (M+Na)$^+$ 318.0416, found 318.0420.

1ab: $^1$H NMR (400 MHz, DMSO-d$_6$) δ 11.29 (s, 1H), 8.26 (s, 1H), 7.54 (d, J=7.9 Hz, 1H), 7.21 (d, J=2.4 Hz, 1H), 7.14 (d, J=7.4 Hz, 1H), 6.99 (t, J=7.8 Hz, 1H), 5.40 (ddt, J=17.2, 10.1, 4.9 Hz, 1H), 4.78 (dd, J=10.4, 1.3 Hz, 1H), 4.50 (dd, J=17.2, 1.3 Hz, 1H), 4.43 (t, J=4.6 Hz, 1H), 3.83-3.67 (m, 2H), 3.16 (dd, J=13.5, 3.3 Hz, 1H), 3.11 (dd, J=16.3, 4.5 Hz, 1H); $^{13}$C NMR (126 MHz, DMSO-d$_6$) δ 174.00, 156.80, 133.15, 132.27, 132.20, 129.91, 126.15, 126.10, 120.85, 119.83, 118.32, 116.10, 115.91, 109.53, 26.95; ESI-MS m/z 326.3 (M+Na)$^+$; ESI-HRMS m/z calcd for C$_{15}$H$_{14}$ClN$_3$NaO$_2$ (M+Na)$^+$ 326.06767, found 326.0676.

1ac: $^1$H NMR (400 MHz, DMSO-d$_6$) δ 11.27 (s, 1H), 8.10 (s, 1H), 7.51 (d, J=7.9 Hz, 1H), 7.18 (d, J=2.4 Hz, 1H), 7.12 (d, J=7.4 Hz, 1H), 6.97 (t, J=7.8 Hz, 1H), 4.26 (t, J=4.3 Hz, 1H), 3.88-3.78 (m, 1H), 3.13 (dd, J=14.8, 4.5 Hz, 1H), 3.05 (dd, J=14.8, 4.3 Hz, 1H), 0.96 (d, J=6.9 Hz, 3H), 0.89 (d,

J=6.9 Hz, 3H); $^{13}$C NMR (126 MHz, DMSO-d$_6$) δ 174.41, 157.06, 133.04, 129.88, 126.21, 120.80, 119.77, 118.40, 115.95, 109.11, 56.51, 42.27, 26.91, 19.46; ESI-MS m/z 328.3 (M+Na)+; ESI-HRMS m/z calcd for C$_{15}$H$_{16}$ClN$_3$NaO$_2$ (M+Na)$^+$ 328.0823, found 328.0829.

1ad: $^1$H NMR (400 MHz, DMSO-d$_6$) δ 11.25 (s, 1H), 8.18 (s, 1H), 7.51 (d, J=7.9 Hz, 1H), 7.18 (d, J=2.4 Hz, 1H), 7.11 (d, J=7.1 Hz, 1H), 6.96 (t, J=7.8 Hz, 1H), 4.34 (t, J=4.2 Hz, 1H), 3.17 (dd, J=14.8, 4.4 Hz, 1H), 3.11-3.01 (m, 2H), 2.94 (dd, J=13.4, 8.3 Hz, 1H), 1.57 (dt, J=14.9, 7.5 Hz, 1H), 1.41-1.28 (m, 2H), 1.20 (tdd, J=12.2, 9.4, 3.8 Hz, 3H), 0.88-0.62 (m, 3H): $^{13}$C NMR (126 MHz, DMSO-d$_6$) 174.45, 157.44, 133.12, 129.85, 126.30, 120.73, 119.74, 118.39, 116.04, 109.07, 57.06, 42.21, 38.61, 29.59, 26.63, 24.56: ESI-MS m/z 368.3 (M+Na)$^+$; ESI-HRMS m/z calcd for C$_{18}$H$_{20}$ClN$_3$NaO$_2$ (M+Na)$^+$ 368.1136, found 368.1145.

1ae: $^1$H NMR (400 MHz, DMSO-d$_6$) δ 11.32 (s, 1H), 8.24 (s, 1H), 7.58 (dd, J=7.8, 4.8 Hz, 1H), 7.25 (d, J=2.3 Hz, 1H), 7.18 (dd, J=7.3, 4.0 Hz, 1H), 7.03 (dd, J=7.8, 3.7 Hz, 1H), 5.40 (ddt, J=17.5, 10.9, 6.8 Hz, 1H), 4.84 (dd, J=13.0, 6.1 Hz, 2H), 4.41 (t, J=4.8 Hz, 1H), 3.32-3.03 (m, 4H), 1.88 (tt, J=14.4, 7.1 Hz, 2H); $^{13}$C NMR (126 MHz, DMSO-d$_6$) δ 174.53, 157.36, 135.02, 133.12, 129.82, 126.17, 120.82, 119.84, 118.28, 116.91, 116.10, 109.27, 57.18, 37.09, 31.78, 26.83; ESI-MS m/z 340.3 (M+Na)$^+$; ESI-HRMS m/z calcd for C$_{16}$H$_{16}$ClN$_3$NaO$_2$ (M+Na)$^+$ 340.0823, found 340.0811.

1af: $^1$H NMR (400 MHz, DMSO-d$_6$) δ 11.29 (s, 1H), 8.19 (s, 1H), 7.53 (d, J=7.9 Hz, 1H), 7.26-7.19 (m, 3H), 7.14 (dd, J=7.3, 4.5 Hz, 2H), 7.05 (d, J=7.1 Hz, 2H), 6.98 (t, J=7.8 Hz, 1H), 4.36 (t, J=4.4 Hz, 1H), 3.23-3.02 (m, 4H), 2.31 (dt, J=10.0, 6.6 Hz, 2H), 1.13-0.96 (m, 4H); $^{13}$C NMR (126 MHz, DMSO-d$_6$) δ 174.40, 157.30, 142.31, 133.14, 129.89, 128.65, 126.27, 126.21, 126.02, 120.85, 119.80, 118.27, 116.14, 109.31, 57.16, 37.46, 34.90, 28.07, 27.28, 26.90; ESI-MS m/z 418.4 (M+Na)$^+$; ESI-HRMS m/z calcd for C$_{22}$H$_{22}$ClN$_3$NaO$_2$ (M+Na)$^+$ 418.1293, found 418.1284.

1ag (i.e., "Ia"): $^1$H NMR (400 MHz, DMSO-d$_6$) δ 11.28 (s, 1H), 8.22 (d, J=4.0 Hz, 1H), 7.51 (dd, J=7.9, 3.6 Hz, 1H), 7.19 (d, J=2.2 Hz, 1H), 7.13 (d, J=7.4 Hz, 1H), 6.98 (dd, J=7.8, 2.4 Hz, 1H), 4.40-4.33 (m, 1H), 3.67-3.51 (m, 2H), 3.51-3.39 (m, 1H), 3.31-2.93 (m, 5H), 1.60 (ddd, J=37.4, 21.3, 6.9 Hz, 2H), 1.00 (dd, J=13.4, 5.5 Hz, 1H); $^{13}$C NMR (126 MHz, DMSO-d$_6$) δ 174.54, 157.18, 133.11, 129.76, 126.34, 120.82, 119.87, 118.28, 116.07, 100.00, 75.23, 67.36, 57.09, 41.35, 28.54, 26.73, 24.92; ESI-MS m/z 370.3 (M+Na)$^+$; ESI-HRMS m/z calcd for C$_{17}$H$_{18}$ClN$_3$NaO$_3$ (M+Na)$^+$ 370.0929, found 370.0935.

1ah: $^1$H NMR (400 MHz, DMSO-d$_6$) δ 11.26 (s, 1H), 8.25 (s, 1H), 7.53 (d, J=7.9 Hz, 1H), 7.17 (d, J=2.4 Hz, 1H), 7.12 (d, J=7.2 Hz, 1H), 6.98 (t, J=7.8 Hz, 1H), 4.36 (t, J=3.8 Hz, 1H), 3.55 (dd, J=13.4, 2.4 Hz, 1H), 3.49 (dd, J=11.4, 2.5 Hz, 1H), 3.21 (dd, J=14.8, 3.9 Hz, 1H), 3.04 (dd, J=11.4, 3.4 Hz, 1H), 2.99 (t, J=8.4 Hz, 1H), 2.85 (ddd, J=14.2, 7.8, 3.2 Hz, 2H), 2.70 (ddd, J=11.7, 10.1, 1.9 Hz, 1H), 1.15 (ddd, J=10.8, 9.2, 5.5 Hz, 1H), 0.81-0.60 (m, 3H), 0.39 (d, J=11.6 Hz, 1H); $^{13}$C NMR (126 MHz, DMSO-d$_6$) δ 174.25, 157.30, 132.96, 129.88, 126.39, 120.79, 119.82, 118.48, 116.04, 108.99, 66.77, 57.14, 43.22, 33.61, 30.02, 26.47; ESI-MS m/z 384.4 (M+Na)$^+$; ESI-HRMS m/z calcd for C$_{18}$H$_{20}$ClN$_3$NaO$_3$ (M+Na)$^+$ 384.1085, found 384.1096.

1ai: $^1$H NMR (400 MHz, DMSO-d$_6$) δ 11.29 (s, 1H), 8.28 (s, 1H), 7.52 (d, J=7.9 Hz, 1H), 7.20 (dd, J=5.9, 2.4 Hz, 1H), 7.14 (d, J=7.6 Hz, 1H), 6.99 (t, J=7.8 Hz, 1H), 4.42 (t, J=4.8 Hz, 1H), 3.47-3.38 (m, 1H), 3.20 (ddd, J=27.7, 14.4, 5.0 Hz, 1H), 3.12 (d, J=4.6 Hz, 2H), 2.69-2.59 (m, 1H), 2.41-2.34 (m, 1H), 2.15 (ddd, J=12.9, 5.0, 2.5 Hz, 1H); $^{13}$C NMR (126 MHz, DMSO-d$_6$) δ 174.27, 156.81, 133.14, 129.87, 126.07, 120.86, 119.84, 118.21, 116.09, 109.47, 57.44, 48.70, 48.50, 45.21, 27.04; ESI-MS m/z 342.2 (M+Na)$^+$; ESI-HRMS m/z calcd for C$_{15}$H$_{14}$ClN$_3$NaO$_3$ (M+Na)$^+$ 342.0616, found 342.0611.

1aj: $^1$H NMR (400 MHz, DMSO-d$_6$) δ 11.28 (s, 1H), 8.26 (s, 1H), 7.54 (d, J=7.9 Hz, 1H), 7.18 (d, J=2.2 Hz, 1H), 7.12 (d, J=7.4 Hz, 1H), 6.98 (t, J=7.8 Hz, 1H), 4.36 (t, J=3.8 Hz, 1H), 3.63 (s, 2H), 3.22 (dd, J=14.8, 3.8 Hz, 1H), 3.10-2.94 (m, 2H), 2.84 (dd, J=13.5, 8.4 Hz, 1H), 2.26 (s, 1H), 2.16-2.04 (m, 1H), 1.36 (s, 9H), 1.11 (s, 1H), 0.49 (s, 4H); $^{13}$C NMR (126 MHz, DMSO-d$_6$) δ 174.23, 157.27, 154.12, 132.95, 129.89, 126.40, 120.79, 119.83, 118.48, 116.08, 108.97, 78.80, 57.13, 42.95, 34.50, 29.16, 29.00, 28.52, 26.44; ESI-MS m/z 483.5 (M+Na)$^+$; ESI-HRMS m/z calcd for C$_{23}$H$_{29}$ClN$_4$NaO$_4$ (M+Na)$^+$ 483.1769, found 483.1786.

1ak: $^1$H NMR (500 MHz, DMSO-d$_6$) δ 11.31 (s, 1H), 8.19 (s, 1H), 7.52 (d, J=7.9 Hz, 1H), 7.24 (dd, J=8.4, 7.5 Hz, 2H), 7.19 (d, J=2.3 Hz, 1H), 7.13 (d, J=7.5 Hz, 1H), 6.98 (t, J=7.8 Hz, 1H), 6.89 (t, J=7.3 Hz, 1H), 6.73 (d, J=8.0 Hz, 2H), 4.35 (t, J=4.5 Hz, 1H), 3.47-3.38 (m, 1H), 3.32-3.26 (m, 3H), 3.15 (dd, J=14.8, 4.7 Hz, 1H), 3.08 (dd, J=14.9, 4.4 Hz, 1H), 1.52 (dd, J=12.4, 6.7 Hz, 1H), 1.42 (dd, J=12.2, 6.7 Hz, 1H); $^{13}$C NMR (126 MHz, DMSO-d$_6$) δ 174.48, 158.83, 157.17, 133.12, 129.83, 129.80, 126.27, 120.90, 120.82, 119.87, 118.33, 116.17, 114.70, 109.35, 64.54, 57.17, 34.97, 27.59, 26.98; ESI-MS m/z 420.4 (M+Na)$^+$; ESI-HRMS m/z calcd for C$_{21}$H$_{20}$ClN$_3$NaO$_3$ (M+Na)$^+$ 420.1085, found 420.1066.

1al: $^1$H NMR (400 MHz, DMSO-d$_6$) δ 11.35 (s, 1H), 8.44 (s, 1H), 7.57 (d, J=7.9 Hz, 1H), 7.22 (d, J=2.5 Hz, 1H), 7.18 (d, J=7.8 Hz, 1H), 7.15 (d, J=7.3 Hz, 1H), 7.06 (t, J=5.7 Hz, 1H), 6.97 (t, J=7.8 Hz, 1H), 6.72 (dd, J=7.6, 0.9 Hz, 1H), 5.86 (dd, J=7.8, 1.2 Hz, 1H), 4.52 (t, J=4.1 Hz, 1H), 4.41 (d, J=16.2 Hz, 1H), 4.33 (d, J=16.2 Hz, 1H), 3.25 (dd, J=14.9, 4.5 Hz, 1H), 3.13 (dd, J=14.9, 4.2 Hz, 1H); $^{13}$C NMR (126 MHz, DMSO-d$_6$) δ 174.04, 160.80, 158.85, 156.64, 133.13, 129.95, 129.26, 127.76, 126.36, 124.38, 123.46, 120.93, 119.97, 118.43, 116.16, 115.41, 109.28, 57.75, 26.53; ESI-MS m/z 394.3 (M+Na)$^+$; ESI-HRMS m/z calcd for C$_{19}$H$_{15}$ClFN$_3$NaO$_2$ (M+Na)$^+$ 394.0729, found 394.0735.

1am: $^1$H NMR (400 MHz, DMSO-d$_6$) δ 11.33 (s, 1H), 8.44 (s, 1H), 7.59 (d, J=7.9 Hz, 1H), 7.23 (d, J=2.4 Hz, 1H), 7.18 (d, J=7.4 Hz, 1H), 7.09 (dd, J=14.3, 8.1 Hz, 1H), 7.01 (dd, J=13.4, 5.6 Hz, 2H), 6.71 (d, J=9.9 Hz, 1H), 6.25 (d, J=7.6 Hz, 1H), 4.56 (t, J=4.4 Hz, 1H), 4.45 (d, J=15.9 Hz, 1H), 4.32 (d, J=15.9 Hz, 1H), 3.26 (dd, J=14.9, 4.6 Hz, 1H), 3.16 (dd, J=14.9, 4.3 Hz, 1H); $^{13}$C NMR (126 MHz, DMSO-d$_6$) δ 174.10, 163.31, 161.37, 156.79, 139.61, 133.11, 130.42, 129.87, 126.24, 122.36, 120.88, 119.88, 118.31, 116.21, 114.25, 113.93, 109.99, 57.67, 26.60; ESI-MS m/z 394.3 (M+Na)$^+$; ESI-HRMS m/z calcd for C$_{19}$H$_{15}$ClFN$_3$NaO$_2$ (M+Na)$^+$ 394.0729, found 394.0722.

1an: $^1$H NMR (400 MHz, DMSO-d$_6$) δ 11.35 (s, 1H), 8.51 (s, 1H), 7.55 (d, J=7.9 Hz, 1H), 7.22 (d, J=3.5 Hz, 1H), 7.20 (d, J=11.1 Hz, 1H), 7.14 (d, J=7.5 Hz, 1H), 6.96 (t, J=7.8 Hz, 1H), 6.70 (ddd, J=13.1, 6.5, 1.3 Hz, 1H), 5.70 (t, J=7.1 Hz, 1H), 4.52 (t, J=4.2 Hz, 1H), 4.44 (d, J=16.2 Hz, 1H), 4.35 (d, J=16.1 Hz, 1H), 3.24 (dd, J=14.9, 4.4 Hz, 1H), 3.12 (dd, J=14.9, 4.2 Hz, 1H); $^{13}$C NMR (126 MHz, DMSO-d$_6$) δ 173.96, 156.48, 150.79, 148.74, 146.67, 133.08, 129.88, 126.40, 126.04, 124.56, 123.05, 120.89, 119.92, 118.41, 116.51, 116.12, 109.16, 57.71, 26.48; ESI-MS m/z 412.4 (M+Na)$^+$; ESI-HRMS m/z calcd for C$_{19}$H$_{14}$ClF$_2$N$_3$NaO$_2$ (M+Na)$^+$ 412.0635, found 412.0642.

1ao: $^1$H NMR (400 MHz, DMSO-d$_6$) δ 11.27 (s, 1H), 8.42 (s, 1H), 7.52 (d, J=7.9 Hz, 1H), 7.17 (d, J=2.4 Hz, 1H), 7.13 (d, J=7.4 Hz, 1H), 6.99 (dd, J=8.5, 2.3 Hz, 1H), 6.95 (dd, J=9.3, 6.2 Hz, 1H), 6.83 (ddd, J=11.2, 7.8, 2.0 Hz, 1H), 6.24-6.14 (m, 1H), 4.49 (t, J=4.1 Hz, 1H), 4.35 (d, J=15.7 Hz, 1H), 4.23 (d, J=15.7 Hz, 1H), 3.22 (dd, J=14.9, 4.4 Hz, 1H), 3.10 (dd, J=14.9, 4.3 Hz, 1H); $^{13}$C NMR (126 MHz, DMSO-d$_6$) δ 174.03, 156.73, 150.27, 148.31, 134.43, 133.03, 129.80, 126.27, 123.28, 120.84, 119.84, 118.32, 117.34, 117.21, 116.34, 116.16, 109.10, 57.59, 26.51; ESI-MS m/z 412.4 (M+Na)$^+$; ESI-HRMS m/z calcd for C$_{19}$H$_{14}$ClF$_2$N$_3$NaO$_2$ (M+Na)$^+$ 412.0635, found 412.0635.

1ap: $^1$H NMR (400 MHz, DMSO-d$_6$) δ 11.26 (s, J=1.4 Hz, 1H), 8.50 (s, 1H), 7.53 (d, J=7.9 Hz, 1H), 7.20 (d, J=2.4 Hz, 1H), 7.11 (d, J=7.4 Hz, 1H), 7.03-6.93 (m, 2H), 6.41 (d, J=6.2 Hz, 2H), 4.53 (t, J=4.3 Hz, 1H), 4.42 (d, J=16.0 Hz, 1H), 4.31 (d, J=16.0 Hz, 1H), 3.22 (dd, J=15.0, 4.6 Hz, 1H), 3.14 (dd, J=14.9, 4.4 Hz, 1H); $^{13}$C NMR (126 MHz, DMSO-d$_6$) δ 174.15, 163.60, 161.63, 156.71, 141.34, 133.09, 129.75, 126.20, 120.86, 119.75, 118.13, 116.38, 110.11, 109.95, 109.22, 103.14, 102.94, 57.72, 26.61; ESI-MS m/z 412.4 (M+Na)$^+$; ESI-HRMS m/z calcd for C$_{19}$H$_{14}$ClF$_2$N$_3$NaO$_2$ (M+Na)$^+$ 412.0635, found 412.0628.

1aq: $^1$H NMR (500 MHz, DMSO-d$_6$) δ 11.28 (s, 1H), 8.46 (s, 1H), 7.48 (d, J=7.9 Hz, 1H), 7.14 (dd, J=27.0, 4.9 Hz, 2H), 6.92 (t, J=7.8 Hz, 1H), 6.73 (dd, J=9.5, 1.9 Hz, 1H), 5.88 (dd, J=8.2, 2.2 Hz, 1H), 4.47 (t, J=4.2 Hz, 1H), 4.36 (d, J=15.8 Hz, 1H), 4.28 (d, J=15.8 Hz, 1H), 3.21 (dd, J=14.9, 4.3 Hz, 1H), 3.08 (dd, J=14.9, 4.2 Hz, 1H); $^{13}$C NMR (500 MHz, DMSO-d$_6$) δ 173.88, 156.44, 139.96, 137.98, 132.99, 129.76, 126.37, 122.72, 122.65, 121.62, 120.82, 119.85, 118.36, 116.04, 112.23, 112.06, 108.99, 57.56, 26.48; ESI-MS m/z 430.3 (M+Na)$^+$; ESI-HRMS m/z calcd for C$_{19}$H$_{13}$ClF$_3$N$_3$NaO$_2$ (M+Na)$^+$ 430.0540, found 430.0543.

1ar: $^1$H NMR (500 MHz, DMSO-d$_6$) δ 11.29 (s, 1H), 8.37 (s, 1H), 7.55 (d, J=7.8 Hz, 1H), 7.18 (d, J=8.4 Hz, 1H), 7.13 (d, J=7.5 Hz, 1H), 6.94 (dd, J=15.3, 7.6 Hz, 2H), 6.72 (s, 1H), 6.24 (d, J=6.4 Hz, 1H), 4.47 (t, J=5.4 Hz, 1H), 4.35 (d, J=15.6 Hz, 1H), 4.21 (d, J=15.6 Hz, 1H), 3.18 (dd, J=14.6, 4.3 Hz, 1H), 3.12 (dd, J=14.8, 3.7 Hz, 1H), 2.28 (s, 1H), 2.16 (s, 2H); $^{13}$C NMR (126 MHz, DMSO-d$_6$) δ 174.16, 156.93, 137.70, 136.74, 133.12, 129.97, 128.47, 127.97, 127.63, 126.25, 123.64, 120.86, 119.86, 118.33, 116.16, 109.41, 63.33, 57.62, 26.62, 21.32; ESI-MS m/z 390.4 (M+Na)$^+$; ESI-HRMS m/z calcd for C$_{20}$H$_{18}$ClN$_3$NaO$_2$ (M+Na)$^+$ 390.0980, found 390.0975.

1as: $^1$H NMR (500 MHz, DMSO-d$_6$) δ 11.32 (d, J=1.4 Hz, 1H), 8.44 (s, 1H), 7.56 (d, J=7.9 Hz, 1H), 7.21 (d, J=2.4 Hz, 1H), 7.14 (d, J=7.5 Hz, 1H), 6.96 (t, J=7.8 Hz, 1H), 6.84 (d, J=7.9 Hz, 2H), 6.43 (d, J=7.9 Hz, 2H), 4.46 (t, J=4.2 Hz, 1H), 4.34 (d, J=15.5 Hz, 1H), 4.18 (d, J=15.5 Hz, 1H), 3.22 (dd, J=14.9, 4.5 Hz, 1H), 3.13 (dd, J=14.9, 4.3 Hz, 1H), 2.19 (s, 3H); $^{13}$C NMR (126 MHz, DMSO-d$_6$) δ 174.10, 156.89, 136.18, 133.72, 133.13, 130.00, 129.05, 127.83, 126.37, 120.82, 119.85, 118.42, 116.17, 109.24, 57.60, 26.53, 21.17; ESI-MS m/z 390.4 (M+Na)$^+$; ESI-HRMS m/z calcd for C$_{20}$H$_{18}$ClN$_3$NaO$_2$ (M+Na)$^+$ 390.0980, found 390.0983.

1at: $^1$H NMR (400 MHz, DMSO-d$_6$) δ 11.34 (s, 1H), 8.39 (s, 1H), 7.55 (d, J=7.9 Hz, 1H), 7.35 (d, J=8.3 Hz, 2H), 7.19 (d, J=2.4 Hz, 1H), 7.16 (d, J=7.5 Hz, 1H), 6.96 (t, J=7.8 Hz, 1H), 6.21 (d, J=8.3 Hz, 2H), 4.49 (t, J=4.0 Hz, 1H), 4.35 (d, J=15.9 Hz, 1H), 4.16 (d, J=15.9 Hz, 1H), 3.25 (dd, J=14.9, 4.2 Hz, 1H), 3.09 (dd, J=14.9, 4.2 Hz, 1H); $^{13}$C NMR (126 MHz, DMSO-d$_6$) δ 174.00, 156.73, 137.17, 136.50, 133.07, 129.94, 128.74, 126.40, 120.90, 119.97, 118.48, 116.14, 109.15, 93.10, 57.66, 26.40; ESI-MS m/z 502.3 (M+Na)$^+$; ESI-HRMS m/z calcd for C$_{19}$H$_{15}$ClIN$_3$NaO$_2$ (M+Na)$^+$ 501.9789, found 501.9784

1au: $^1$H NMR (400 MHz, DMSO-d$_6$) δ 11.33 (s, 1H), 8.41 (s, 1H), 7.56 (d, J=7.9 Hz, 1H), 7.20 (d, J=2.4 Hz, 1H), 7.16 (d, J=7.5 Hz, 1H), 6.97 (t, J=7.8 Hz, 1H), 6.83 (d, J=8.9 Hz, 1H), 6.54 (dd, J=8.6, 5.5 Hz, 2H), 4.49 (t, J=4.1 Hz, 1H), 4.38 (d, J=15.6 Hz, 1H), 4.22 (d, J=15.6 Hz, 1H), 3.24 (dd, J=14.9, 4.3 Hz, 1H), 3.12 (dd, J=14.9, 4.2 Hz, 1H); $^{13}$C NMR (126 MHz, DMSO-d$_6$) δ 174.00, 156.73, 137.17, 136.50, 133.07, 129.94, 128.74, 126.40, 120.90, 119.97, 118.48, 116.14, 109.15, 93.10, 57.66, 26.40; ESI-MS m/z 394.3 (M+Na)$^+$; ESI-HRMS m/z calcd for C$_{19}$H$_{15}$ClFN$_3$NaO$_2$$^+$ (M+Na)$^+$ 394.0729, found 394.0730.

1av: $^1$H NMR (400 MHz, DMSO-d$_6$) δ 11.29 (s, 1H), 8.42 (s, 1H), 7.55 (d, J=7.9 Hz, 1H), 7.21 (dd, J=11.7, 1.9 Hz, 2H), 7.14 (d, J=7.5 Hz, 1H), 7.05 (d, J=2.8 Hz, 1H), 7.02 (d, J=7.9 Hz, 1H), 6.97 (t, J=7.8 Hz, 1H), 6.28 (d, J=7.7 Hz, 1H), 4.52 (t, J=4.4 Hz, 1H), 4.40 (d, J=15.8 Hz, 1H), 4.27 (d, J=15.8 Hz, 1H), 3.21 (dd, J=13.9, 3.7 Hz, 1H), 3.12 (dd, J=14.9, 4.4 Hz, 1H); $^{13}$C NMR (126 MHz, DMSO-d$_6$) 174.12, 156.77, 139.26, 133.25, 133.11, 130.32, 129.88, 127.36, 127.19, 126.24, 125.02, 120.90, 119.89, 118.31, 116.19, 109.29, 57.67, 40.56, 40.48, 40.31, 40.14, 39.98, 39.81, 39.64, 39.48, 26.60; ESI-MS m/z 410.3 (M+Na)$^+$; ESI-HRMS m/z calcd for C$_{19}$H$_{15}$Cl$_2$N$_3$NaO$_2$ (M+Na)$^+$ 410.0433, found 410.0433.

1aw: $^1$H NMR (500 MHz, DMSO-d$_6$) δ 11.39 (s, 1H), 8.42 (s, 1H), 7.60 (dd, J=5.6, 3.8 Hz, 3H), 7.46 (t, J=7.7 Hz, 2H), 7.35 (t, J=14.7 Hz, 1H), 7.30 (d, J=8.2 Hz, 2H), 7.24 (d, J=2.3 Hz, 1H), 7.17 (d, J=7.4 Hz, 1H), 6.99 (t, J=7.8 Hz, 1H), 6.49 (d, J=8.1 Hz, 2H), 4.53 (t, J=4.0 Hz, 1H), 4.46 (d, J=15.9 Hz, 1H), 4.27 (d, J=15.9 Hz, 1H), 3.28 (dd, J=14.9, 4.2 Hz, 1H), 3.14 (dd, J=14.9, 4.1 Hz, 1H); $^{13}$C NMR (126 MHz, DMSO-d$_6$) δ 174.10, 156.87, 140.24, 139.08, 135.88, 133.16, 130.09, 129.33, 127.81, 126.95, 126.78, 126.47, 120.94, 120.00, 118.58, 116.16, 109.27, 57.74, 26.44; ESI-MS m/z 452.4 (M+Na)$^+$; ESI-HRMS m/z calcd for C$_{25}$H$_{20}$ClN$_3$NaO$_2$ (M+Na)$^+$ 452.1136, found 452.1133.

1ax: $^1$H NMR (400 MHz, DMSO-d$_6$) δ 11.41 (s, 1H), 8.51 (s, 1H), 7.57 (d, J=7.9 Hz, 1H), 7.33 (dd, J=8.7, 2.6 Hz, 1H), 7.22 (d, J=2.4 Hz, 1H), 7.16 (d, J=7.4 Hz, 1H), 6.97 (t, J=7.8 Hz, 1H), 6.59 (dd, J=8.5, 2.6 Hz, 1H), 5.62 (dd, J=8.6, 6.1 Hz, 1H), 4.55 (t, J=3.9 Hz, 1H), 4.37 (d, J=16.5 Hz, 1H), 4.28 (d, J=16.6 Hz, 1H), 3.27 (dd, J=14.9, 4.1 Hz, 1H), 3.13 (dd, J=14.9, 4.1 Hz, 1H); $^{13}$C NMR (126 MHz, DMSO-d$_6$) δ 174.01, 162.06, 160.10, 156.53, 133.07, 132.31, 129.94, 129.87, 128.09, 126.50, 121.01, 120.08, 118.61, 116.95, 116.07, 113.96, 109.19, 57.86, 26.35; ESI-MS m/z 428.3 (M+Na)$^+$; ESI-HRMS m/z calcd for C$_{19}$H$_{14}$Cl$_2$FN$_3$NaO$_2$ (M+Na)$^+$ 428.0339, found 428.0340.

1ay: $^1$H NMR (400 MHz, DMSO-d$_6$) δ 11.35 (s, 1H), 8.50 (s, 1H), 7.59 (d, J=7.2 Hz, 1H), 7.55 (d, J=8.0 Hz, 1H), 7.21 (d, J=2.4 Hz, 1H), 7.14 (d, J=7.2 Hz, 1H), 6.96 (t, J=7.8 Hz, 1H), 6.90 (t, J=7.8 Hz, 1H), 6.16 (t, J=7.2 Hz, 1H), 4.54 (t, J=4.1 Hz, 1H), 4.48 (d, J=16.3 Hz, 1H), 4.38 (d, J=16.2 Hz, 1H), 3.25 (dd, J=14.9, 4.4 Hz, 1H), 3.12 (dd, J=14.9, 4.2 Hz, 1H); $^{13}$C NMR (126 MHz, DMSO-d$_6$) δ 174.12, 157.55, 156.53, 155.51, 133.04, 132.51, 129.77, 126.35, 125.39, 124.58, 123.99, 121.83, 120.95, 120.02, 118.40, 116.13, 109.02, 57.77, 34.37, 26.31; ESI-MS m/z 462.4 (M+Na)$^+$; ESI-HRMS m/z calcd for C$_{20}$H$_{14}$ClF$_4$N$_3$NaO$_2$ (M+Na)$^+$ 462.0603, found 462.0616.

1az: $^1$H NMR (400 MHz, DMSO-d$_6$) δ 11.24 (s, 1H), 8.43 (s, 1H), 7.64 (d, J=12.1 Hz, 2H), 7.48 (d, J=7.9 Hz, 1H), 7.39 (s, 1H), 7.20 (d, J=2.2 Hz, 1H), 7.12 (d, J=7.5 Hz, 1H), 6.94 (t, J=7.8 Hz, 1H), 4.59-4.50 (m, 3H), 3.16 (dd, J=14.9, 4.6 Hz, 1H), 3.10 (dd, J=14.9, 5.8 Hz, 1H); $^{13}$C NMR (126 MHz, DMSO-d$_6$) δ 174.32, 156.67, 136.63, 135.07, 133.17, 130.84, 129.68, 128.32, 128.06, 126.16, 126.02, 125.04, 122.87, 120.88, 119.80, 117.96, 116.21, 109.41, 57.68, 26.92; ESI-MS m/z 478.4 (M+Na)⁺; ESI-HRMS m/z calcd for $C_{20}H_{14}Cl_2F_3N_3NaO_2$ (M+Na)⁺ 478.0307, found 478.0326.

1aaa: ¹H NMR (500 MHz, DMSO-$d_6$) δ 11.39 (s, 1H), 8.46 (s, 1H), 8.16 (dd, J=4.5, 1.5 Hz, 2H), 7.56 (d, J=7.9 Hz, 1H), 7.20 (d, J=2.4 Hz, 1H), 7.16 (d, J=7.3 Hz, 1H), 6.96 (t, J=7.8 Hz, 1H), 6.29 (d, J=5.8 Hz, 2H), 4.54 (t, J=4.0 Hz, 1H), 4.42 (d, J=16.7 Hz, 1H), 4.24 (d, J=16.7 Hz, 1H), 3.27 (dd, J=14.9, 4.1 Hz, 1H), 3.11 (dd, J=14.9, 4.2 Hz, 1H); ¹³C NMR (126 MHz, DMSO-$d_6$) δ 174.01, 156.61, 149.60, 145.62, 133.11, 129.97, 126.51, 126.45, 121.31, 121.19, 121.02, 120.05, 118.59, 118.51, 116.15, 109.19, 57.84, 26.37; ESI-MS m/z 377.3 (M+Na)⁺; ESI-HRMS m/z calcd for $C_{18}H_{15}ClN_4NaO_2$ (M+Na)⁺ 377.0776, found 377.0791.

1gaa: ¹H NMR (400 MHz, DMSO-$d_6$) δ 11.53 (s, 1H), 8.44 (s, 1H), 8.15 (d, J=5.7 Hz, 2H), 7.51 (dd, J=8.6, 4.9 Hz, 1H), 7.18 (s, 1H), 6.97 (t, J=9.4 Hz, 1H), 6.31 (d, J=5.4 Hz, 2H), 4.51 (s, 1H), 4.39 (d, J=16.7 Hz, 1H), 4.23 (d, J=16.5 Hz, 1H), 3.23 (dd, J=14.8, 4.0 Hz, 1H), 3.07 (dd, J=15.1, 4.0 Hz, 1H); ¹³C NMR (126 MHz, DMSO-$d_6$) δ 173.98, 156.61, 155.13, 153.25, 149.56, 145.60, 133.48, 126.90, 126.03, 121.35, 119.06, 109.43, 108.57, 102.41, 57.74, 26.19; ESI-MS m/z 373.2 (M+H)⁺; ESI-HRMS m/z calcd for $C_{18}H_{15}ClN_4NaO_2^+$ (M+H)⁺ 373.0861, found 373.0873.

1gl: ¹H NMR (500 MHz, DMSO-$d_6$) δ 11.54 (s, 1H), 8.51 (s, 1H), 7.52 (dd, J=8.7, 4.7 Hz, 1H), 7.22 (d, J=2.3 Hz, 1H), 7.18 (dd, J=7.4, 7.4 Hz, 1H), 7.04 (dd, J=14.1, 4.5 Hz, 1H), 6.97 (dd, J=10.1, 8.7 Hz, 1H), 6.70 (t, J=7.5 Hz, 1H), 5.86 (t, J=7.5 Hz, 1H), 4.50 (t, J=4.2 Hz, 1H), 4.38 (d, J=16.2 Hz, 1H), 4.29 (d, J=16.1 Hz, 1H), 3.22 (dd, J=14.9, 4.3 Hz, 1H), 3.11 (dd, J=14.9, 4.3 Hz, 1H); ¹³C NMR (126 MHz, DMSO-$d_6$) δ 174.01, 160.78, 158.84, 156.60, 155.10, 153.22, 133.48, 129.28, 127.74, 126.01, 124.21, 123.44, 118.99, 115.43, 109.40, 108.44, 102.40, 57.64, 26.26; ESI-MS m/z 412.3 (M+Na)⁺; ESI-HRMS m/z calcd for $C_{19}H_{14}ClF_2N_3NaO_2$ (M+Na)⁺ 412.0635, found 412.0642.

1gm: ¹H NMR (500 MHz, DMSO-$d_6$) δ 11.44 (s, 1H), 8.45 (s, 1H), 7.49 (dd, J=8.7, 4.7 Hz, 1H), 7.19 (d, J=2.4 Hz, 1H), 7.03 (dd, J=7.9, 6.2 Hz, 1H), 6.95 (ddd, J=7.7, 6.3, 5.4 Hz, 2H), 6.54 (d, J=8.3 Hz, 1H), 6.25 (d, J=7.7 Hz, 1H), 4.49 (td, J=4.2, 0.7 Hz, 1H), 4.38 (d, J=15.9 Hz, 1H), 4.25 (d, J=15.9 Hz, 1H), 3.20 (dd, J=14.9, 4.4 Hz, 1H), 3.09 (dd, J=14.9, 4.3 Hz, 1H); ¹³C NMR (126 MHz, DMSO-$d_6$) 174.07, 163.27, 161.33, 156.78, 155.10, 153.22, 139.56, 133.47, 130.28, 126.78, 125.90, 122.46, 118.82, 114.22, 109.33, 108.35, 102.51, 57.56, 26.31; ESI-MS m/z 412.3 (M+Na)⁺; ESI-HRMS m/z calcd for $C_{19}H_{14}ClF_2N_3NaO_2$ (M+Na)⁺ 412.0635, found 412.0641.

1gn: ¹H NMR (500 MHz, DMSO-$d_6$) δ 11.48 (s, 1H), 8.48 (s, 1H), 7.49 (dd, J=8.7, 4.7 Hz, 1H), 7.25-7.15 (m, 2H), 6.96 (dd, J=10.1, 8.7 Hz, 1H), 6.70 (dd, J=8.1, 1.5 Hz, 2H), 5.78 (t, J=7.1 Hz, 1H), 4.49 (t, J=4.1 Hz, 1H), 4.41 (d, J=16.0 Hz, 1H), 4.32 (d, J=16.0 Hz, 1H), 3.21 (dd, J=14.9, 4.3 Hz, 1H), 3.08 (dd, J=14.9, 4.2 Hz, 1H); ¹³C NMR (126 MHz, DMSO-$d_6$) 173.95, 156.50, 155.09, 153.20, 150.77, 148.65, 146.68, 133.44, 126.85, 125.88, 124.30, 123.16, 118.85, 116.33, 109.22, 108.36, 102.40, 57.61, 26.20; ESI-MS m/z 430.4 (M+Na)⁺; ESI-HRMS m/z calcd for $C_{19}H_{13}ClF_3N_3NaO_2$ (M+Na)⁺ 430.0540, found 430.0545.

1go: ¹H NMR (500 MHz, DMSO-$d_6$) δ 11.40 (s, 1H), 8.41 (s, 1H), 7.46 (dd, J=8.7, 4.7 Hz, 1H), 7.15 (d, J=2.4 Hz, 1H), 7.00 (dd, J=8.5, 2.2 Hz, 1H), 6.94 (dd, J=10.0, 8.8 Hz, 1H), 6.71 (ddd, J=11.1, 7.8, 2.0 Hz, 1H), 6.31 (s, 1H), 4.47 (t, J=4.2 Hz, 1H), 4.32 (d, J=15.6 Hz, 1H), 4.21 (d, J=15.6 Hz, 1H), 3.20 (dd, J=14.9, 4.2 Hz, 1H), 3.06 (dd, J=14.9, 4.3 Hz, 1H); ¹³C NMR (126 MHz, DMSO-$d_6$) δ 173.99, 156.76, 155.10, 153.22, 150.35, 148.39, 134.38, 133.40, 126.74, 125.80, 123.50, 118.80, 117.26, 116.29, 109.19, 108.14, 102.47, 57.58, 26.30; ESI-MS m/z 430.4 (M+Na)⁺; ESI-HRMS m/z calcd for $C_{19}H_{13}ClF_3N_3NaO_2$ (M+Na)⁺ 430.0540, found 430.0552.

1gp: ¹H NMR (400 MHz, DMSO-$d_6$) δ 11.38 (s, 1H), 8.43 (s, 1H), 7.47 (dd, J=8.7, 4.7 Hz, 1H), 7.17 (d, J=2.4 Hz, 1H), 7.00-6.92 (m, 2H), 6.33 (dd, J=8.2, 2.1 Hz, 2H), 4.51 (t, J=4.1 Hz, 1H), 4.40 (d, J=16.0 Hz, 1H), 4.28 (d, J=16.0 Hz, 1H), 3.21 (dd, J=14.9, 4.3 Hz, 1H), 3.08 (dd, J=14.9, 4.3 Hz, 1H); ¹³C NMR (126 MHz, DMSO-$d_6$) δ 174.12, 163.47, 161.51, 156.77, 155.10, 153.21, 141.11, 133.43, 126.71, 125.68, 118.55, 110.03, 109.83, 108.28, 102.69, 57.57, 26.17; ESI-MS m/z 430.4 (M+Na)⁺; ESI-HRMS m/z calcd for $C_{19}H_{13}ClF_3N_3NaO_2$ (M+Na)⁺ 430.0540, found 430.0541.

1gq: ¹H NMR (400 MHz, DMSO-$d_6$) δ 11.43 (s, 1H), 8.43 (s, 1H), 7.44 (dd, J=8.7, 4.7 Hz, 1H), 7.16 (d, J=2.4 Hz, 1H), 6.95 (dd, J=10.1, 8.7 Hz, 1H), 6.81 (d, J=6.4, 4.9 Hz, 1H), 6.08 (dd, J=10.6, 2.4 Hz, 1H), 4.47 (t, J=4.0 Hz, 1H), 4.37 (d, J=15.6 Hz, 1H), 4.29 (d, J=15.6 Hz, 1H), 3.20 (dd, J=14.9, 4.2 Hz, 1H), 3.05 (dd, J=14.9, 4.2 Hz, 1H); ¹³C NMR (126 MHz, DMSO-$d_6$) δ 173.83, 156.49, 155.07, 153.18, 139.92, 137.94, 133.35, 126.74, 125.71, 123.01, 121.43, 118.75, 111.88, 109.05, 108.24, 102.31, 57.41, 34.16, 26.25; ESI-MS m/z 448.4 (M+Na)⁺; ESI-HRMS m/z calcd for $C_{19}H_{12}ClF_4N_3NaO_2$ (M+Na)⁺ 448.0446, found 448.0430.

1gu: ¹H NMR (500 MHz, DMSO-$d_6$) δ 11.48 (s, 1H), 8.42 (s, 1H), 7.50 (dd, J=8.7, 4.7 Hz, 1H), 7.18 (d, J=2.4 Hz, 1H), 6.97 (dd, J=10.1, 8.7 Hz, 1H), 6.82 (t, J=6.1 Hz, 2H), 6.56 (dd, J=8.4, 5.6 Hz, 2H), 4.46 (t, J=3.8 Hz, 1H), 4.34 (d, J=15.6 Hz, 1H), 4.20 (d, J=15.6 Hz, 1H), 3.20 (dd, J=14.9, 4.3 Hz, 1H), 3.07 (dd, J=14.9, 4.2 Hz, 1H); ¹³C NMR (126 MHz, DMSO-$d_6$) δ 174.06, 162.39, 160.46, 156.82, 155.09, 153.21, 133.40, 132.81, 128.62, 126.80, 125.95, 118.95, 115.12, 114.96, 109.27, 108.39, 102.18, 57.52, 26.17; ESI-MS m/z 412.3 (M+Na)⁺; ESI-HRMS m/z calcd for $C_{19}H_{14}ClF_2N_3NaO_2^+$(M+Na)⁺ 412.0635, found 412.0643.

1gv: ¹H NMR (400 MHz, DMSO-$d_6$) δ 11.43 (s, 1H), 8.39 (s, 1H), 7.50 (dd, J=8.7, 4.7 Hz, 1H), 7.21 (d, J=9.2 Hz, 1H), 7.18 (d, J=2.3 Hz, 1H), 7.01 (dt, J=18.9, 8.9 Hz, 3H), 6.34 (d, J=7.7 Hz, 1H), 4.50 (t, J=4.4 Hz, 1H), 4.38 (d, J=15.8 Hz, 1H), 4.26 (d, J=15.8 Hz, 1H), 3.20 (dd, J=14.9, 4.5 Hz, 1H), 3.09 (dd, J=14.9, 4.3 Hz, 1H); ¹³C NMR (126 MHz, DMSO-$d_6$) δ 174.11, 156.82, 155.11, 153.23, 139.11, 133.47, 133.25, 130.14, 127.34, 127.14, 126.70, 125.87, 125.11, 118.75, 109.31, 108.39, 102.52, 57.58, 26.27; ESI-MS m/z 428.4 (M+Na)⁺; ESI-HRMS m/z calcd for $C_{19}H_{14}Cl_2FN_3NaO_2$ (M+Na)⁺ 428.0339, found 428.0327.

Example 6

Exemplary Halogenation

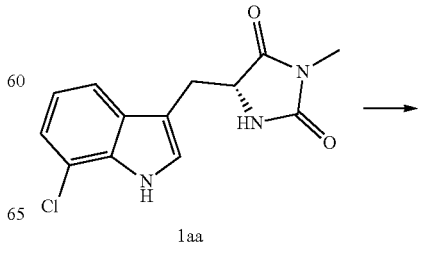

1aa

-continued

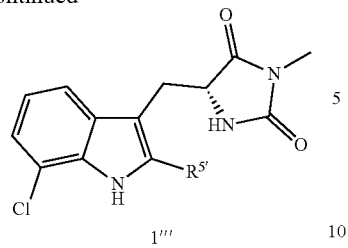

1'''

Compounds of structure (III), wherein $R^5$ is halogen (i.e., compound 1''', wherein $R^5$ is $R^{5'}$) were prepared according to the following procedure. To a solution of compound 1aa (0.27g, 1 mmol) in carbon tetrachloride, halogenation reagent (1 equiv) was added under $N_2$ atmosphere. The reaction was allowed to stir at room temperature for 2-2.5 h until TLC detected the reaction was complete (eluting with DCM:MeOH=10:1). After cooling to room temperature, filtering and concentrating in vacuum, compound 1''' was afforded by column chromatography.

Table 5 provides exemplary conditions and compounds which were prepared according to the above general procedure.

TABLE 5

Exemplary Preparations of Compound 1'''

| entry | 1 | reagent | 1''' | Yield % |
|---|---|---|---|---|
| 45 | 1aa | NBS | 1aab | 34 |
| 46 | 1aa | NCS | 1aac | 25 |

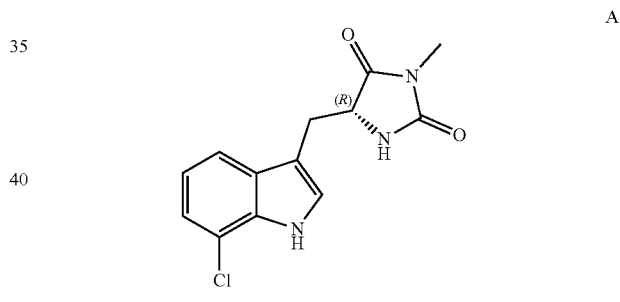

Compounds from Table 5 were analyzed by NMR and mass spectrometry. Data is provided below:

1aab: $^1$H NMR (400 MHz, DMSO-$d_6$) δ 12.15 (s, 1H), 8.12 (s, 1H), 7.48 (d, J=7.9 Hz, 1H), 7.18 (d, J=7.1 Hz, 1H), 7.04 (t, J=7.8 Hz, 1H), 4.33 (ddd, J=6.8, 4.9, 1.6 Hz, 1H), 3.11 (dd, J=14.6, 4.9 Hz, 1H), 2.99 (dd, J=14.6, 7.2 Hz, 1H), 2.70 (s, 3H); $^{13}$C NMR (126 MHz, DMSO-$d_6$) δ 174.17, 157.31, 133.52, 129.60, 121.54, 120.73, 117.72, 115.60, 112.70, 110.24, 56.97, 27.77, 24.46; ESI-MS m/z 380.1 (M+Na)$^+$; ESI-HRMS m/z calcd for $C_{13}H_{11}BrClN_3NaO_2$ (M+Na)$^+$ 377.9616, found 377.9614.

1aac: $^1$H NMR (500 MHz, DMSO-$d_6$) δ 12.13 (s, 1H), 8.11 (s, 1H), 7.48 (d, J=7.9 Hz, 1H), 7.17 (dd, J=7.7, 0.8 Hz, 1H), 7.03 (t, J=7.8 Hz, 1H), 4.32 (ddd, J=6.9, 4.9, 1.6 Hz, 1H), 3.11 (dd, J=14.7, 4.9 Hz, 1H), 2.99 (dd, J=14.7, 7.3 Hz, 1H), 2.70 (s, 3H); $^{13}$C NMR (126 MHz, DMSO-$d_6$) 174.14, 157.25, 131.93, 129.33, 124.58, 121.60, 120.81, 117.86, 115.62, 106.98, 56.91, 26.72, 24.43; ESI-MS m/z 310.0 (M–H)$^-$; ESI-HRMS m/z calcd for $C_{13}H_{10}Cl_2N_3O_2^-$ (M–H)$^-$ 310.0156, found 310.0168.

Example 7

Cellular Necrosis Inhibition Activity by Compounds of Structure (I)

Compound (Ia) was prepared according to the general methods described above. Compound (Ia) and compound A (below) were screened for anti-necrotic activity utilizing human FADD-deficient Jurkat T cells challenged with human TNF-alpha. FADD–/– Jurkat cells (Juo P, et al. Cell Growth Differ. 1999, 10(12):797-804) were seeded at the density of 5*10$^5$ cells/mL into 96 well white plates (Costar) at 100 μL/well. Compound A was identified as an inhibitor of necrosis in U.S. Pat. No. 7,491,743, the full disclosure of which is incorporated herein by reference in its entirety. Cells were treated in duplicate with various concentrations of test compounds in the presence or absence of 10 ng/ml human TNF-alpha. (Cell Sciences). The compounds were also tested in the presence of TNF-alpha and an Smac mimetic (10 nM of SM-164 (Lu et al, Cancer Res., 2008, 68:9384). Smac mimetics are a class of compounds that inhibit IAPs and are thought to induce autocrine TNF-alpha production and cell death. Accordingly, testing the compounds in the presence of Smac provides further evidence of necrosis inhibitory activity.

A

After 30 hours, viability of the cells was determined using luminescent ATP-based cell viability assay (CellTiter-Glo, Promega). Percentage of protection by the compound was calculated as a ratio of the cps (counts per second) value in the well treated with the test compound and TNF-alpha. to the cps value in the well treated with the compound alone. Assays were repeated twice, and the average EC$_{50}$ value over both assays was calculated. Table 6 provides the average EC$_{50}$ (nM) values of compounds (Ia) and A for cell viability.

TABLE 6

Comparative EC$_{50}$ Data for Compounds (Ia) and 2

| Compound | EC50 (nM) TNFα | EC50 (nM) TNFα +Smac |
|---|---|---|
| (Ia) | 26.75 | 86.6 |
| A | 90.5 | 324 |

The data in Table 6 show that compound (Ia) is significantly more active than compound A.

Example 8

Contribution of 6-Fluoro Substituent to Cellular Necrosis Inhibition Activity To investigate the contribution of the 6-fluoro substituent to the necrosis inhibitory activity of compound (Ia), the activity of compound (Ia) was compared to the activity of the following structurally related compounds (B-F below) according to the general procedures of Example 7, the results of which are summarized in Table 7:

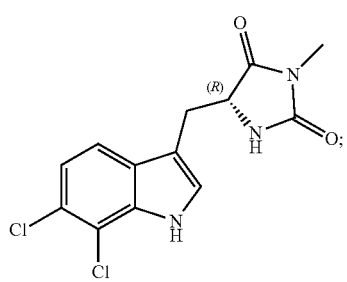
B

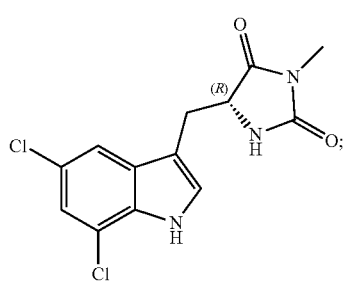
C

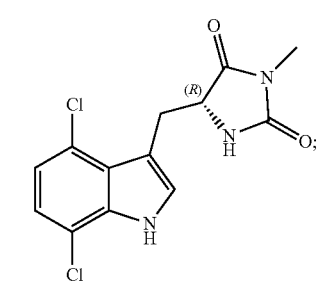
D

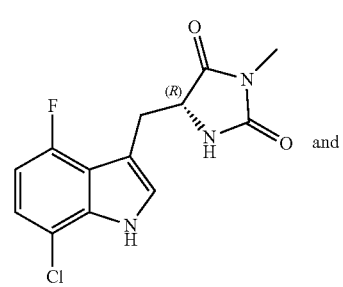
E and

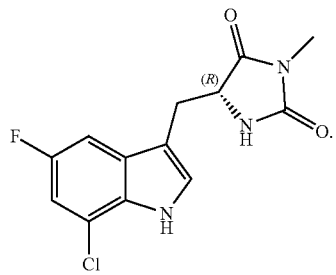
F

TABLE 7

Comparative EC$_{50}$ Data for Compounds (Ia), B, C, D, E and F

| Compound | EC50 (nM) TNFa | EC50 (nM) TNFa +Smac |
|---|---|---|
| (Ia) | 26.75 | 86.6 |
| B | >100,000 | NA* |
| C | NA* | NA* |
| D | NA* | NA* |
| E | 2,330 | 8,330 |
| F | 10,500 | >100,000 |

*NA = no activity

The data in Table 7 show that the type of halogen substituent (Cl vs. F) and its position on the indole ring are both important contributors to the increased activity of compound (Ia) relative to the comparative compounds.

Example 9

RIP1 Kinase Inhibition by Compounds of Structure (I)

RIP1 kinase assays were performed using ADP-Glo assay (Promega) according to manufacturer's protocol. Reactions were performed in 50 mM HEPES, pH 7.5, 50 mM NaCl, 30 mM MgCl$_2$, 1 mM DTT, 0.05% bovine serum albumin (BSA), 0.02% CHAPS buffer, containing 20 ng recombinant GST-human RIP1 kinase domain (amino acids 1-327), 50 mM ATP and 10 serial dilutions of inhibitors. Recombinant GST-RIP1 was generated using baculoviral expression system in Sf9 cells. Protein was purified by glutathione affinity chromatography, followed by size exclusion chromatography. Reactions were performed for 4 hr at room temperature and stopped by incubation with ADP-Glo reagent for 40 min at room temperature. Luminescent signal was developed by incubation with Kinase Detection reagent for 30 min at room temperature. Signal was determined using Victor3V platereader (Perkin Elmer). Non-linear regression to calculate EC50 values was performed using GraphPad Prism software package. Using these methods, Compound Ia was compared to Compound A for the ability to inhibit RIP1 kinase enzymatic activity. As shown in FIG. 1, the EC50 for inhibition of RIP1 kinase was 93.7 nM for Compound Ia (squares), substantially more potent than Compound A (circles), which had an EC50 of 255.9 nM.

Example 10

Cellular Necrosis Inhibition Activity of Compounds of Structure (II)

Exemplary compounds of structure (II) were screened for anti-necrotic activity according to the general procedures of Example 7. Table 8 provides EC$_{50}$ (nM) values for the tested compounds and a comparative compound (C1) described in U.S. Patent Publication No. 2012/0122889, the full disclosure of which is hereby incorporated by reference in its entirety.

TABLE 8

Comparative EC50 Data

| No. | Structure | EC50 (nM) TNFα | EC50 (nM) TNFα + Smac |
|---|---|---|---|
| II-1 | 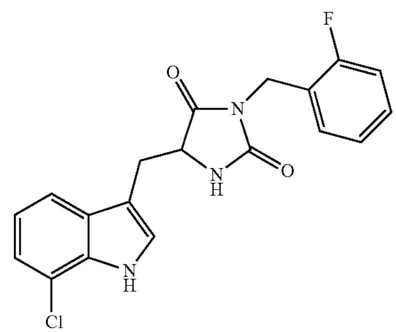 [SMILES: O=C1NC(Cc2c[nH]c3c(Cl)cccc23)C(=O)N1Cc1ccccc1F] | 159 | 11,000 |
| II-2 | 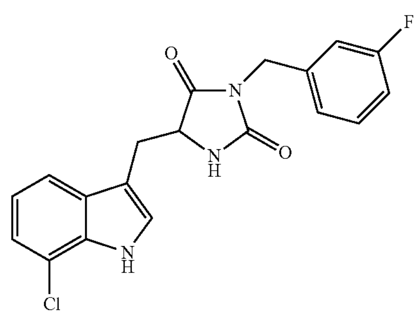 [SMILES: O=C1NC(Cc2c[nH]c3c(Cl)cccc23)C(=O)N1Cc1cccc(F)c1] | 41 | 895 |
| II-3 | 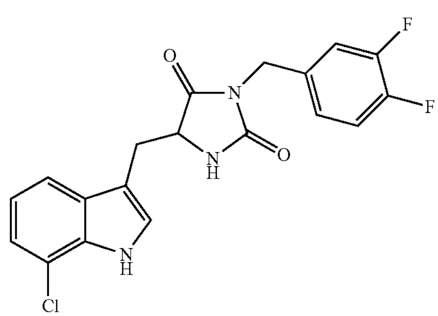 [SMILES: O=C1NC(Cc2c[nH]c3c(Cl)cccc23)C(=O)N1Cc1ccc(F)c(F)c1] | 89 | 426 |
| II-4 | 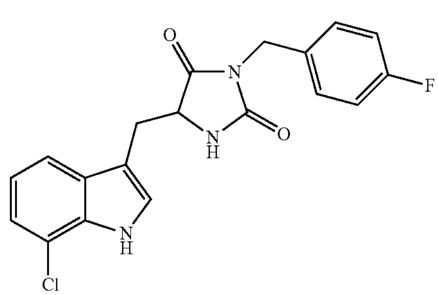 [SMILES: O=C1NC(Cc2c[nH]c3c(Cl)cccc23)C(=O)N1Cc1ccc(F)cc1] | 220 | 867 |

TABLE 8-continued

Comparative EC50 Data

| No. | Structure | EC50 (nM) TNFα | EC50 (nM) TNFα + Smac |
|---|---|---|---|
| II-5 | 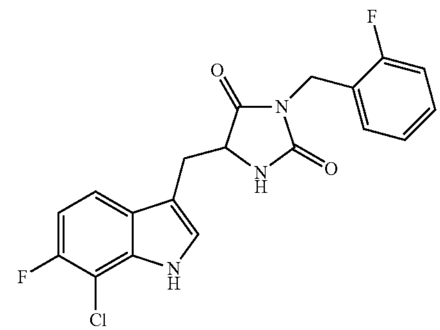 [SMILES: O=C1NC(Cc2c[nH]c3c(Cl)c(F)ccc23)C(=O)N1Cc1ccccc1F] | 235 | 892 |
| II-6 | 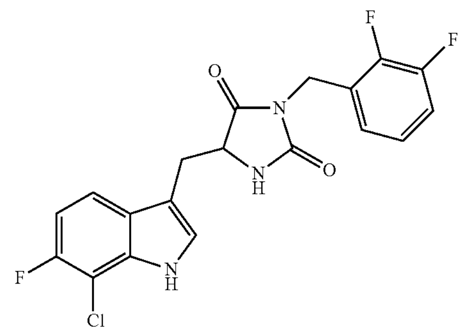 [SMILES: O=C1NC(Cc2c[nH]c3c(Cl)c(F)ccc23)C(=O)N1Cc1cccc(F)c1F] | 50 | 822 |
| II-7 | 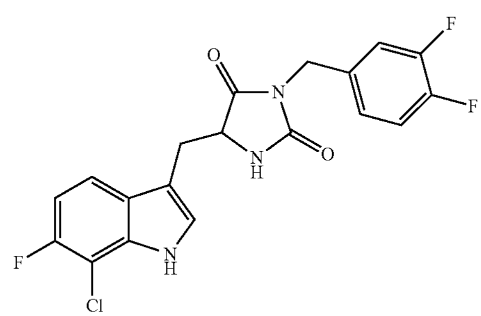 [SMILES: O=C1NC(Cc2c[nH]c3c(Cl)c(F)ccc23)C(=O)N1Cc1ccc(F)c(F)c1] | 121 | 722 |
| C1 | 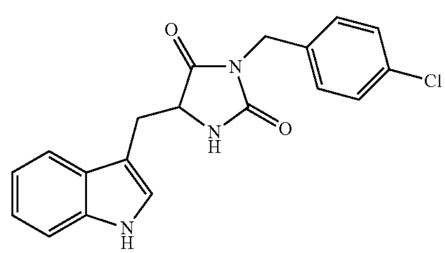 [SMILES: O=C1NC(Cc2c[nH]c3ccccc23)C(=O)N1Cc1ccc(Cl)cc1] | 343 | Not tested |

The data in Table 8 show that the tested compounds of structure (II) are significantly more active than compound C1.

Example 11

RIP1 Kinase Inhibition by Compounds of Structure (II)

RIP1 kinase assays were performed according to the general methods described in Example 9. Using these methods, compounds 1am (5-((7-chloro-1H-indol-3-yl)methyl)-3-(3-fluorobenzyl)imidazolidine-2,4-dione) and 1ao (5-((7-chloro-1H-indol-3-yl)methyl)-3-(3,4-difluorobenzyl) imidazolidine-2,4-dione) were each found to have EC50 values of less than 100 nM.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way.

Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to the present invention.

All of the U.S. patents, U.S. patent application publications, U.S. patent applications, foreign patents, foreign patent applications and non-patent publications referred to in this specification or the attached Application Data Sheet are incorporated herein by reference, in their entirety to the extent not inconsistent with the present description.

The present application claims the benefit of the filing date of Chinese Patent Application No. 201410764426.4, filed Dec. 11, 2014, Chinese Patent Application No. 201410767595.3, filed Dec. 11, 2014, U.S. Provisional Patent Application Ser. No. 62/105,462, filed Jan. 20, 2015, entitled "POTENT INHIBITOR OF CELLULAR NECROSIS," and U.S. Provisional Patent Application Ser. No. 62/105,475, filed Jan. 20, 2015, entitled "METHODS FOR PREPARATION OF CELLULAR NECROSIS INHIBITORS," which applications are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound having the following structure (III):

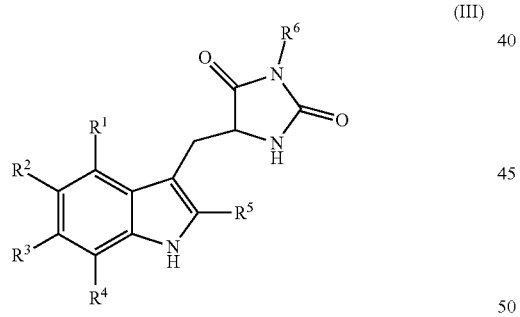

or a pharmaceutically acceptable salt thereof, wherein:
$R^1$, $R^2$, $R^3$ and $R^4$ are each independently H, halo or $C_1$-$C_6$ alkyl;
$R^5$ is H or halo; and
$R^6$ is

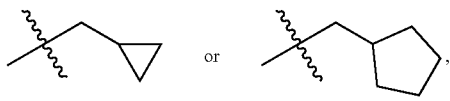 [SMILES: *CC1CC1 ; *CC1CCCC1]

wherein the compound is prepared by a method comprising reacting aldehyde (5), or a salt, thereof, with phenylhydrazine (6), or a salt thereof, to yield (7), or a salt thereof, as follows:

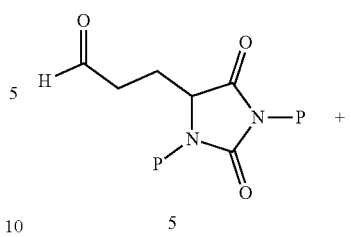

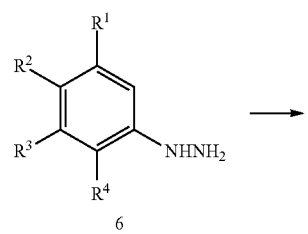

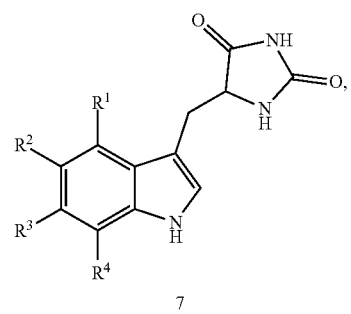

wherein each P is independently H or a protecting group.

2. A pharmaceutical composition comprising the compound of claim 1, or a pharmaceutically acceptable salt thereof, and a pharmaceutically acceptable carrier, diluent or excipient.

3. The compound of claim 1, wherein
$R^1$ is H, Cl, or F;
$R^2$ is H, Cl, or F;
$R^3$ is H, Cl, or F; and
$R^4$ is H, Cl, or I.

4. A compound selected from:

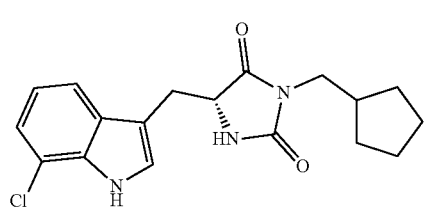

1ad

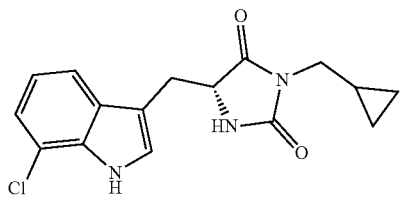

1ae or a pharmaceutically acceptable salt thereof.

5. A pharmaceutical composition comprising the compound of claim 4, or a pharmaceutically acceptable salt, and a pharmaceutically acceptable carrier, diluent or excipient.

6. The compound of claim 3, wherein $R^1$ is H.
7. The compound of claim 3, wherein $R^2$ is H.
8. The compound of claim 3, wherein $R^3$ is H.
9. The compound of claim 3, wherein $R^4$ is Cl.
10. The compound of claim 3, wherein $R^5$ is H.
11. The compound of claim 10, wherein $R^6$ is

12. The compound of claim 10, wherein $R^6$ is

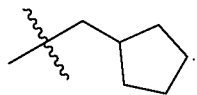

13. The compound of claim 4, wherein the compound is

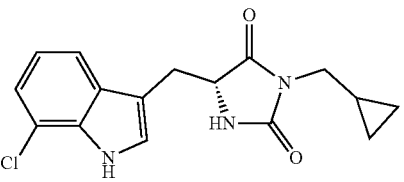

1ae or a pharmaceutically acceptable salt thereof.

14. The compound of claim 4, wherein the compound is

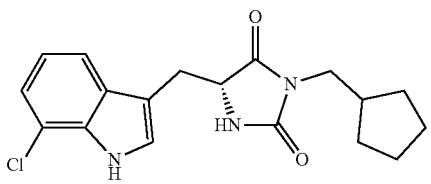

1ad or a pharmaceutically acceptable salt thereof.

15. A pharmaceutical composition comprising the compound of claim 13, or a pharmaceutically acceptable salt, and a pharmaceutically acceptable carrier, diluent or excipient.

16. A pharmaceutical composition comprising the compound of claim 14, or a pharmaceutically acceptable salt, and a pharmaceutically acceptable carrier, diluent or excipient.

* * * * *